US011892425B2

(12) United States Patent
Hummer et al.

(10) Patent No.: US 11,892,425 B2
(45) Date of Patent: Feb. 6, 2024

(54) DEVICE FOR READING, PROCESSING AND TRANSMITTING TEST RESULT DATA FOR PATHOGENS OR VIRUSES IN FLUID TEST SAMPLES

(71) Applicants: Matthew Hummer, Shaker Heights, OH (US); Gregory J. Hummer, Shaker Heights, OH (US)

(72) Inventors: Matthew Hummer, Shaker Heights, OH (US); Gregory J. Hummer, Shaker Heights, OH (US)

( * ) Notice: Subject to any disclaimer, the term of this patent is extended or adjusted under 35 U.S.C. 154(b) by 0 days.

(21) Appl. No.: 17/505,610

(22) Filed: Oct. 19, 2021

(65) Prior Publication Data

US 2022/0373499 A1   Nov. 24, 2022

Related U.S. Application Data

(63) Continuation-in-part of application No. 17/324,085, filed on May 18, 2021, now Pat. No. 11,340,210.

(51) Int. Cl.
*G01N 27/32* (2006.01)
*G01N 27/327* (2006.01)

(52) U.S. Cl.
CPC ..... *G01N 27/3273* (2013.01); *G01N 27/3272* (2013.01); *G01N 27/3274* (2013.01); *G01N 27/3275* (2013.01)

(58) Field of Classification Search
CPC .......... G01N 27/3273; G01N 27/3272; G01N 27/3274; G01N 27/3275
USPC .......................................................... 435/5
See application file for complete search history.

(56) References Cited

U.S. PATENT DOCUMENTS

| | | | |
|---|---|---|---|
| 9,466,057 B2 * | 10/2016 | Beeson | G06Q 20/382 |
| 2014/0273187 A1 * | 9/2014 | Johnson | G01N 33/5438 435/287.2 |
| 2018/0288977 A1 * | 10/2018 | Hummer | G08B 21/182 |

* cited by examiner

*Primary Examiner* — Christine T Mui
(74) *Attorney, Agent, or Firm* — Edmond DeFrank

(57) ABSTRACT

The embodiments disclose an apparatus including a test cartridge configured for inserting into a reader, a sample insertion component coupled to the test cartridge a test sample, a heater device coupled to the test cartridge configured to heat to a predetermined temperature the test sample, a sensor array coupled to the test cartridge consisting of at least one electrochemical sensor for sensing analytes in a sample, a reader configured to gather test related data from the sensor array coupled to the test cartridge, an analyzer coupled to the reader configured for determining test results of each sensor in the sensor array and comparing all the test results for confirmation of a valid test and coherent results, a MCU (Microcontroller Unit) to perform main control and processing functions, and orchestrates all the functionality for the Reader, and a BLE Radio RF link between the MCU and an external processing system.

6 Claims, 78 Drawing Sheets

┌─ 3400
| THE BIOLOGICAL PATHOGEN APP CAN BE CONFIGURED TO DETECT OR TRIGGER AN ALARM WHEN A PATHOGEN WHICH IS CONSIDERED HIGHLY INFECTIOUS IS DETECTED |

3410
| THE BIOLOGICAL PATHOGEN APP IS CONFIGURED TO, ONCE A HIGHLY INFECTIOUS PATHOGEN IS DETECTED, SHARE THE DETECTION INFORMATION |

3420
| FOR EXAMPLE, THE BIOLOGICAL PATHOGEN APP IS CONFIGURED TO USE THE COMMUNICATION CIRCUITRY TO BROADCAST AN ALERT (OR GENERATE A NOTIFICATION) VIA ANY SUITABLE COMMUNICATIONS NETWORK E.G., WIFI, NFC, BLUETOOTH, CELL, AND OTHER NETWORKS |

3430
| THE ALERT MAY BE DIRECTLY SENT TO OTHER CELL PHONES AND/OR PERSONAL COMMUNICATION DEVICES IN THE AREA, OR MAY BE SENT TO A SERVER (OR THROUGH A NETWORK) AND THEN ON TO DEVICES WITHIN A RANGE OF A GIVEN LOCATION |

3440
| THE BIOLOGICAL PATHOGEN APP IS CONFIGURED TO USE LOCATION INFORMATION FROM A GPS CHIP, WIFI OR ANY OTHER LOCATION INFORMATION AVAILABLE TO THE CELL PHONE TO IDENTIFY THE LOCATION OF THE DETECTED HIGHLY INFECTIOUS PATHOGEN |

3450
| THE BIOLOGICAL PATHOGEN APP CAN BE CONFIGURED TO ALERT THE AUTHORITIES IN THE EVENT CERTAIN HIGHLY INFECTIOUS PATHOGENS ARE DETECTED |

3460
| FOR EXAMPLE, THE DETECTION OF SARS-CoV-2 CAN TRIGGER INFORMATION RELATING TO THE LOCATION, TIME, AND OTHER DATA OF THE DETECTION TO BE FORWARDED TO CERTAIN DESIGNATED AUTHORITIES FOR PUBLIC HEALTH THREAT MANAGEMENT/MITIGATION |

FIG. 34

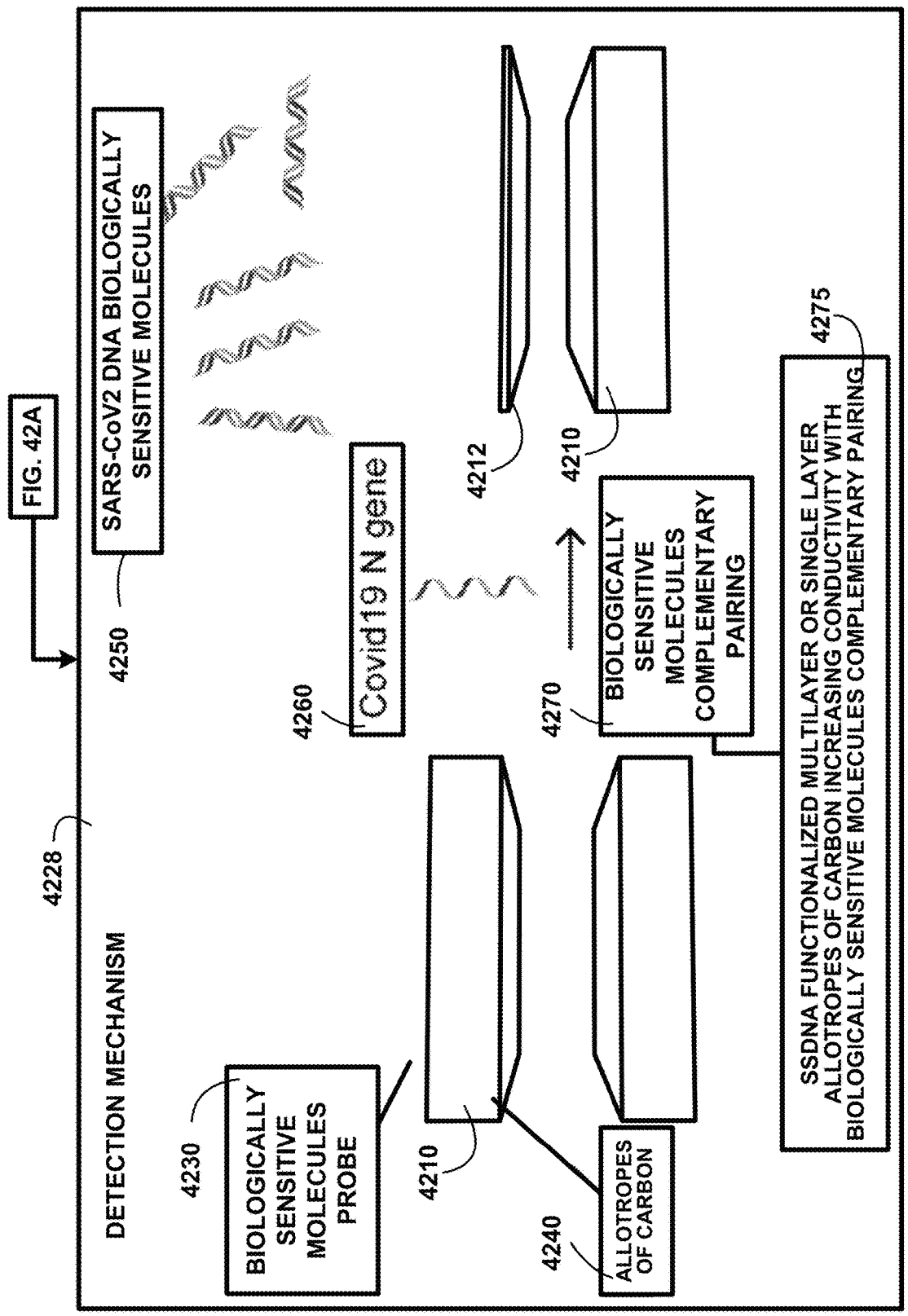

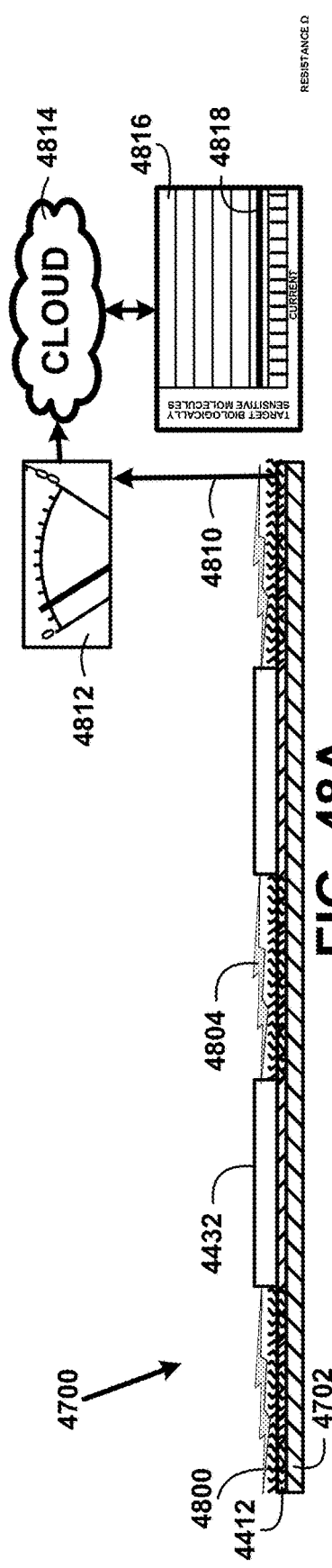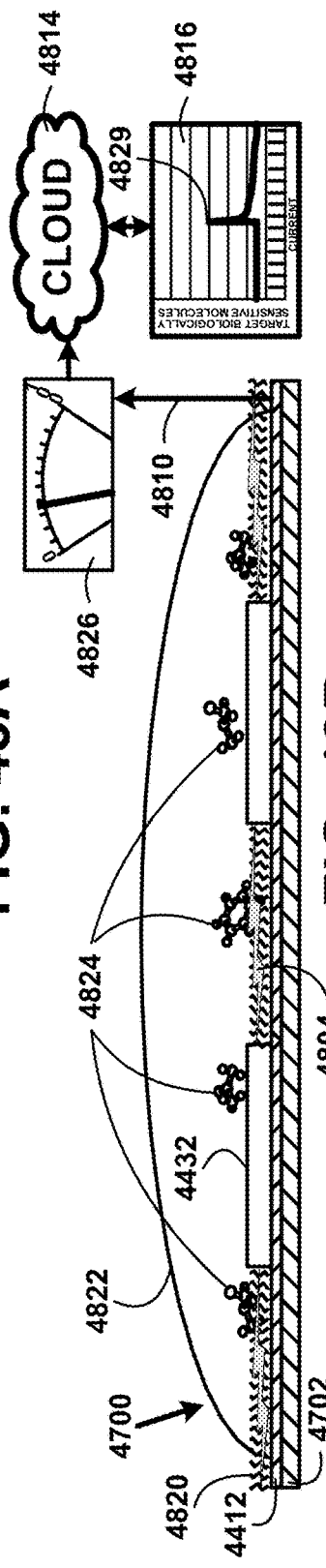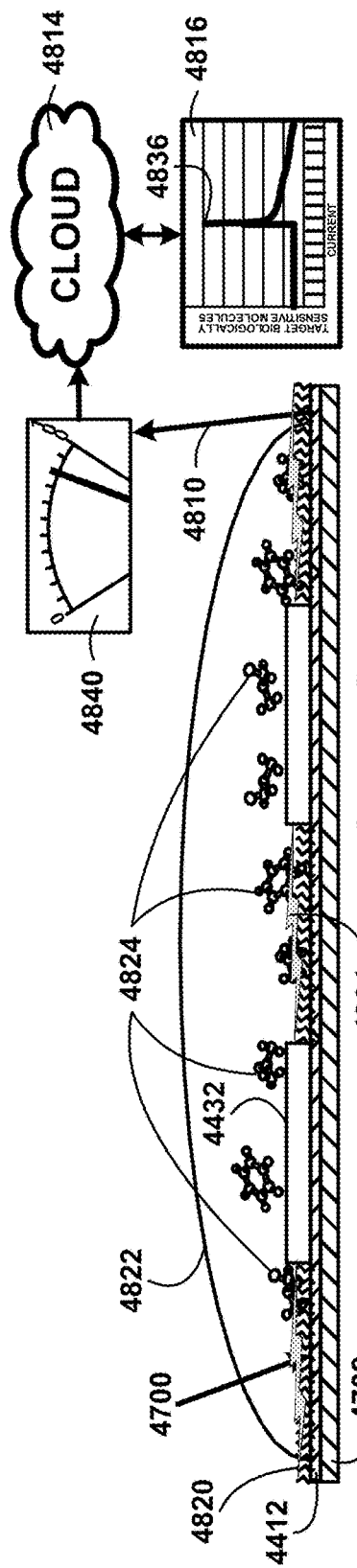

```
                                                              5400
┌─────────────────────────────────────────────────────────────┐
│  PROCESS FOR CHEMICAL AND PATHOGEN DETECTION IN AIR         │
│                  SAMPLE AND HVAC                            │
│  ┌───────────────────────────────────────────────────┐  5410│
│  │  AIR SAMPLE COLLECTED AND ELECTRICALLY CHANGED    │      │
│  │          (USUALLY NEGATIVELY CHARGED)             │      │
│  └───────────────────────────────────────────────────┘      │
│                          ↓                              5420│
│  ┌───────────────────────────────────────────────────┐      │
│  │  NEBULIZER CONTAINING SOLUTION (BUFFER OR OTHER   │      │
│  │  SOLUTIONS) CREATES ELECTRICALLY CHARGED (USUALLY │      │
│  │          POSITIVELY CHARGED) AEROSOLS             │      │
│  └───────────────────────────────────────────────────┘      │
│                          ↓                              5430│
│  ┌───────────────────────────────────────────────────┐      │
│  │  THE NEGATIVELY CHARGED AIR SAMPLE IS ATTRACTED   │      │
│  │  TO THE POSITIVELY CHARGED AEROSOLS FORMING A     │      │
│  │         UNIFORM AEROSOLIZED TEST SAMPLE           │      │
│  └───────────────────────────────────────────────────┘      │
│                          ↓                              5440│
│  ┌───────────────────────────────────────────────────┐      │
│  │  THE AEROSOLIZED TEST SAMPLE IS TRANSFORMED INTO  │      │
│  │  A LIQUID TEST SAMPLE USING AN IMPACTOR JET       │      │
│  │  NOZZLE TO SPRAY THE AEROSOLIZED SAMPLE INTO AN   │      │
│  │  IMPACTION PLATE, WHICH CAUSES THE SAMPLE TO      │      │
│  │  TRANSFORM INTO A LIQUID                          │      │
│  └───────────────────────────────────────────────────┘      │
│                          ↓                                  │
│  ┌───────────────────────────────────────────────────┐      │
│  │  THE LIQUID TEST SAMPLE IS CAPTURED BY A          │      │
│  │  TEMPERATURE CONTROLLED FLUIDIC PATH OR CHAMBER   │  5450│
│  │  WHERE THE LIQUID SAMPLE CAN BE ELECTRICALLY      │      │
│  │  CHARGED AGAIN IF NECESSARY                       │      │
│  └───────────────────────────────────────────────────┘      │
│                          ↓                                  │
│  ┌───────────────────────────────────────────────────┐      │
│  │  THE LIQUID TEST SAMPLE IS PRESENTED TO THE       │  5460│
│  │  SENSOR ARRAY FOR MEASUREMENT THROUGH THE         │      │
│  │  TEMPERATURE CONTROLLED FLUIDIC PATH OR CHAMBER   │      │
│  └───────────────────────────────────────────────────┘      │
│                          ↓                                  │
│  ┌───────────────────────────────────────────────────┐      │
│  │  THE TEST SAMPLE IS DISPOSED IN A WASTE RESERVOIR │  5470│
│  │  USING VARIOUS ACTIVE OR PASSIVE INDUCTION        │      │
│  │  DEVICES SUCH AS VACUUMS OR PUMPS                 │      │
│  └───────────────────────────────────────────────────┘      │
└─────────────────────────────────────────────────────────────┘
```

FIG. 54

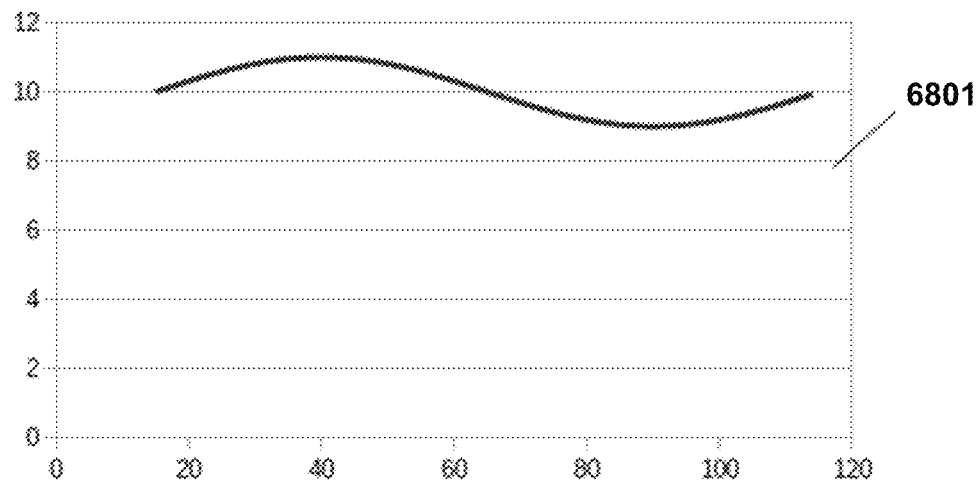
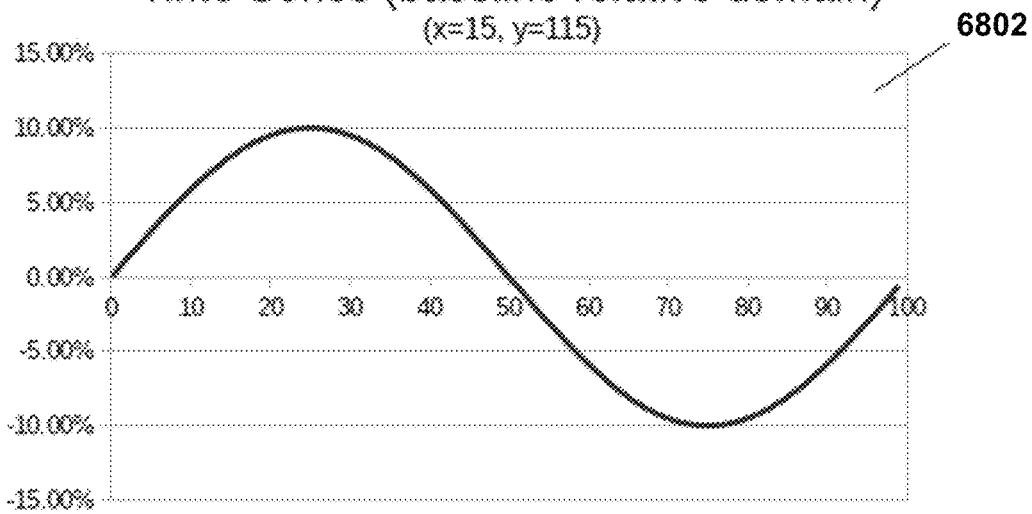
FIG. 66 minValWindow, maxValWindow
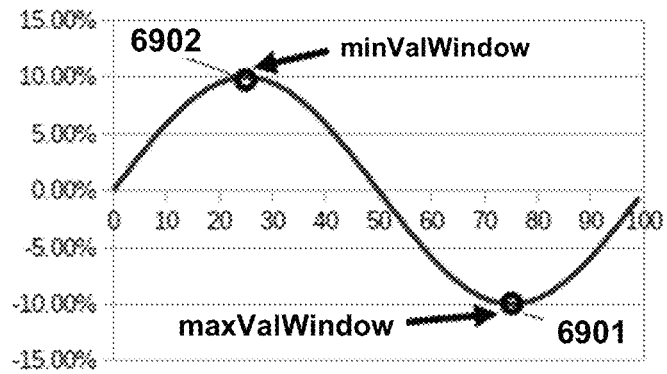
averageOverWindow, areaUnderWindow
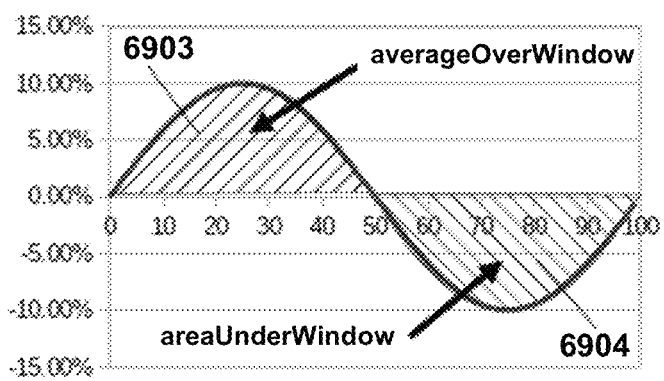
averageOverWindow
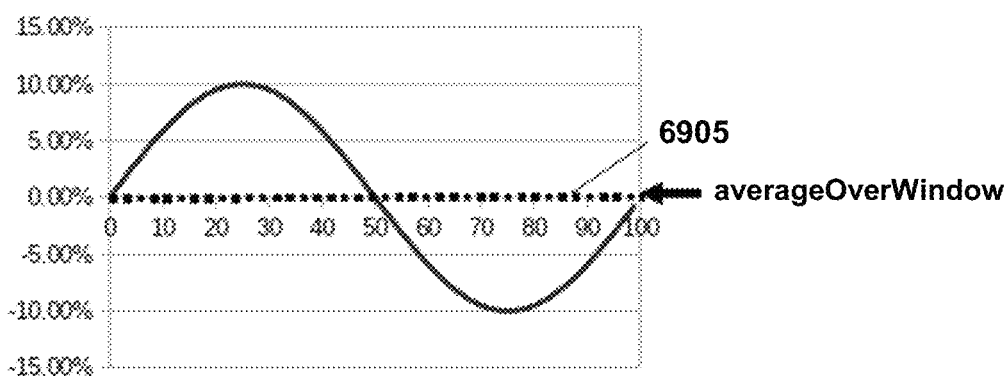
FIG. 67

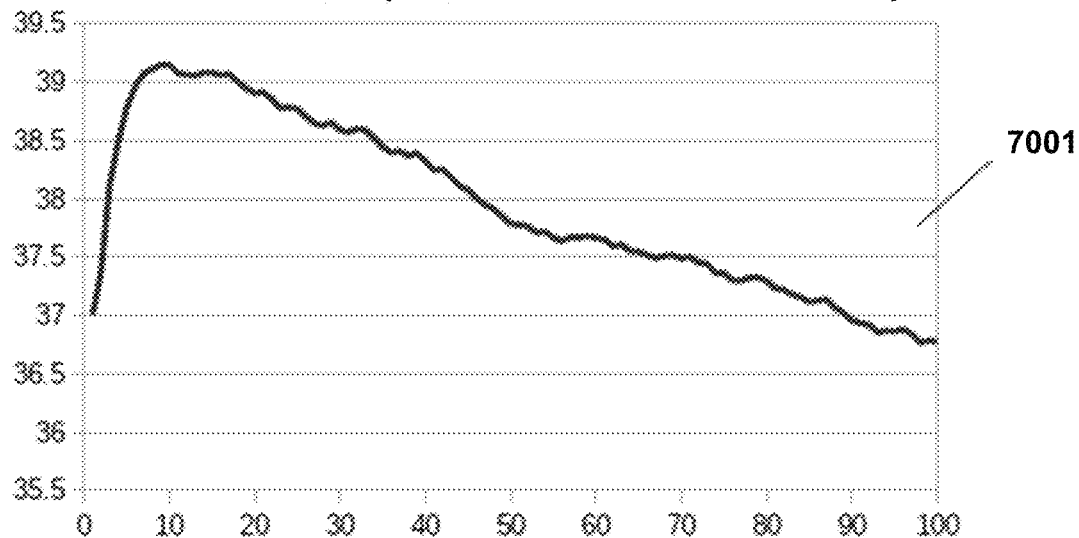
FIG. 68

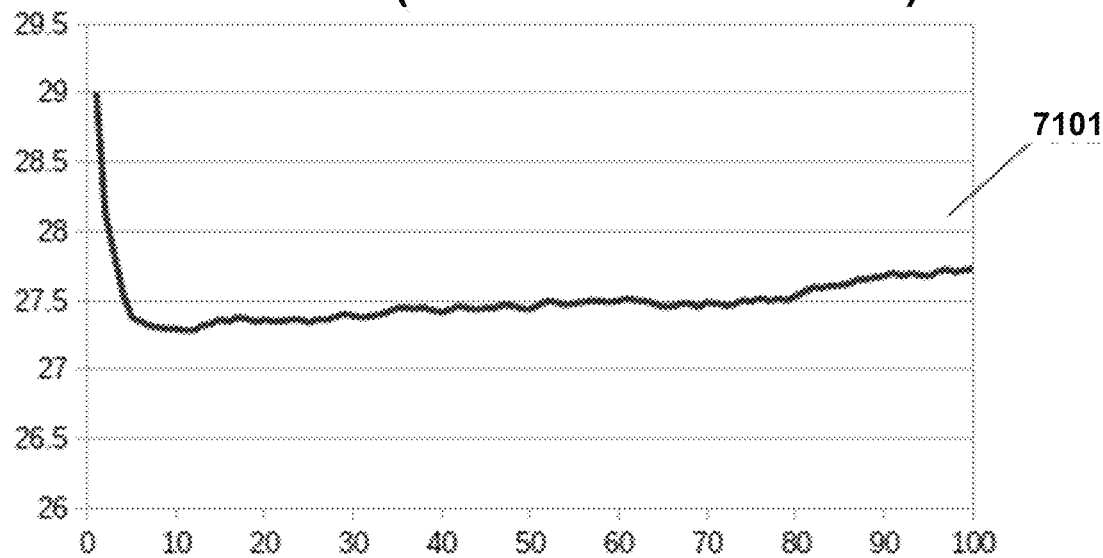
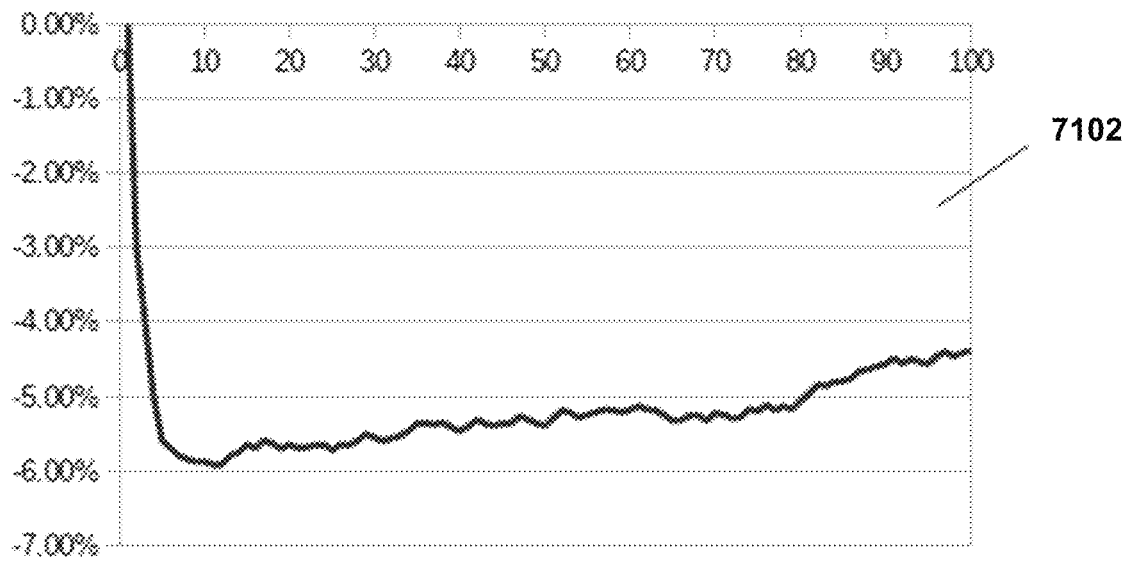
FIG. 69

DEVICE FOR READING, PROCESSING AND TRANSMITTING TEST RESULT DATA FOR PATHOGENS OR VIRUSES IN FLUID TEST SAMPLES

CROSS-REFERENCE TO RELATED APPLICATIONS

This Patent Application is a Continuation-in-part and claims priority to the United States Patent Application entitled: "METHOD AND DEVICES FOR DETECTING VIRUSES AND BACTERIAL PATHOGENS", U.S. Ser. No. 17/324,085 filed on May 18, 2021 by Matthew Hummer, the U.S. Patent Application being incorporated herein by reference.

BACKGROUND

The Covid-19 pandemic has made apparent a need for rapid and accurate detection of for early treatment and analysis of the rate of spreading of the infections. The rapid and accurate detection of infection is also needed for other known infectious viruses and bacterial pathogens and new infectious viruses and bacterial pathogens that may appear. Initial testing was slow and confined to a small number of laboratories using processes that in many cases took days to complete. What is needed for rapid detection for treatment and to collect ample data to locate and measure the rates of infection is a broader range of application venue availability outside of laboratories and a range of training needed to perform the detection testing.

BRIEF DESCRIPTION OF THE DRAWINGS

FIG. 100 shows for illustrative purposes only an example of a printed temperature control device and printed sensor of one embodiment.

Figure 16:
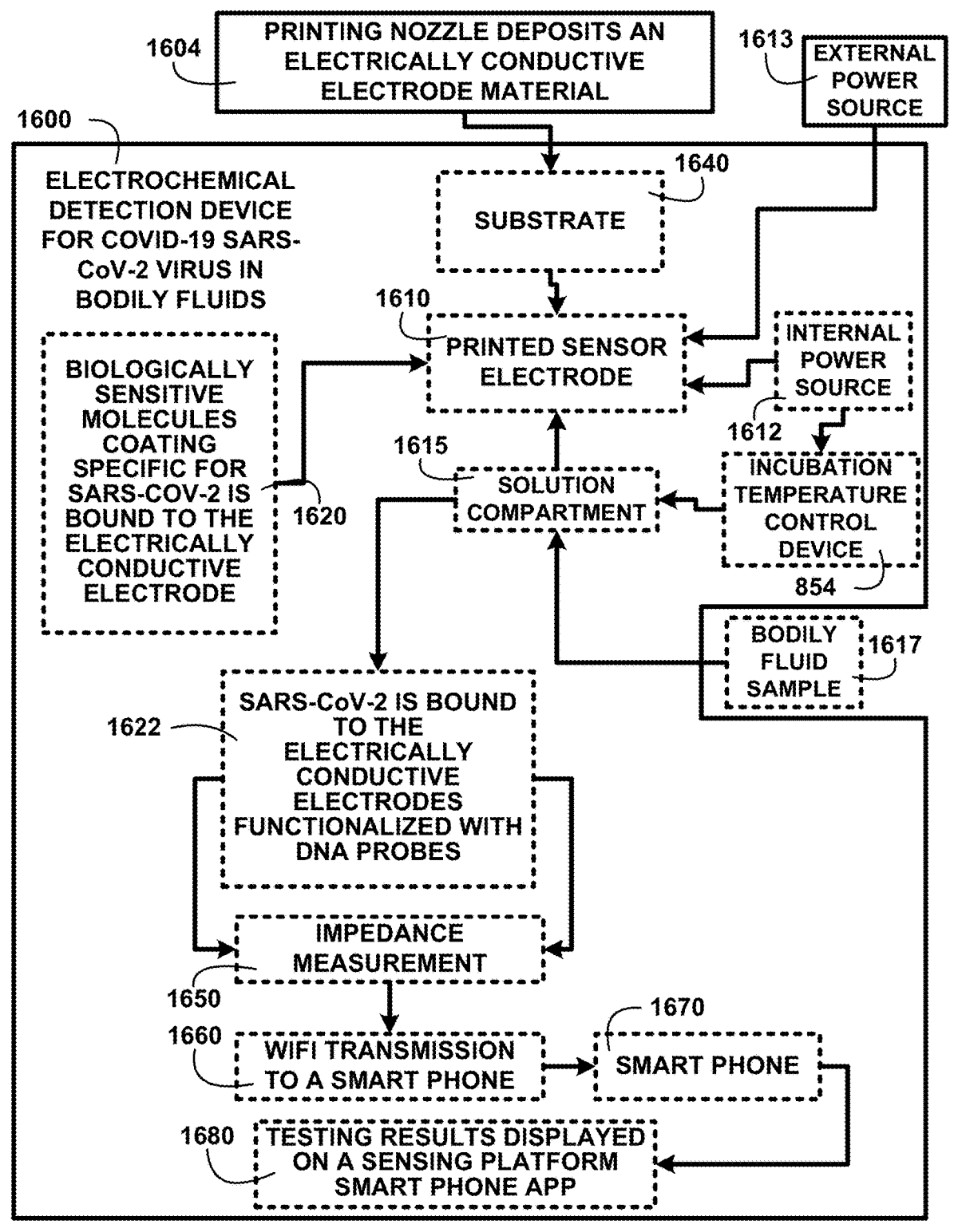

FIG. 16 shows a block diagram of an overview of an example of electrode binding of targeted biologically sensitive molecules and bacterial pathogens of one embodiment.

FIG. 34 shows a block diagram of an overview of communication circuitry to broadcast an alert of one embodiment.

FIG. 42B shows for illustrative purposes only an example of biologically sensitive molecules complementary pairing of one embodiment.

Figures 47A, 47B:
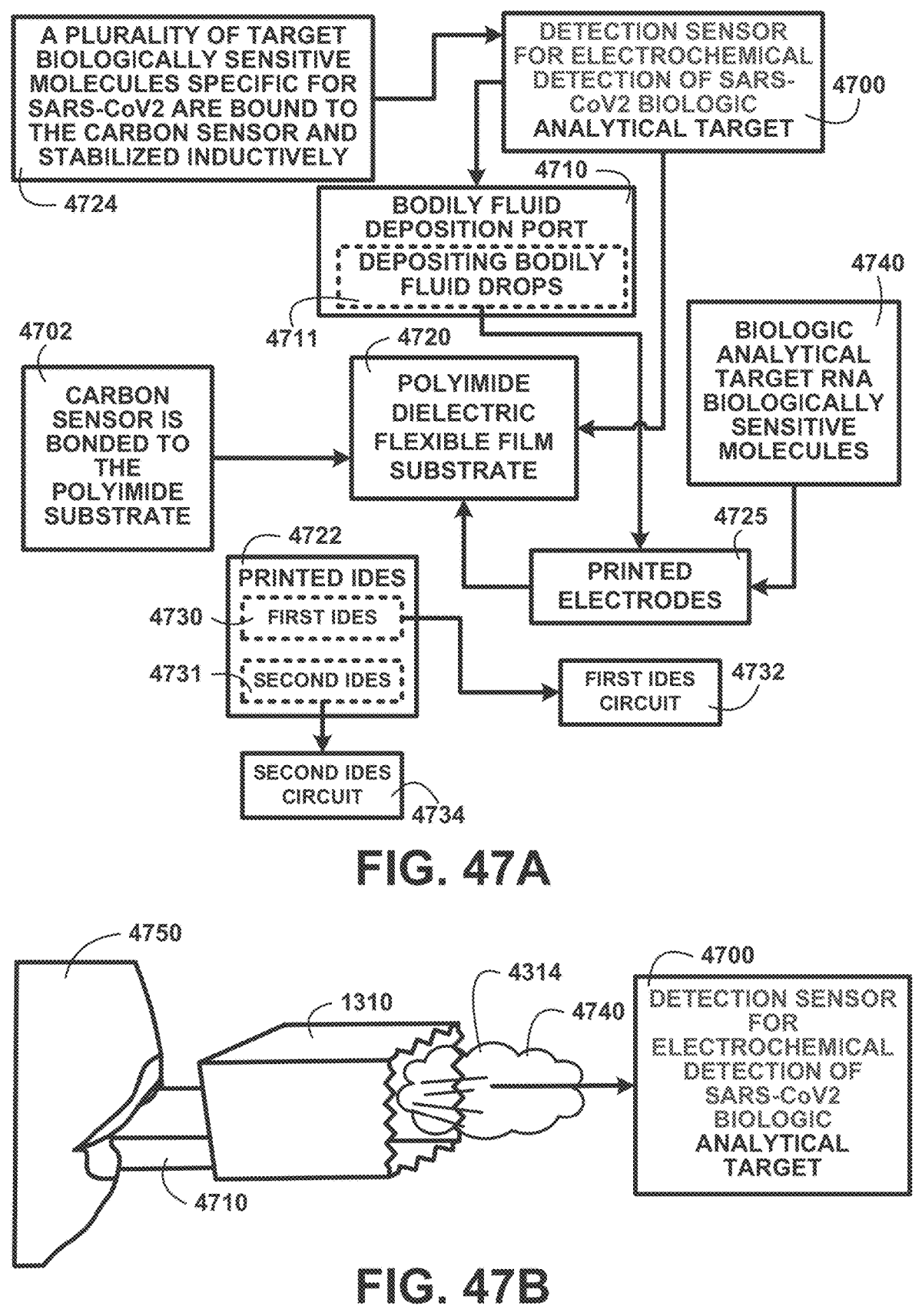

FIG. 47A shows for illustrative purposes only an example of electrochemical detection of SARS-CoV-2 biologic analytical target of one embodiment.

FIG. 47B shows for illustrative purposes only an example of breath moisture test sampling of one embodiment.

FIG. 48A shows for illustrative purposes only an example of a no test sample impedance measurement of one embodiment.

FIG. 48B shows for illustrative purposes only an example of a test sample with low biologic target concentration impedance measurement of one embodiment.

FIG. 48C shows for illustrative purposes only an example of a test sample with high biologic target concentration impedance measurement of one embodiment.

FIG. 54 shows a block diagram of an overview of chemical and pathogen detection in an air sample and HVAC system of one embodiment.

FIG. 66 shows for illustrative purposes only an example of time series (measurement domain) of one embodiment.

FIG. 67 shows for illustrative purposes only an example of maximum relative value of one embodiment.

FIG. 68 shows for illustrative purposes only an example of a positive reading test of one embodiment.

FIG. 69 shows for illustrative purposes only an example of a negative reading test of one embodiment.

DETAILED DESCRIPTION OF THE INVENTION

In the following description, reference is made to the accompanying drawings, which form a part hereof, and in which is shown by way of illustration a specific example in which the invention may be practiced. It is to be understood that other embodiments may be utilized and structural changes may be made without departing from the scope of the present invention.

General Overview:

It should be noted that the descriptions that follow, for example, in terms of a method and devices for detecting viruses and bacterial pathogens are described for illustrative purposes and the underlying system can apply to any number and multiple types of viruses and bacterial pathogens. In one embodiment of the present invention, the method and devices for detecting viruses and bacterial pathogens can be configured using one or both internal and external power sources. The method and devices for detecting viruses and bacterial pathogens can be configured to include a single electrochemical sensing platform device and can be configured to include multiple electrochemical sensing platform devices using the present invention.

The following terms and phrases immobilized, stabilized inductively, polarized, conductively oriented, electrokinetically oriented, and inductively aligned are used herein interchangeably without any change in meaning.

Figure 1:
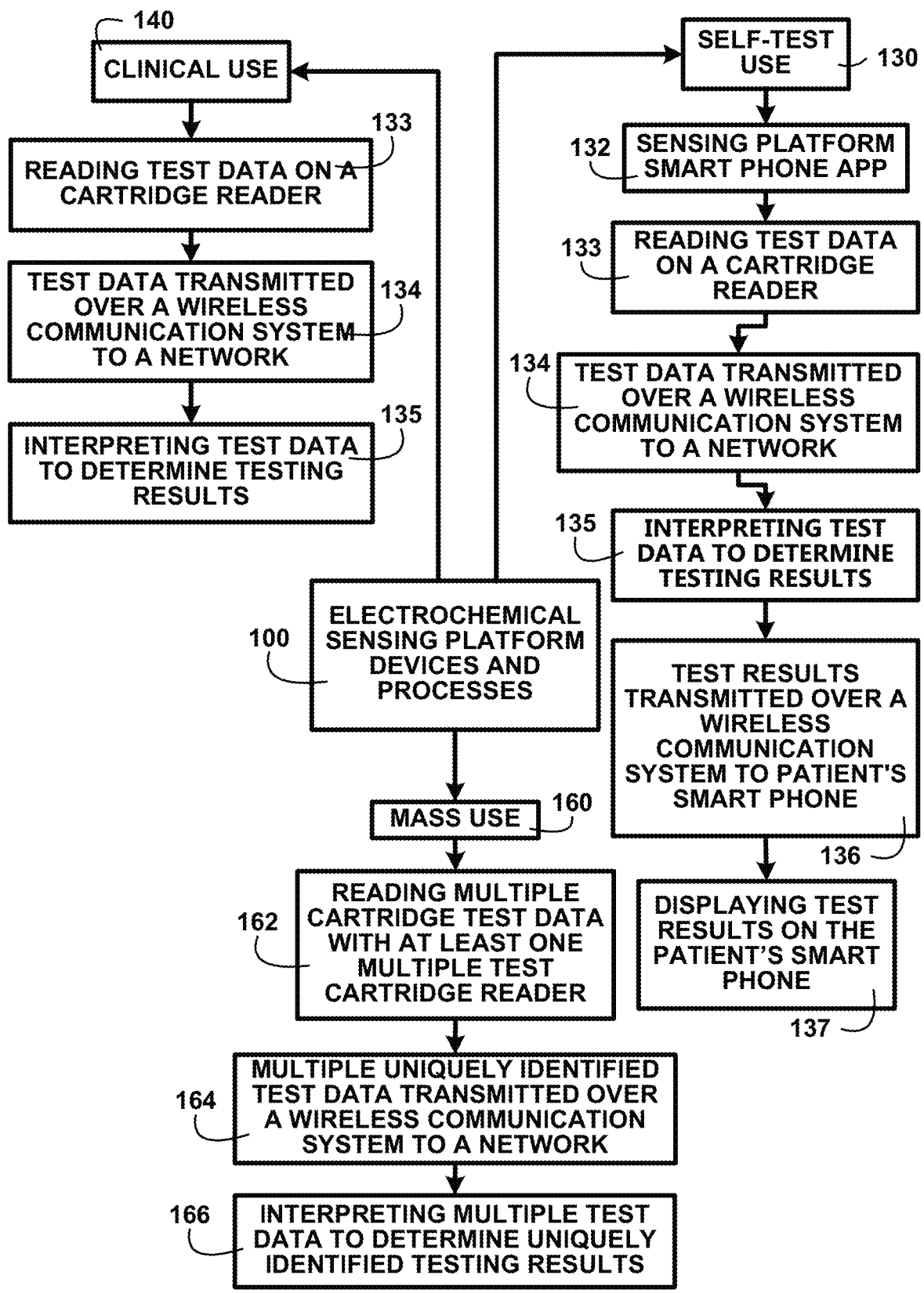
FIG. 1 shows a block diagram of an overview of a method and devices for detecting viruses and bacterial pathogens of one embodiment.

FIG. 1 shows a block diagram of an overview of a method and devices for detecting viruses and bacterial pathogens of one embodiment. FIG. 1 shows electrochemical sensing platform devices and processes 100. The electrochemical sensing platform devices and processes 100 include testing protocol controls for example but not limited to the SARS-CoV-2 virus that causes Covid-19, MRSA, other viruses, and bacteria and pathogens on food. In one embodiment the electrochemical sensing platform devices and processes 100 are configured for self-testing use 130. The electrochemical sensing platform devices and processes 100 configured for self-test use 130 performs recording and reading of testing data and remote interpretation of the test data. The self-test use 130 patient may view the test results transmitted from the remote interpretation means using a sensing platform smartphone app 132 downloaded to the patient's digital device for example a smartphone. In one embodiment the electrochemical sensing platform devices and processes 100 are configured for self-test use 130. The self-test use 130 is processed with reading test data on a cartridge reader 133. The test data is transmitted over a wireless communication system to a network 134. The network is used for interpreting test data to determine testing results 135. Test results are transmitted over a wireless communication system to the patient's smartphone 136 for displaying test results on the patient's smartphone 137 of one embodiment.

In another embodiment, the electrochemical sensing platform devices and processes 100 are configured for clinical use 140. The test data is processed for reading test data on a cartridge reader 133. Clinical use 140 test data is transmitted over a wireless communication system to a network 134 and is stored on a database. The network processes interpreting test data to determine testing results 135. The testing results are reported to a clinician and attending physician of one embodiment. Test results transmitted over a wireless communication system to a patient's smartphone 136 and displaying test results on the patient's smartphone 137.

In yet another embodiment, the electrochemical sensing platform devices and processes 100 are configured for mass use 160. Mass use 160 includes reading multiple cartridge test data with at least one multiple test cartridge reader 162. The multiple uniquely identified test data transmitted over a wireless communication system to a network 164 is recorded on at least one database. The network processes interpreting multiple test data to determine uniquely identified testing results 166. The uniquely identified testing results are reported to a clinician and attending physician of one embodiment.

DETAILED DESCRIPTION

Figure 2A:
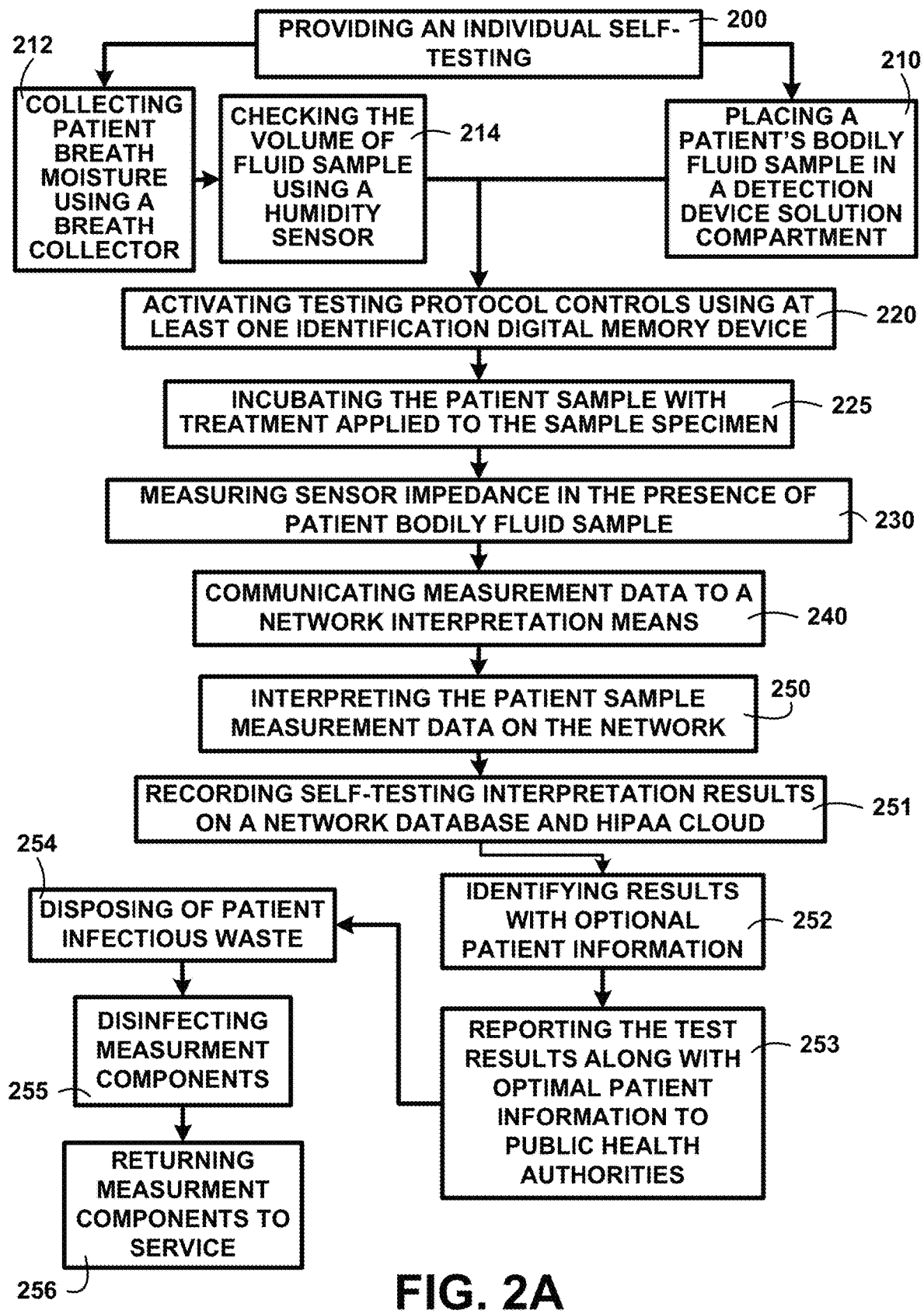
FIG. 2A shows a block diagram of an overview flow chart of an individual self-testing at the home of one embodiment.

FIG. 2A shows a block diagram of an overview flow chart of an individual self-testing at the home of one embodiment. FIG. 2A shows self-testing by an individual at home 200. Testing an individual at home 200 includes placing a patient's bodily fluid sample in a detection device solution compartment 210. A patient's bodily fluid sample may consist of any one of a group of saliva, sputum, nasal mucus, blood; breathe moisture, or other fluid from a human body. In another embodiment, a sample is obtained by collecting patient breath moisture using a breath collector 212. The breath collector includes for example a process of checking the volume of the fluid sample using a humidity sensor 214 of one embodiment.

Data Flow for Self-Testing Process:

Federal law requires any test for infectious disease has to be reported to local and state health officials then to Federal agencies like CDC which is part of HHS. cdc.gov/coronavirus/2019-ncov/lab/reporting-lab-data. Infectious disease test results in the reporting transmission required data fields. Laboratories should make every reasonable effort to provide the following data elements to state and jurisdictional health departments. The test ordered—use harmonized LOINC codes provided by CDC, Device Identifier, Test result—use appropriate LOINC and SNOMED codes, as defined by the Laboratory In Vitro Diagnostics (LIVD) Test Code Mapping for SARS-CoV-2 Tests provided by CDC, Test Result date (date format), Accession #/Specimen ID, Patient age, Patient race, Patient ethnicity, Patient sex, Patient residence zip code, Patient residence county, Ordering provider name and nonpharmaceutical interventions (as applicable), Ordering provider zip code, Performing facility name and CLIA number, Performing facility zip code, Specimen Source—use appropriate LOINC, SNOMED-CT, or SPM4 codes, or equivalently detailed alternative codes, Date test ordered (date format), and Date specimen collected (date format).

The following additional demographic data elements should also be collected and reported to state or local public health departments: Patient name (Last name, First name, Middle Initial), Patient street address, Patient phone number with area code, Patient date of birth, Ordering provider address, and Ordering provider phone number.

To protect patient privacy, any data that state and jurisdictional health departments send to CDC will be de-identified and will not include some patient-level information. The de-identified data shared with CDC will contribute to understanding COVID-19's impact, case rate positivity trends, testing coverage, and will help identify supply chain issues for reagents and other materials.

The electrochemical sensing platform devices and processes 100 of FIG. 1 are configured for detecting any number and multiple types of viruses and bacterial pathogens using impedimetric detection of analytical targets. The electrochemical sensing platform devices and processes 100 of FIG. 1 include activating testing protocol controls using at least one identification digital memory device 220 for example but not limited to the SARS-CoV-2 virus that causes Covid-19, MRSA, other viruses, and bacteria and pathogens on food. In one embodiment, the electrochemical sensing platform devices and processes 100 of FIG. 1 include incubating the patient sample with heat applied to the sample specimen 225. Heated incubation processing prepares the testing for measuring sensor impedance in the presence of patient bodily fluid sample 230. Heated incubation processing prepares the testing for blood, serum, and other test samples for measuring impedance. There are at least three ways of treating the patient test sample before testing. The three ways include: 1) heat treatment 2) chemical treatment or 3) treatment with materials. All three treatments are intended to optimize the sample for evaluation. Optimal samples have appropriate levels of volume, viscosity, pH, diluent, and virus RNA biologically sensitive molecules exposure.

The electrochemical sensing platform devices and processes 100 of FIG. 1 include communication devices for communicating measurement data to a network Interpretation means 240. Processing includes interpreting the patient sample measurement data on the network 250. The network interpretation includes recording self-testing interpretation results on a network database and HIPAA cloud 251. In one embodiment recording self-testing interpretation results includes identifying results with optional patient information 252 and reporting the test results along with optimal patient information to public health authorities 253. After the results are determined the processing continues with disposing of patient infectious waste 254, disinfecting measurement components 255, and returning measurement components to service 256 of one embodiment.

Figure 2B:
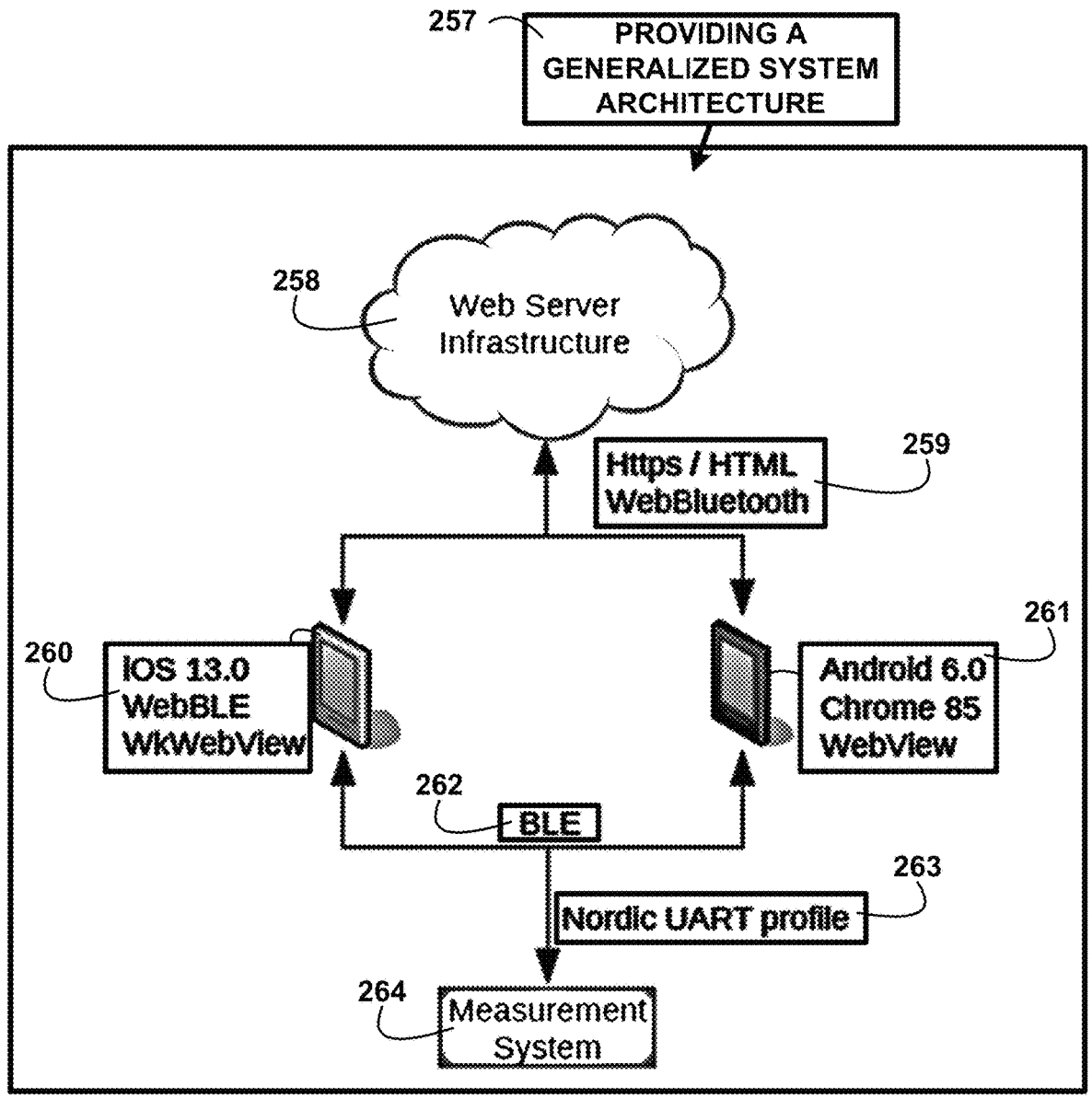
FIG. 2B shows for illustrative purposes only an example of a generalized system infrastructure of one embodiment.

Generalized System Infrastructure:

FIG. 2B shows for illustrative purposes only an example of a generalized system infrastructure of one embodiment. FIG. 2B shows a generalized system infrastructure 257. A generalized system infrastructure 257 includes a Web Server Infrastructure 258. The Web Server Infrastructure 258 supports both the client-facing applets as well as the back-end interpretation, database, and reporting structures. A Web Server Infrastructure 258 includes an HTTPS/HTML Web Bluetooth application programming interface(API) 259. An IOS 13.0 Webble WkWebView 260 supports a viable subset of Web Bluetooth, allowing the server-side to access a BLE device. An Android 6.0 Chrome 85 WebView 261 directly supports Web Bluetooth APIs to allow server-side access to a BLE device. A BLE 262 device, referring to a telecommunication equipment Bluetooth® Low Energy (BLE) device.

Nordic UART profile 263 wherein Nordic UART profile 263 service receives and writes data and serves as a bridge to the Universal Asynchronous Receiver-Transmitter (UART) interface. These devices and services provide data to a measurement system 264. The measurement system 264 accepts a test cassette, executes the stored instructions within the test cassette and provides a feature vector of the measurements of the tests. The smartphone client-side application "app" displays the client-testing information provided by the webserver infrastructure 258 and provides a communication path between the web server infrastructure 258 and the measurement system 264 of one embodiment.

Both iOS ("WKWebView") and Android ("WebView") allow apps to embed web pages in Apps. This approach allows the development of what appears to be an App but is still essentially a web browser. Especially with the iOS-side development, this allows the app to implement the WebBluetooth API and allow operation of one embodiment.

Figure 2C:
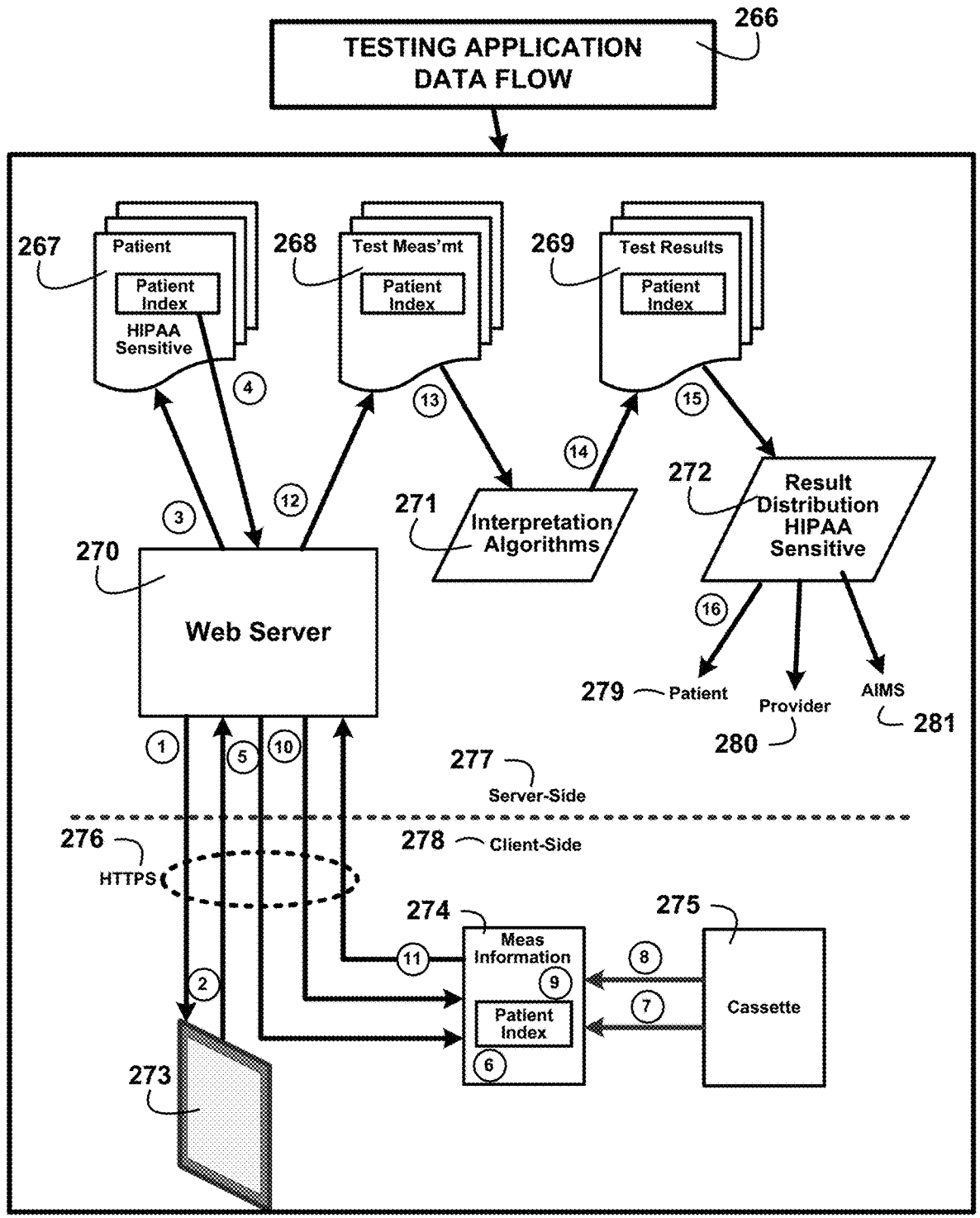
FIG. 2C shows for illustrative purposes only an example of a testing application data flow of one embodiment.

Testing Application Data Flow:

FIG. 2C shows for illustrative purposes only an example of a testing application data flow of one embodiment. FIG. 2C shows a testing application data flow 266. FIG. 2C shows the server side 277 features including a patient HIPAA sensitive patient index 267, test measurement patient index 268, test results patient index 269, web server 270, interpretation algorithms 271, result distribution HIPAA sensitive 272, to patient 279, to provider 280, and to AIMS 281.

FIG. 2C shows processes within the server side 277 including steps 3. Patient record is stored, 3.1 and assigned a new ID Number if a patient doesn't exist, 3.2 recovers an existing ID Number if a patient does already exist in the records, 4. Patient ID Number information is sent through Web Server, 12. Web Server stores "test Record" (linked to patient through Patient Index), 13. Interpretation Algorithms retrieve "test Record" and interprets feature vector(s) to determine test results, 14. Test Results are stored (linked to patient through Patient Index), 15. Results Distribution collects new Test Results and fuses information with Patient record, and 16. Results Distribution sends appropriately formatted results to Patient, Provider, AIMS, and others (as required).

FIG. 2C shows the client-side 278 features including for example a patient tablet 273, measurement information patent index 274, cassette 275, and HTTPS 276. FIG. 2C shows processes within the client side 278 including steps 7. Measurement System retrieves "sensor Platform" information from Cassette, 8. Measurement System executes "protocol" on Cassette and collects measurements, and 9. Measurement System executes "vector" on collected measurements. The client-side application "app" displays the client-facing information provided by the Web Server Infrastructure and provides a communication path between the Web Server Infrastructure 258 of FIG. 2B and the Measurement System 264 of FIG. 2B.

The testing application data flow 266 includes processes between a server-side 277 and a client-side 278. The processes between a server-side 277 and a client-side 278 include steps 1. Web Server provides a form for the patient to fill out on the smartphone, 2. smartphone submits a patient form, 5. Optional step Using Web Bluetooth Send Patient ID Number through the smartphone to Measurement System (Reader), 6. Patient ID Number is stored locally on Measurement System, 10. Optional step Using Web Bluetooth, Web Sewer periodically polls Measurement System for test completed, 11. Using Web Bluetooth, Web Server retrieves "test Record" from Measurement System upon completion.

The Measurement System accepts a Test Cassette, executes the stored instructions within the Test Cassette, and provides a feature vector of the measurements of the tests. The "test Record" from the measurement system is also sent to BLE 262 of FIG. 2B device using a cookie of one embodiment.

Figure 3:
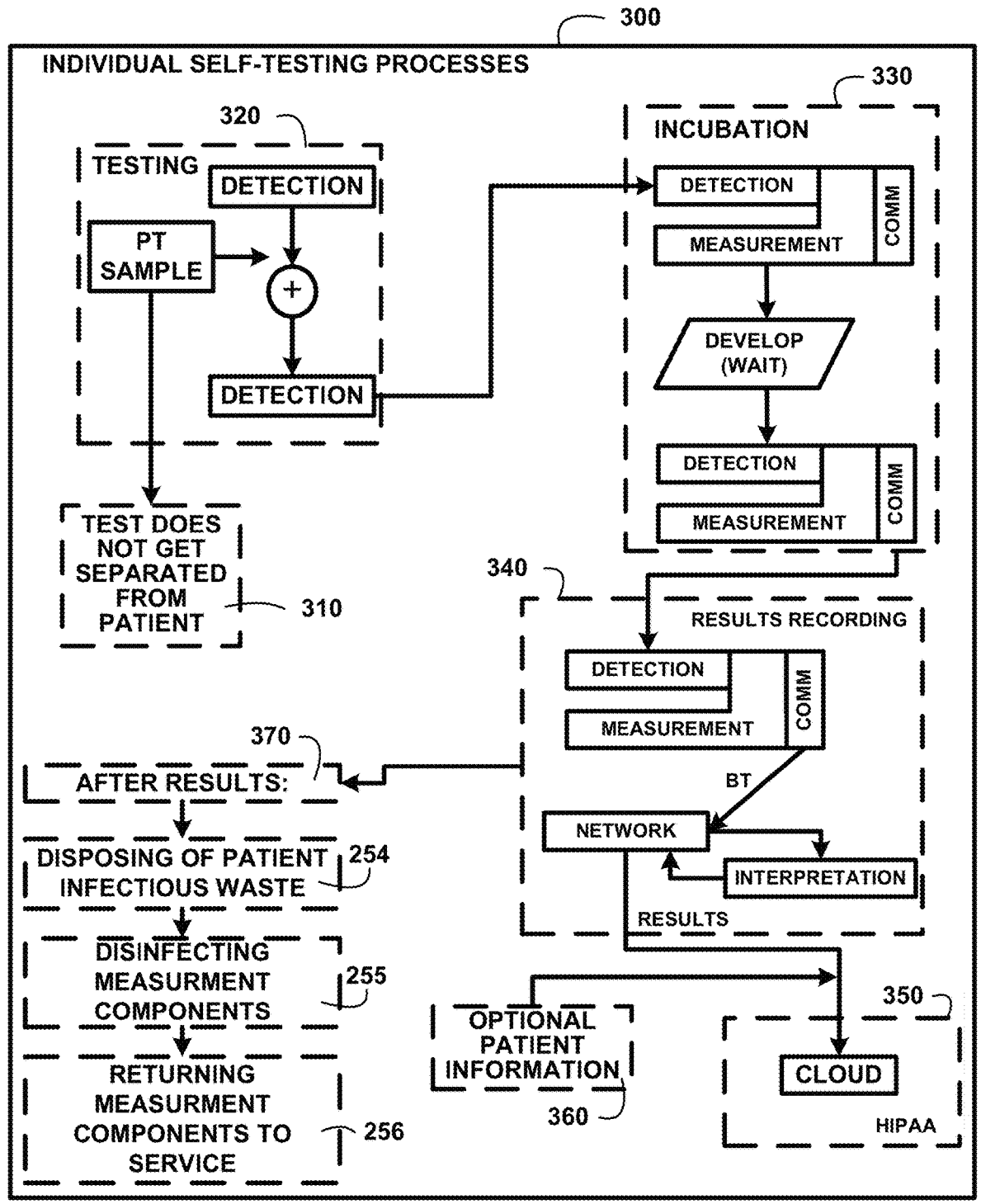
FIG. 3 shows for illustrative purposes only an example of an individual self-testing process of one embodiment.

An Individual Self-Testing Process:

FIG. 3 shows for illustrative purposes only an example of an individual self-testing process of one embodiment. FIG. 3 shows individual self-testing processes 300. The test does not get separated from patient 310. The testing 320 processes include detection prior to placing the patient sample to confirm a clear base. Upon placing the patient sample the detection process continues.

A second detection process is conducted and measurement of any changes in the impedance of the detection electrode. In one example the patient sample is processed with incubation 330. A comm device is used to transmit the multiple detection measurements to the sensing platform smartphone app 132 of FIG. 1 or other means for reading and interpreting test data. During incubation, the patient sample is heated over a predetermined time period and at a predetermined heat level then cooled over a predetermined time period and at a predetermined cooling level to develop the patient sample. Other methods of sample preparation could be used including chemical treatment and treatment using materials. After the development period, another detection measurement is processed and transmitted over comm.

The results recording 340 will include the detection and measurement. The comm will transmit the detection and measurement data for BT interpretation on the network means for reading and interpreting test data. The results of the test for infectious disease will also be transmitted to a HIPAA cloud 350, to local and state health officials then to Federal agencies like CDC. The results reporting will include all agency required data and include optional patient information 360. After results: 370 have been recorded, devices for detection are disposed of (infectious waste) 372, measurement components are disinfected 374, and measurement device is returned to service 376 of one embodiment.

Figure 4:
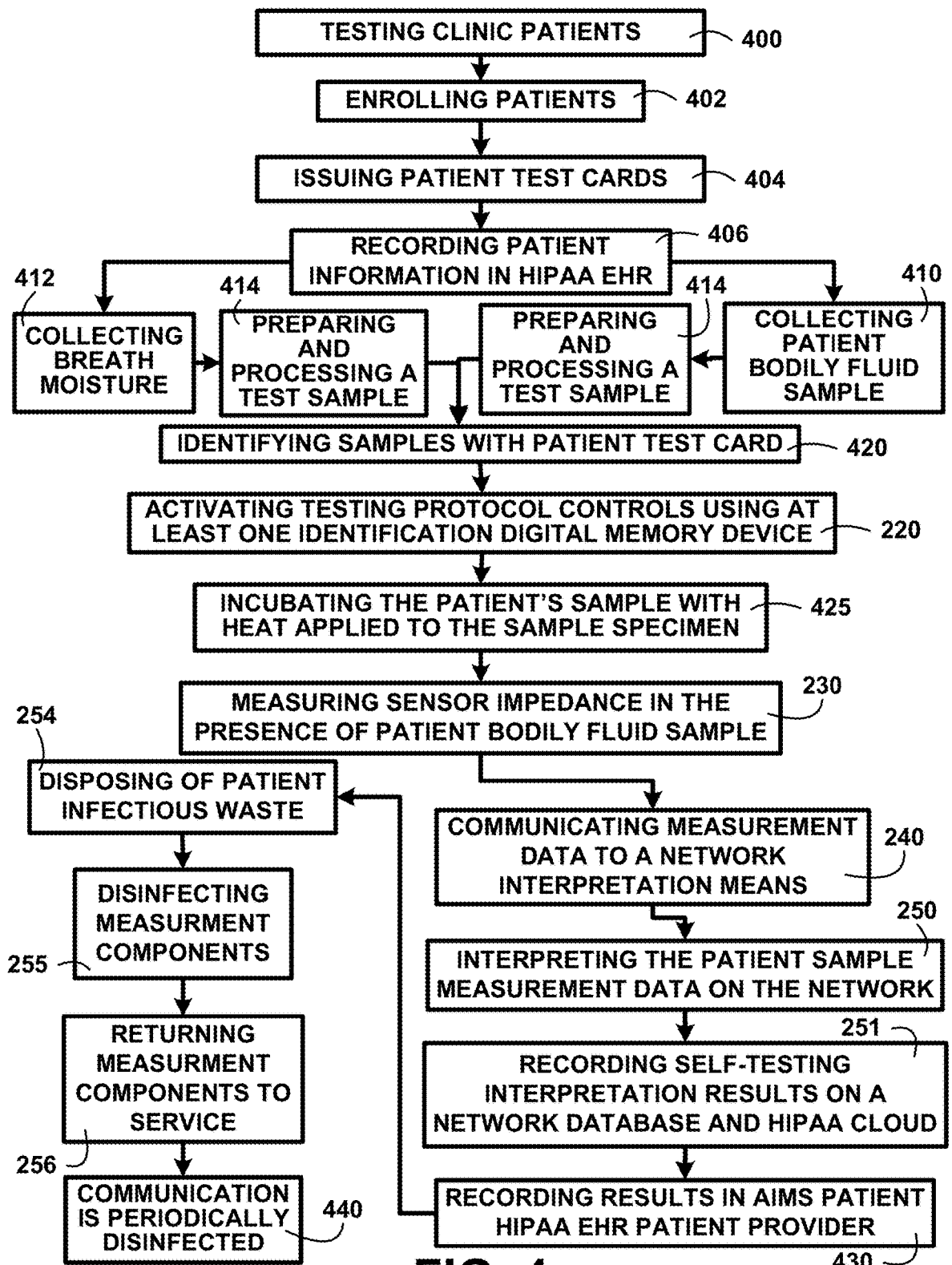
FIG. 4 shows a block diagram of an overview flow chart of testing clinic patients of one embodiment.

Testing Clinic Patients:

FIG. 4 shows a block diagram of an overview flow chart of testing clinic patients of one embodiment. FIG. 4 shows testing clinic patients 400 processing. Testing clinic patients 400 processing begins with enrolling patients 402 and issuing patient test cards 404. The patient test cards include a unique identifying code and patient information. The processing continues with recording patient information in HIPAA EHR 406.

Collecting patient bodily fluid sample 410 for preparing and processing a test sample 414. In another embodiment, a patient sample includes collecting breath moisture 412 and preparing and processing a test sample 414 including checking the volume of breath fluid sample for a sufficient sample specimen and may require additional patient exhalations into the device. The process includes identifying samples with patient test card 420. The testing process is prepared with activating testing protocol controls using at least one identification digital memory device 220.

The processing proceeds with incubating the patient's sample with various types of treatment including heat applied to the sample specimen 425 or chemicals applied to the sample specimen or materials applied to the sample specimen. When incubation is completed the process continues with measuring sensor impedance in the presence of patient bodily fluid sample 230. The impedance of the electrode is affected by the presence of the incubated patient sample.

Communicating measurement data to an interpretation means 240 for interpreting the patient sample measurements with interpreting the patient sample measurement data on the network 250. The process includes recording testing interpretation results 260 and recording results in a patient HIPAA EHR 430 and to local and state health officials then to Federal agencies like CDC. After the results are recorded the process includes disposing of patient infectious waste 272, disinfecting measurement components 273, returning measurement components to service 274, and communication is periodically disinfected 440 of one embodiment.

Figure 5:
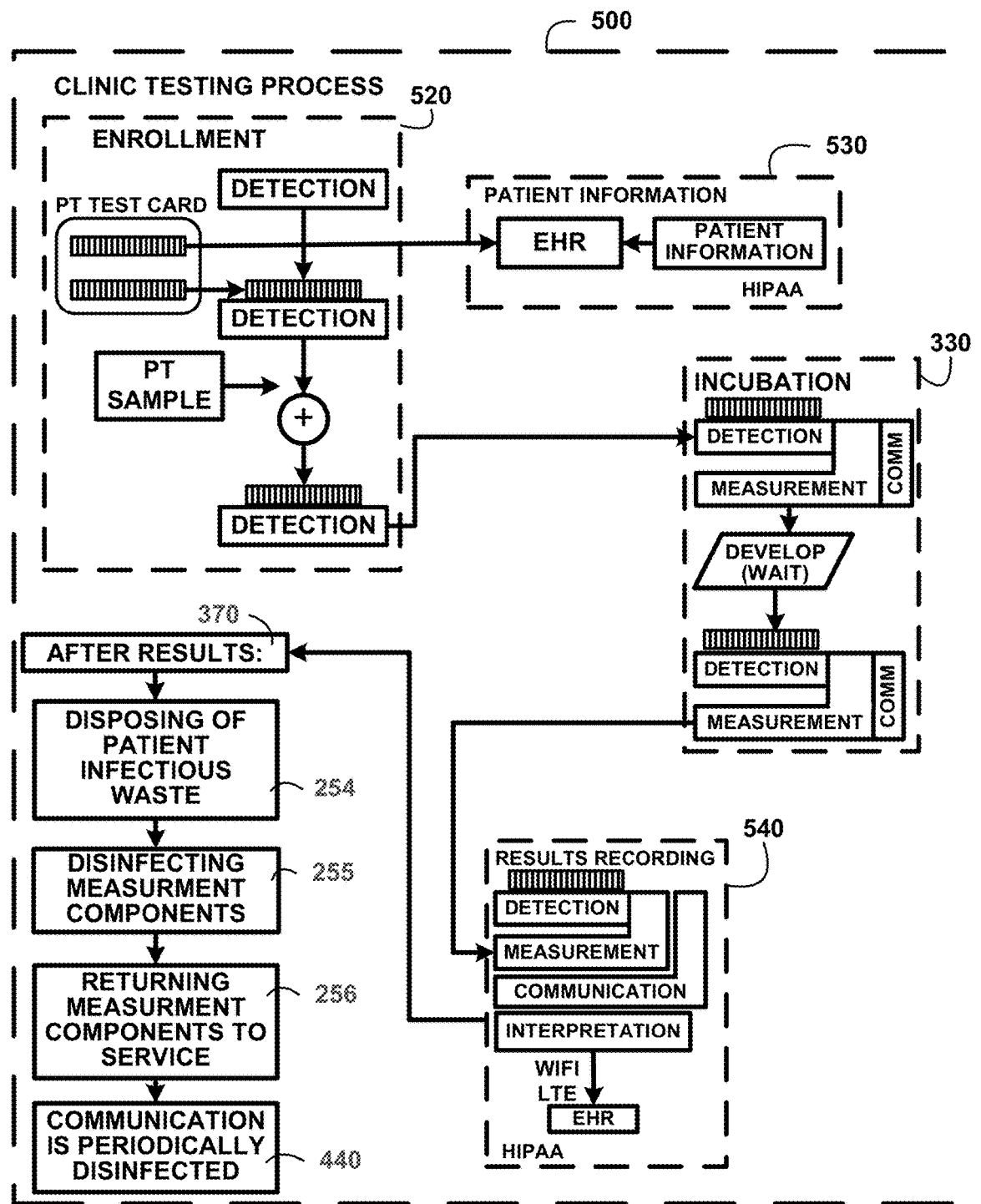
FIG. 5 shows for illustrative purposes only an example of a clinic testing process of one embodiment.

A Clinic Testing Process:

FIG. 5 shows for illustrative purposes only an example of a clinic testing process of one embodiment. FIG. 5 shows a clinic testing process 500 and enrollment 520 of patients being testing and issuing a patient test card. The patient test card assigns a unique identifying testing code and records patient information 530 on the card. The patient card is used for transmitting to the patient EHR the patient information and testing results according to HIPAA. The card can also be a virtual token or scannable such as QR code or another method of verification such as biometric or other.

The process includes detection where the detection with patient ID is first performed prior to placing a patient sample. After placing the patient sample detection with patient ID proceeds to incubation 330 of the patient sample with heat applied to the sample. Other treatments can be used such as chemical treatment or treatment using advanced materials. The detection with patient ID is followed by a measurement of the electrode impedance after a predetermined "develop" time period of the incubated patient sample.

Results recording 540 is performed after the detection with patient ID measurement is transmitted with communication to the interpretation means. The results recording 540 after interpretation is transmitted via WIFI LTE to the patient EHR under HIPAA. After results: 370 are recorded and reported to local and state health officials then to Federal agencies like CDC which is part of HHS, detection is disposed of (infectious waste) 372, measurement is disinfected 374, measurement is returned to service 376, and communication is periodically disinfected 440. Data flow process for clinic testing application is the same as shown in FIG. 2C of one embodiment.

Figure 6:
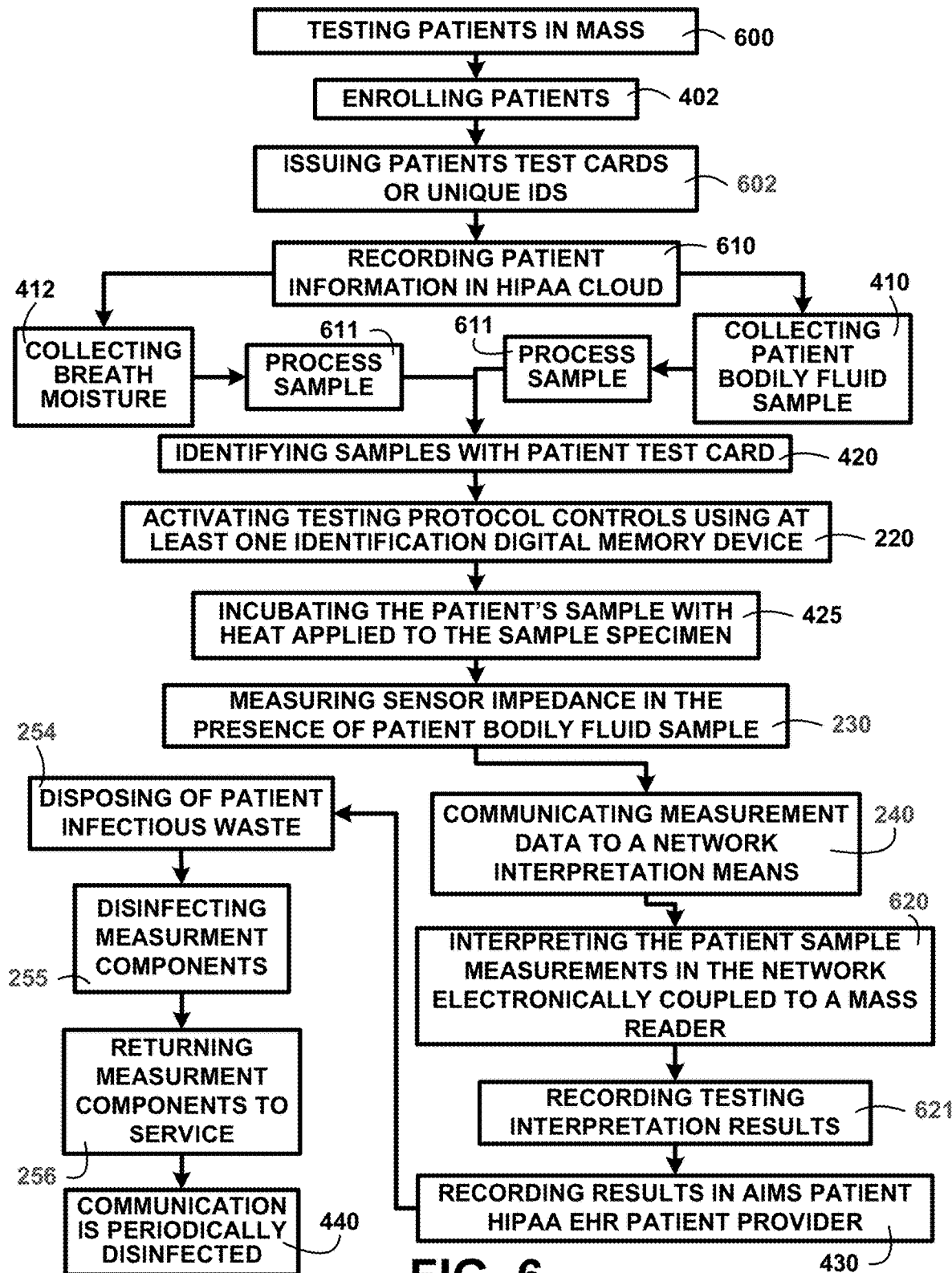
FIG. 6 shows a block diagram of an overview flow chart of testing patients in a mass of one embodiment.

Testing Patients in Mass:

FIG. 6 shows a block diagram of an overview flow chart of testing patients in a mass of one embodiment. FIG. 6 shows testing patients in mass 600 using the electrochemical sensing platform devices and processes 100 of FIG. 1. A process is used for enrolling patients 402 and issuing patients test cards or unique IDs 602. The patient's test cards include a unique testing code and patient information. The processing includes recording patient information on a HIPAA cloud 610.

The processing continues with collecting patient bodily fluid sample 410 process sample 611 testing specimen. In another embodiment, the process is collecting breath moisture 412 process sample 611 from a patient and checking the volume of breath fluid sample 414. Collecting patient samples includes identifying samples with patient test card 420. Processing continues with activating testing protocol controls using at least one identification digital memory device 220. A process is used for incubating the patient's sample with heating and cooling applied to the sample specimen 425.

After incubation, a process is used for measuring sensor impedance in the presence of patient bodily fluid sample 230 of the detection electrode. Processing for communicating measurement data to an interpretation means 240 for interpreting the patient sample measurements in a mass reader 620 and recording testing interpretation results 261.

Recording testing interpretation results 260 includes recording results on a HIPAA cloud 271. After the results are recorded the process continues with disposing of patient infectious waste 272, disinfecting measurement components 273, returning measurement components to service 274, and communication is periodically disinfected 440. Data flow process for clinic testing application is the same as shown in FIG. 2C of one embodiment.

Figure 7:
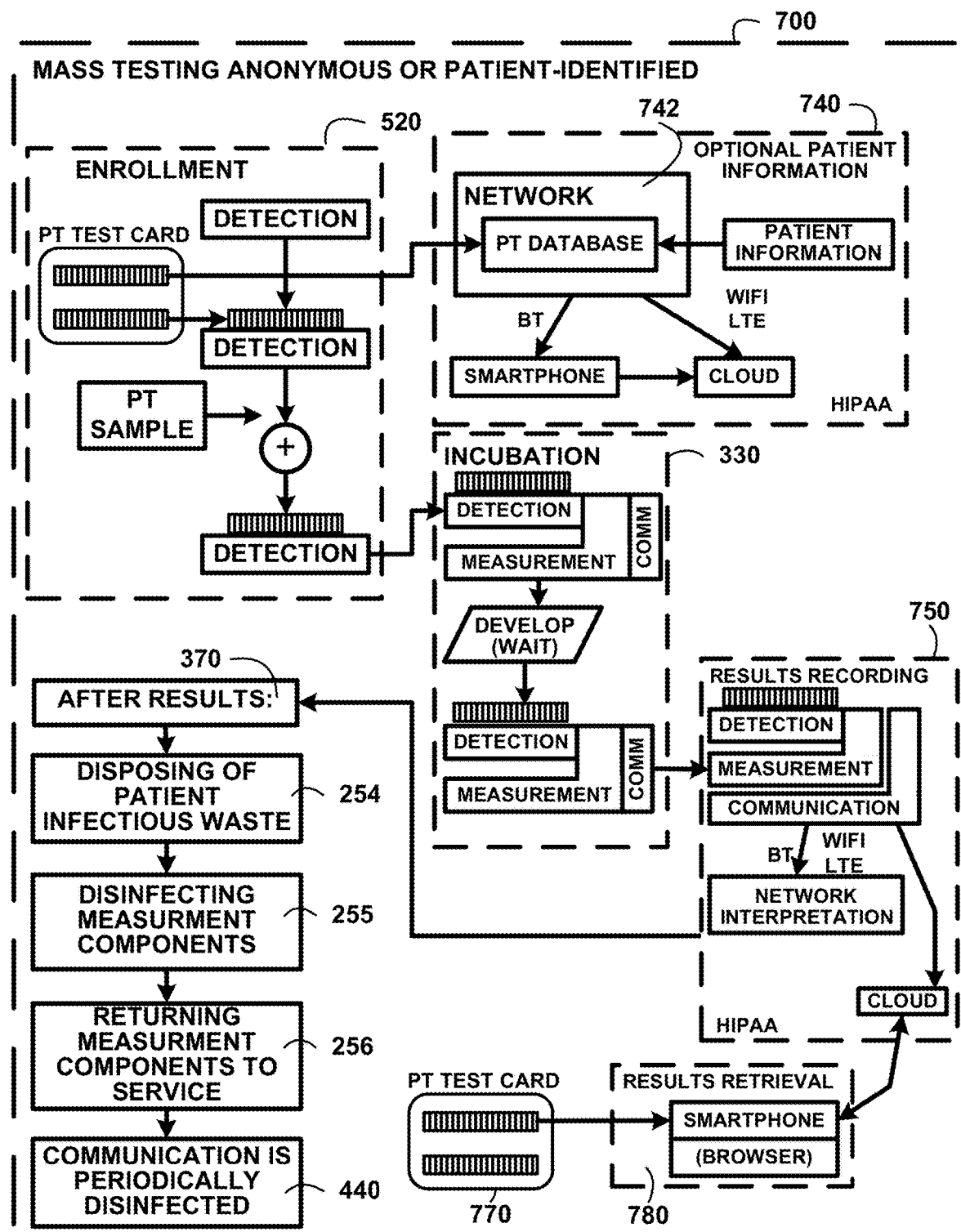
FIG. 7 shows for illustrative purposes only an example of mass testing anonymously or patient-identified of one embodiment.

Mass Testing Anonymously or Patient-Identified:

FIG. 7 shows for illustrative purposes only an example of mass testing anonymously or patient-identified of one embodiment. FIG. 7 shows mass testing anonymously or patient-identified 700. Mass testing processing begins with enrollment 520 of patients and issuing a patient test card to each patient. The patient test card includes optional patient information 740 that may be transmitted to a network 742 and recorded on a patient database. The optional patient information 740 may be transmitted to BT smartphone for accessing patient information transmitted via WIFI LTE to a HIPAA cloud.

Detection with a patient ID labeled patient sample is followed by incubation 330 with applied heat or other test sample treatments to develop for a predetermined time period the patient sample. Detection with a patient ID sample after developing is then processed for measurement of electrode impedance. The detection measurement results recording 750 are communicated using a communication device to an interpretation system for the determination of the concentration of any detected virus or bacterial pathogen.

The interpretation results are transmitted via BT smartphone and WIFI LTE to a patient EHR HIPAA file. A patient test ID card 770 is used by a patient who logs in to a HIPAA cloud for results retrieval 780 using a smartphone/browser. After results: 370 are recorded and reported detection is disposed of (infectious waste) 372, measurement is disinfected 374, measurement is returned to service 376, and communication is periodically disinfected 440. The data flow process for mass-testing is the same as shown in FIG. 2C of one embodiment.

Figure 8:
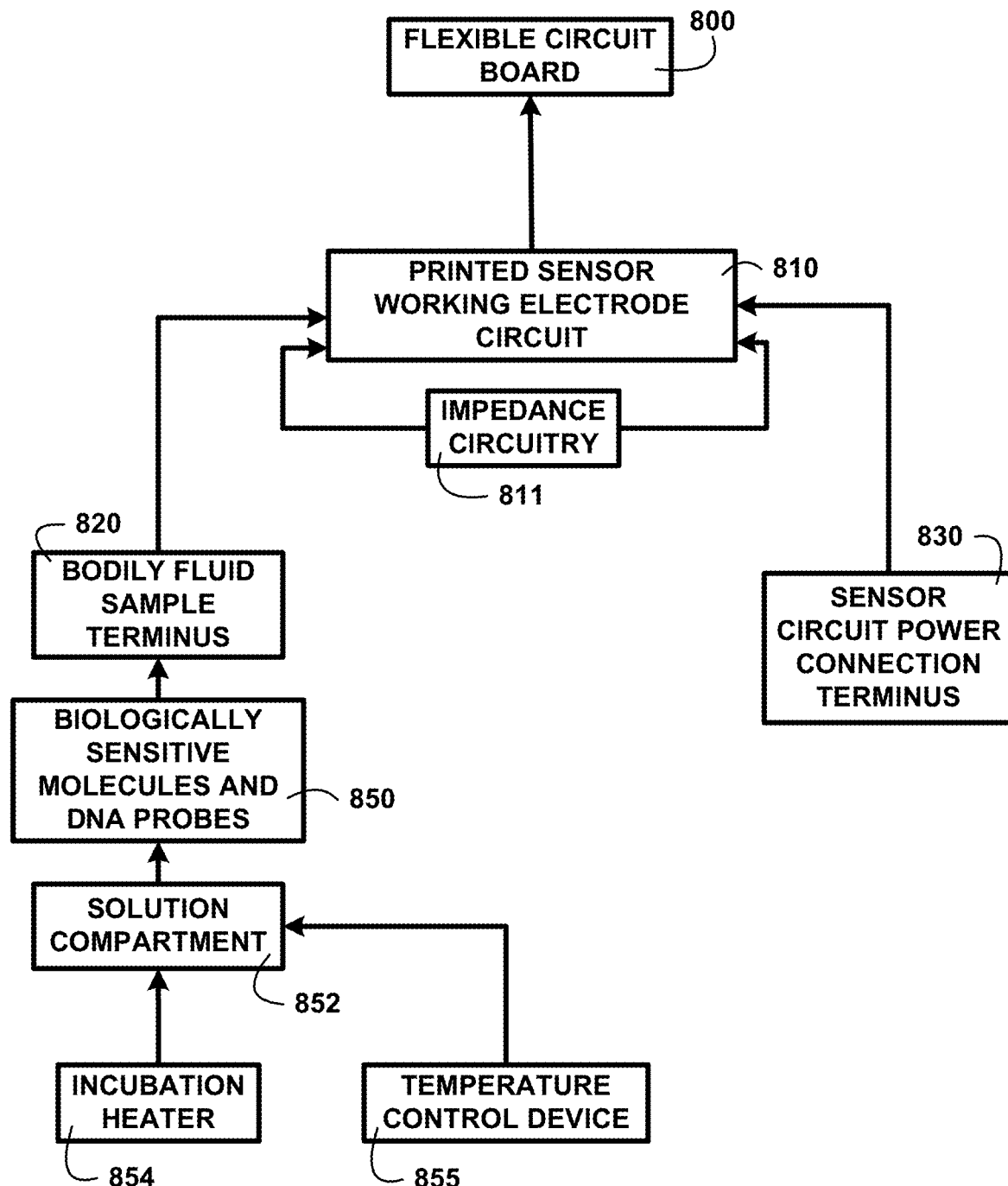
FIG. 8 shows a block diagram of an overview of a printed sensor electrode circuit of one embodiment.

A Printed Sensor Electrode Circuit:

FIG. 8 shows a block diagram of an overview of a printed sensor electrode circuit of one embodiment. FIG. 8 shows a flexible circuit board 800 with a printed sensor working electrode circuit 810 deposited on the surface. The printed sensor electrode circuit 810 can be made using printers including an inkjet printer, screen printer, 3D printer, or other forms of electrophotography printing. The electrode is composed of an electrically conductive material of one embodiment.

The printed sensor electrode impedance circuitry 811 is configured with a bodily fluid sample terminus 820. The bodily fluid sample terminus 820 includes DNA biologically sensitive molecules probes 850 that will be in contact with the patient bodily fluid sample with placed. A solution compartment 852 is coupled over the DNA biologically sensitive molecules probes 850 for receiving a bodily fluid sample. An incubation temperature control device 854 is placed under the solution compartment 852. The incubation temperature control device 854 may include a positive temperature coefficient temperature control device 855 using conductive ink. Temperature control devices are self-regulating heaters that run open-loop without any external diagnostic controls. Other methods of sample treatment can be used including treatment using chemicals and materials. The opposite end of the printed sensor working electrode circuit 810 includes a sensor circuit power connection terminus 830 for connecting a power source of one embodiment.

Figure 9:
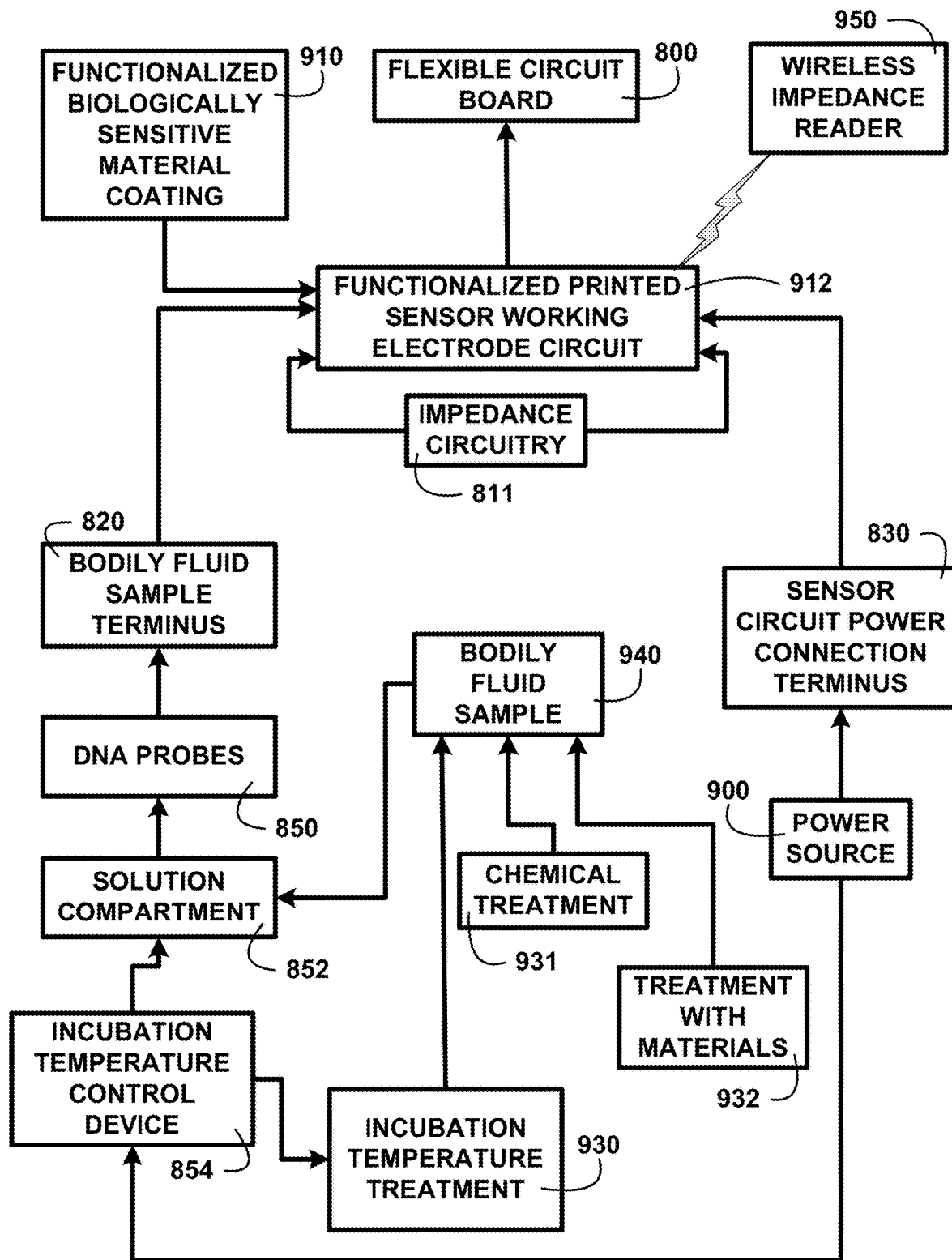
FIG. 9 shows a block diagram of an overview of a functionalized printed sensor working electrode circuit of one embodiment.

A Functionalized Printed Sensor Working Electrode Circuit:

FIG. 9 shows a block diagram of an overview of a functionalized printed sensor working electrode circuit of one embodiment. FIG. 9 shows the flexible circuit board 800, a printed sensor working electrode circuit 810, impedance circuitry 811, bodily fluid sample terminus 820, DNA biologically sensitive molecules probes 850, solution compartment 852, incubation temperature control device 854, and sensor circuit power connection terminus 830.

A functionalized biologically sensitive molecule material coating 910 is deposited on the surface of the printed sensor working electrode circuit 810 to form a functionalized printed sensor working electrode circuit 912. A bodily fluid sample 940 is shown placed in the solution compartment 852 and contacting the DNA biologically sensitive molecules probes 850. A power source 900 is coupled to the sensor circuit power connection terminus 830 for providing power to the incubation temperature control device 854 and other types of heaters including a temperature control device 855 of FIG. 8 for incubation heat 930 to the bodily fluid sample 940 during incubation of one embodiment. A chemical treatment 931 or treatment with materials 932 can be applied to the bodily fluid sample 940 in other embodiments. The power source 900 also provides power for impedance testing that is read using a wireless impedance reader 950 of one embodiment.

Figure 10A:
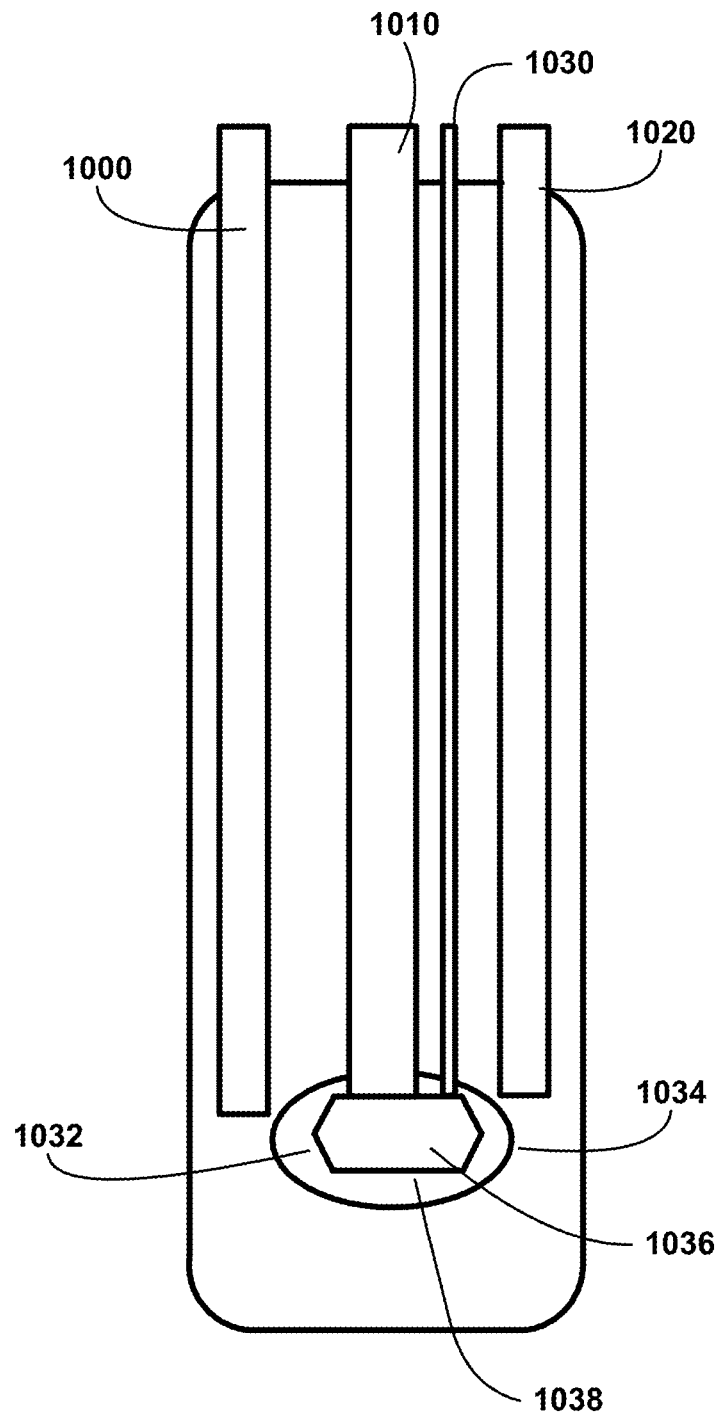
FIG. 10A shows for illustrative purposes only an example of an incubation heater of one embodiment.

An Incubation Heater:

FIG. 10A shows for illustrative purposes only an example of an incubation heater of one embodiment. FIG. 10A shows a heater below working electrode head 1036 that is used for heating a patient bodily fluid sample during incubation. In one embodiment the detection device includes a reference electrode 1000, working electrode 1010, and counter electrode 1020. The working electrode head 1034 is shown coupled to a heated fluid tube 1030.

A solution compartment 1038 is used for placing the patient bodily fluid sample. The solution compartment can be located in the sidewall next to the head of the working electrode separated by a thin film that melts away or directly above the working electrode such that when the sample is placed in the hole from above the heater then melts the top membrane so the sample mixes then the bottom member melts, allowing the mixed sample to pour down on the working electrode surface 1032. All body fluids will be able to be tested, however; different test strips will need different combinations of fluid and heat or none at all of one embodiment.

Figure 10B:
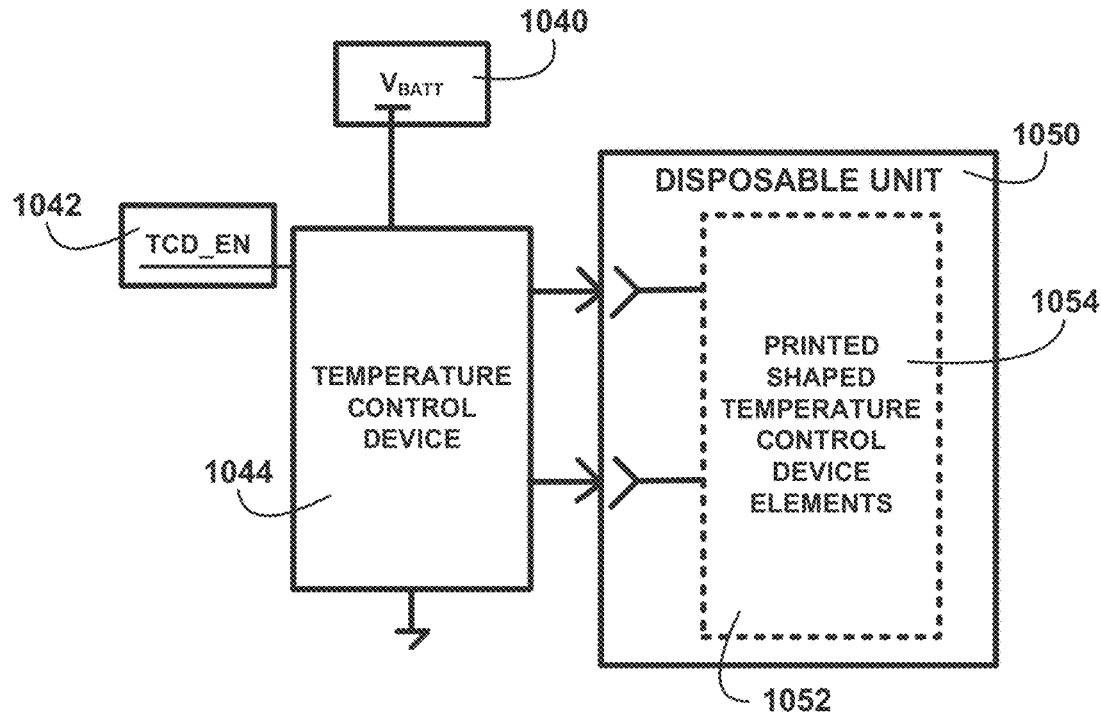
FIG. 10B shows for illustrative purposes only an example of a printed temperature control device of one embodiment.
Figure 10C:
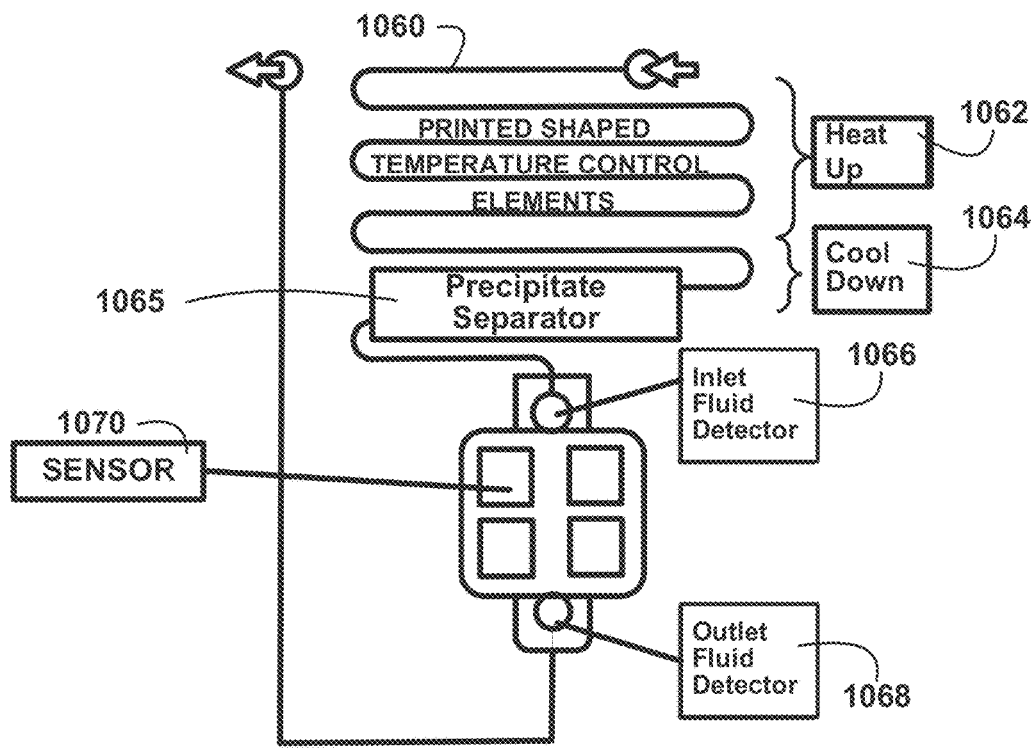

A Printed Heater:

FIG. 10B shows for illustrative purposes only an example of a printed temperature control device of one embodiment. FIG. 10B shows a Vbatt 1040 power source, a TCD en 1042, and temperature control drive 1044 that operate the heating/cooling system of a disposable unit 1050. The disposable unit 1050 consists of a temperature control device for example a printed temperature control device 1052 with for example a shaped printed temperature control device element including a shaped printed temperature control device element 1054.

A drive circuit for a printed temperature control device is used for heating a patient bodily fluid sample. The drive circuit can be microcontroller-based, analog, or a combination. The temperature control device resistance itself is used to determine temperature. In one embodiment a temperature control device can include for example a shaped printed element based on printable conductive ink otherwise known as a positive temperature coefficient (PTC) temperature control device. The base resistance can be scaled linearly by adjusting the size of the shaped printed element of one embodiment.

A Printed Heater and Printed Sensor:

FIG. 10O shows for illustrative purposes only an example of a printed temperature control device and printed sensor of one embodiment. FIG. 10O shows a printed temperature control device and printed sensor consisting of a shaped temperature control element 1060, heater 1062, cool down 1064; precipitate separator 1065, inlet fluid detector 1066, outlet fluid detector 1068, and at least one sensor 1070 of one embodiment.

Figure 11A:
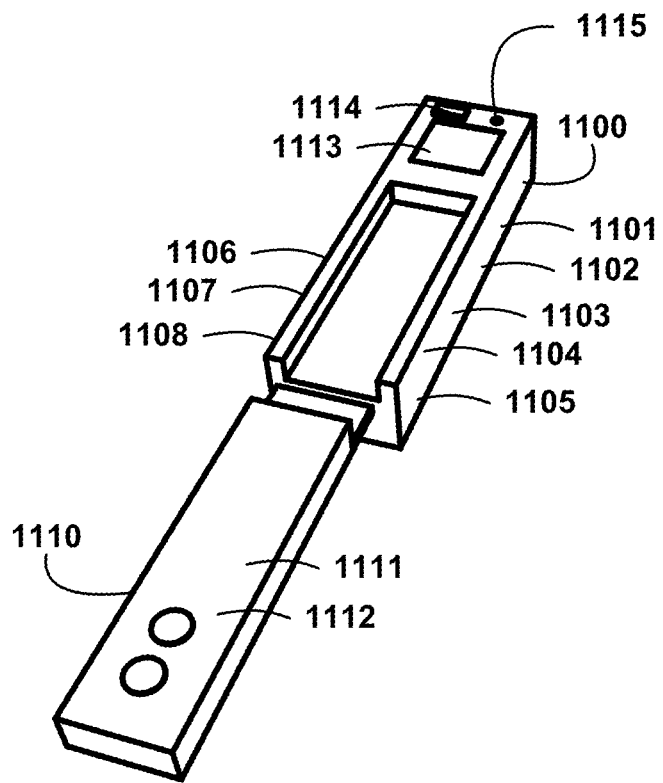
FIG. 11A shows for illustrative purposes only an example of a detection cartridge of one embodiment.

A Detection Cartridge:

FIG. 11A shows for illustrative purposes only an example of a detection cartridge of one embodiment. FIG. 11A shows an electrochemical sensing platform device 1100 including a processor 1101, at least one internal and external power source 1102, at least one communication device 1103, and at least one digital memory device 1104. The electrochemical sensing platform device 1100 is configured to include an impedance measuring device 1105, an interpretation processor 1106, at least one data cartridge reader 1107, and at least one testing protocol that controls digital memory identification activator 1108. The electrochemical sensing platform device 1100 includes a testing status display 1113 for displaying the testing process status and results. An on/off and selection button 1114 is used for turning on the power which is shown in a power-off indicator light 1115 condition. At least one detection cartridge 1110 includes at least one functionalized printed electrode 1111 and an incubation heater 1112 of one embodiment.

Figure 11B:
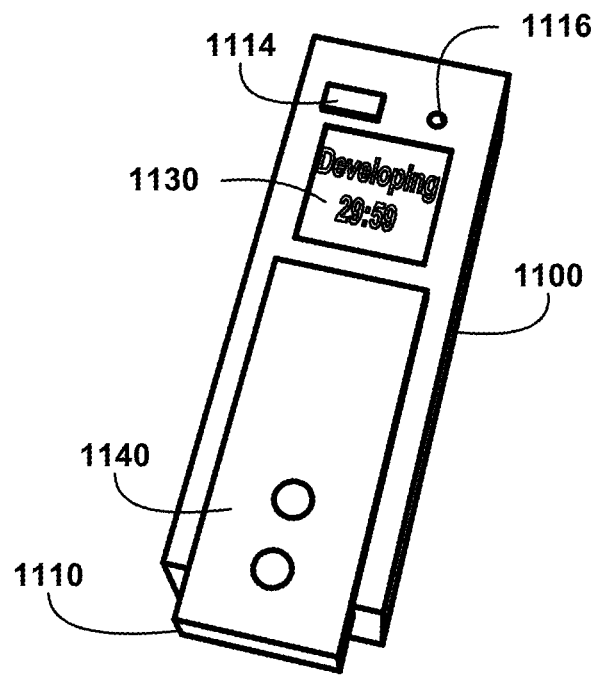
FIG. 11B shows for illustrative purposes only an example of a detection device of one embodiment.

A Detection Device:

FIG. 11B shows for illustrative purposes only an example of a detection device of one embodiment. FIG. 11B shows electrochemical sensing platform device 1100 includes at least one detection cartridge 1110 and an on/off and selection button 1114. In this instance, the power-on indicator light 1116 is lit indicating the power has been turned on. A detection cartridge inserted into the electrochemical sensing platform 1140 produces a testing status display showing developing 29.59 1130 of one embodiment.

Figure 12A:
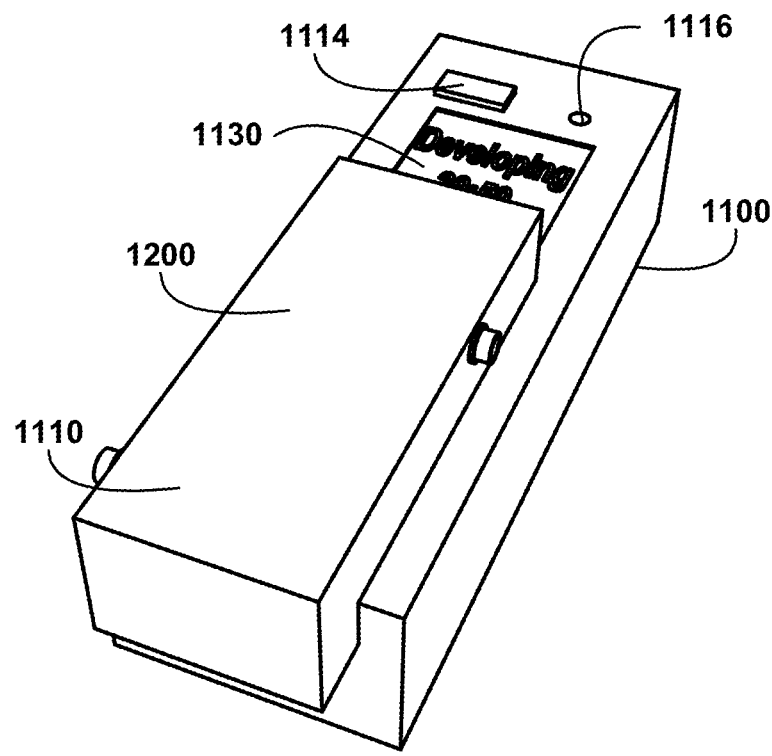
FIG. 12A shows for illustrative purposes only an example of a detection device display developing of one embodiment.

A Detection Device Display Developing:

FIG. 12A shows for illustrative purposes only an example of a detection device display developing of one embodiment. FIG. 12A shows the electrochemical sensing platform device 1100, at least one detection cartridge 1110, on/off and selection button 1114, power-on indicator light 1116, testing status display showing developing 29.59 1130 in a high fluid volume detection cartridge 1200 of one embodiment.

Figure 12B:
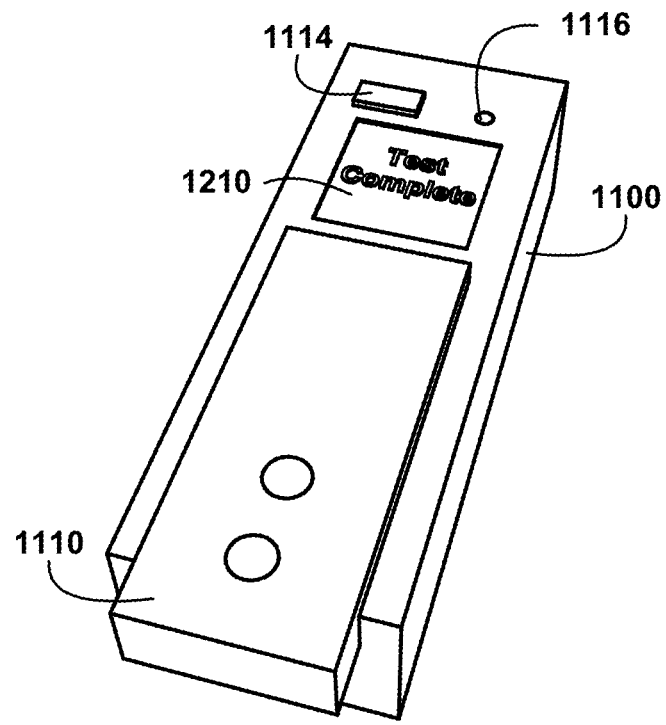
FIG. 12B shows for illustrative purposes only an example of a detection device display test complete of one embodiment.

A Detection Device Display Test Complete:

FIG. 12B shows for illustrative purposes only an example of a detection device display test complete of one embodiment. FIG. 12B shows the electrochemical sensing platform device 1100, at least one detection cartridge 1110, on/off and selection button 1114, and power-on indicator light 1116. A testing status display showing test complete 1210 and the end of a testing process cycle of one embodiment.

Figure 13:
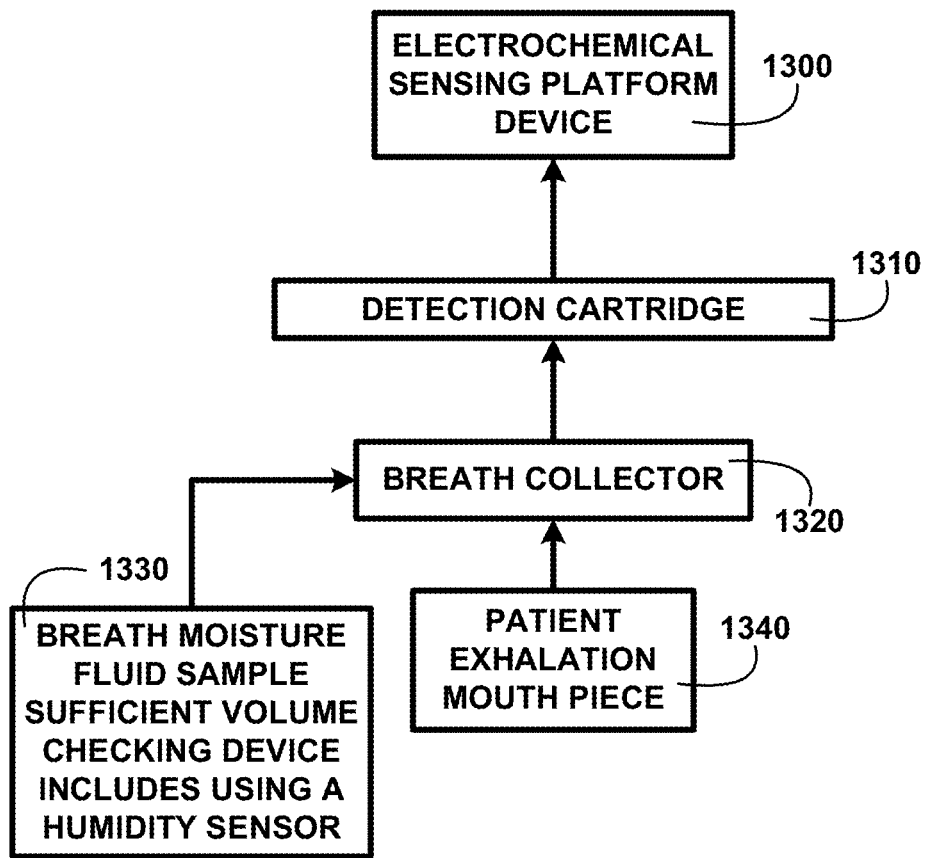
FIG. 13 shows a block diagram of an overview of a detection cartridge breath collector of one embodiment.

A Detection Cartridge Breathe Collector:

FIG. 13 shows a block diagram of an overview of a detection cartridge breath collector of one embodiment. FIG. 13 shows in another embodiment an electrochemical sensing platform device 1300. Coupled to the electrochemical sensing platform device 1300 is a detection cartridge 1310. The detection cartridge 1310 is configured with a patient exhalation mouthpiece 1340. The patient's exhalation mouthpiece 1340 is coupled to a breath collector 1320. The breath collector 1320 is used to collect moisture in the exhaled air of the patient. The breath collector 1320 includes a breath moisture fluid sample sufficient volume checking device includes using a humidity sensor 1330. A patient may need to exhale a number of times to allow the collection of sufficient moisture to perform the testing of one embodiment.

Figure 14:
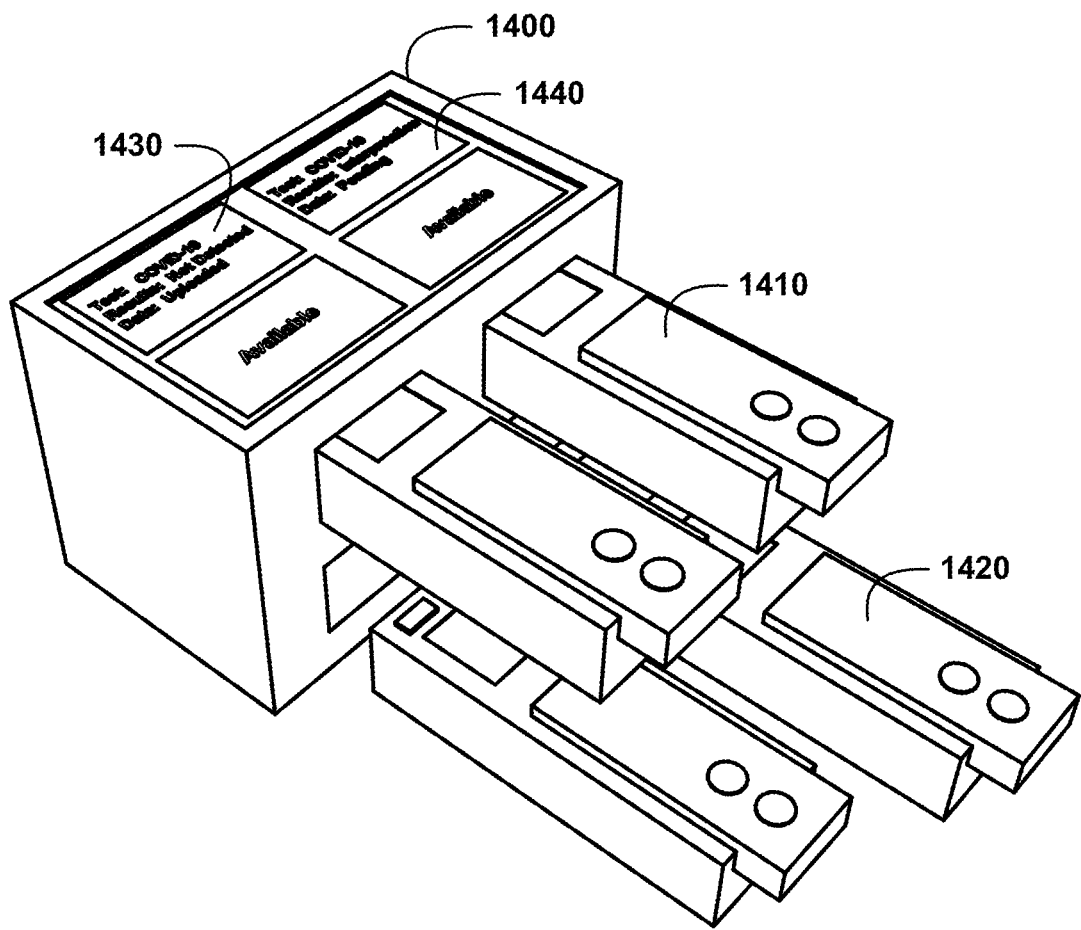
FIG. 14 shows for illustrative purposes only an example of a multi-reader of one embodiment.

A Multi-Reader:

FIG. 14 shows for illustrative purposes only an example of a multi-reader of one embodiment. FIG. 14 shows a multi detection device reader 1400. The multi detection device reader 1400 is shown with at least one detection device inserted into the multi detection device reader 1410. Also showing is at least one detection device not inserted into the multi detection device reader 1420. The multi detection device reader 1400 includes test results displays. In this instance, one test results display showing uploaded 1430 and the other test results display showing pending 1440 of one embodiment. In another embodiment, the multi-reader can also be wireless such that the test cartridges sit on the table and transmit the data wirelessly to the multi-reader receiver.

Figure 15:
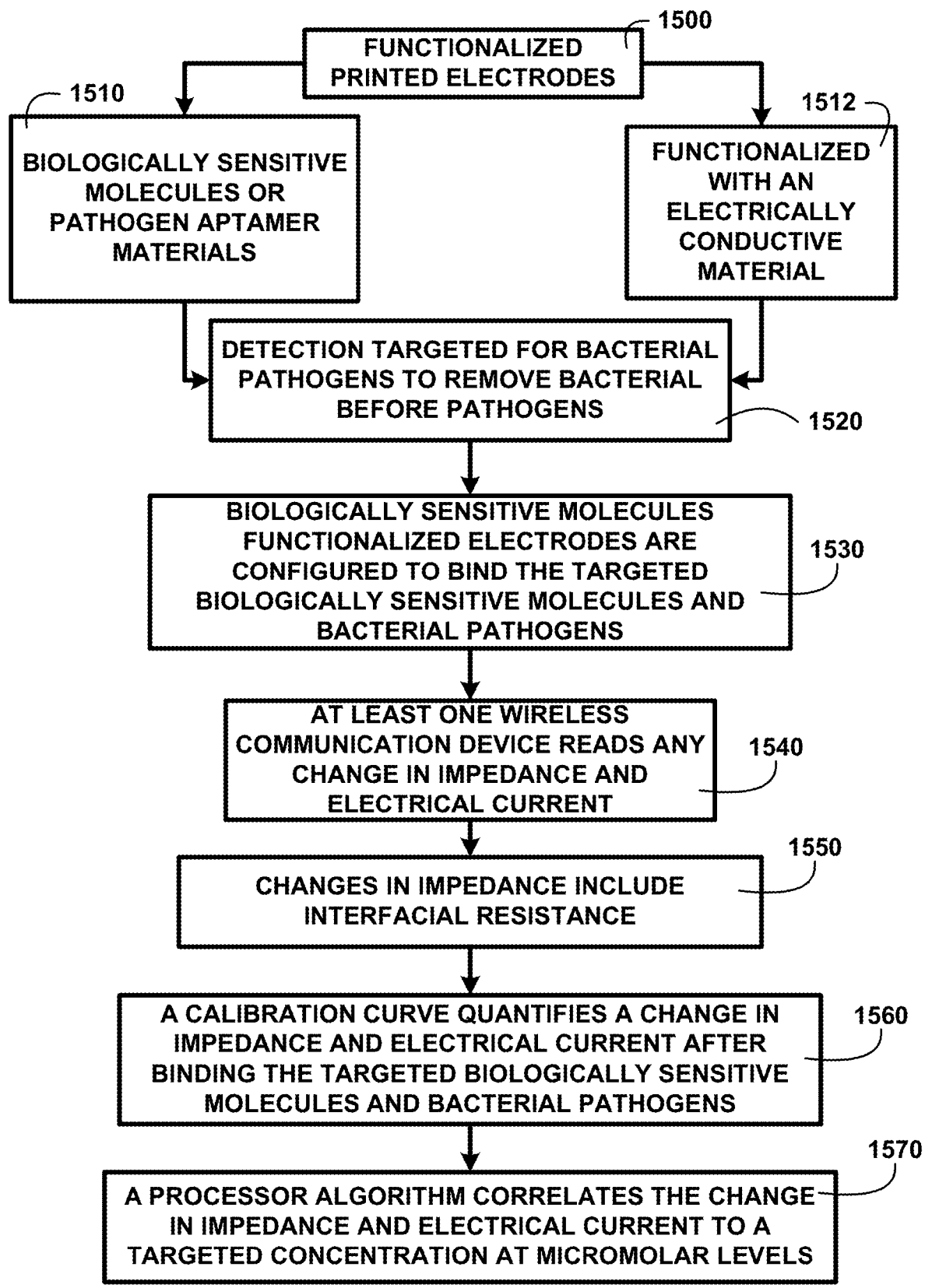
FIG. 15 shows a block diagram of an overview of functionalized printed electrodes of one embodiment.
Figure 17:
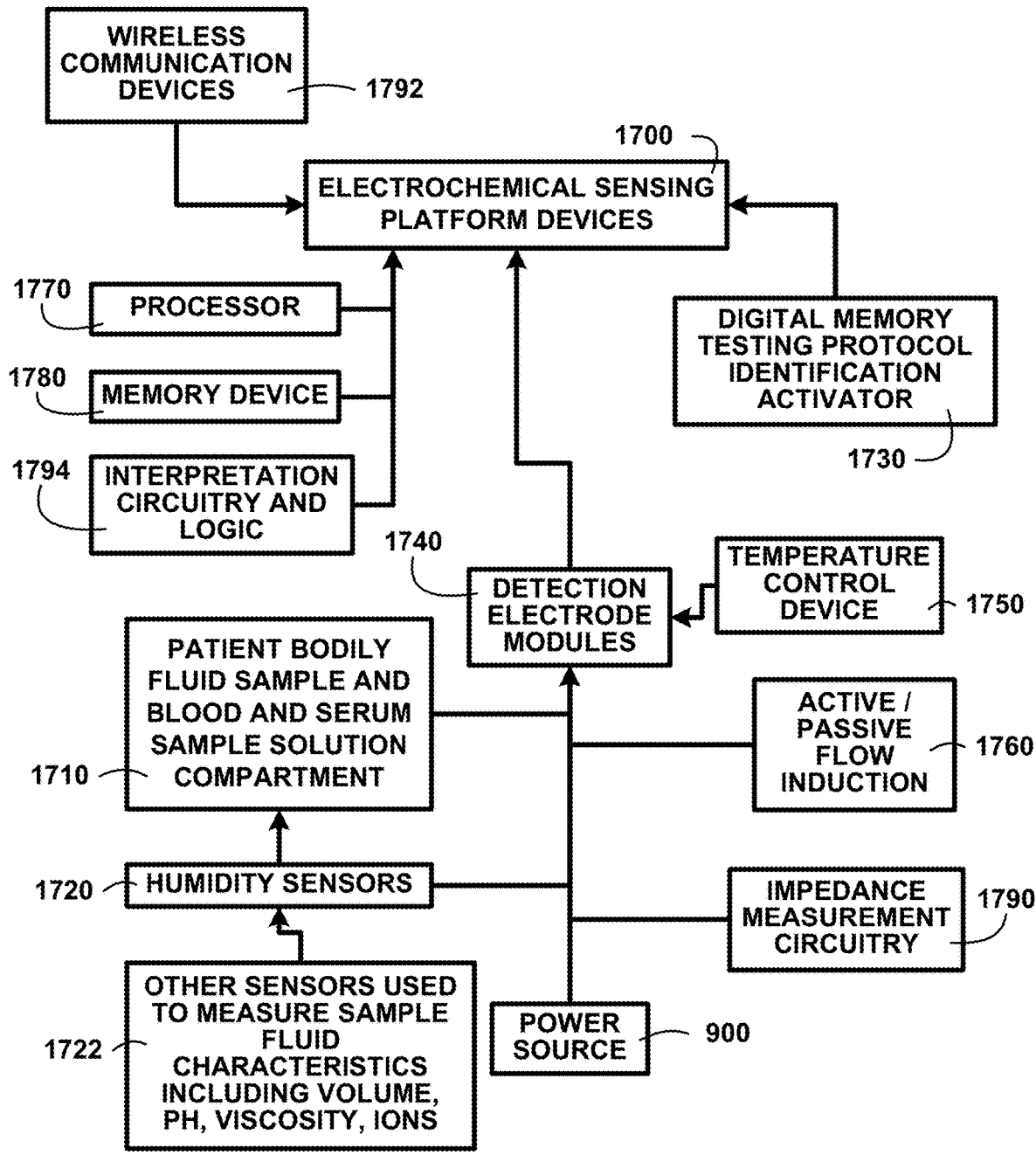
FIG. 17 shows a block diagram of an overview of electrochemical sensing platform devices of one embodiment.
Figure 18A:
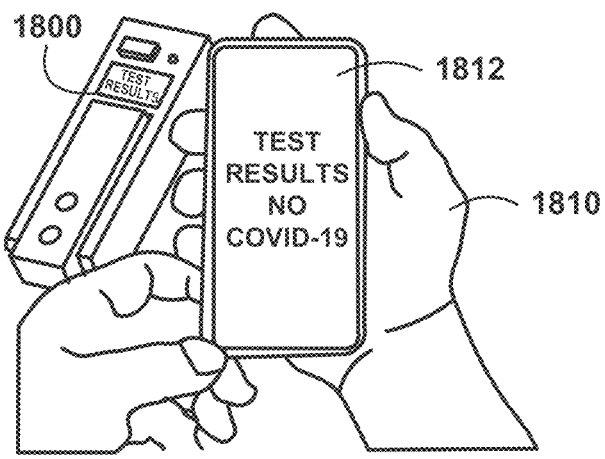
FIG. 18A shows for illustrative purposes only an example of home use application environment of one embodiment.
Figure 18B:
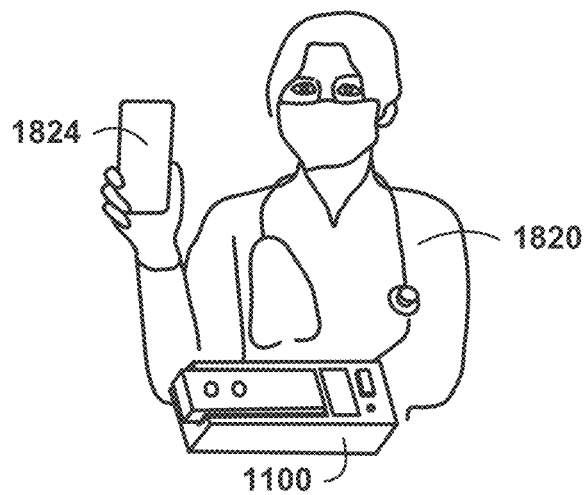
FIG. 18B shows for illustrative purposes only an example of clinic use application environment of one embodiment.
Figure 18C:
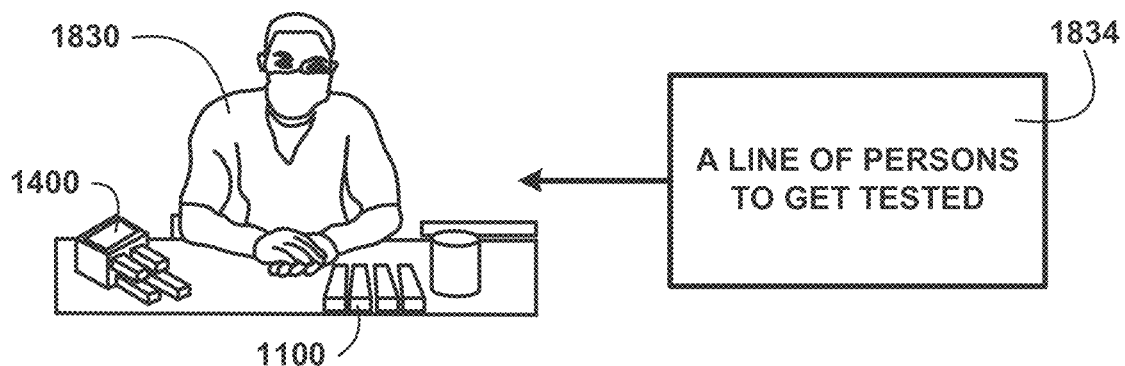
FIG. 18C shows for illustrative purposes only an example of mass-use application environment of one embodiment.
Figure 19:
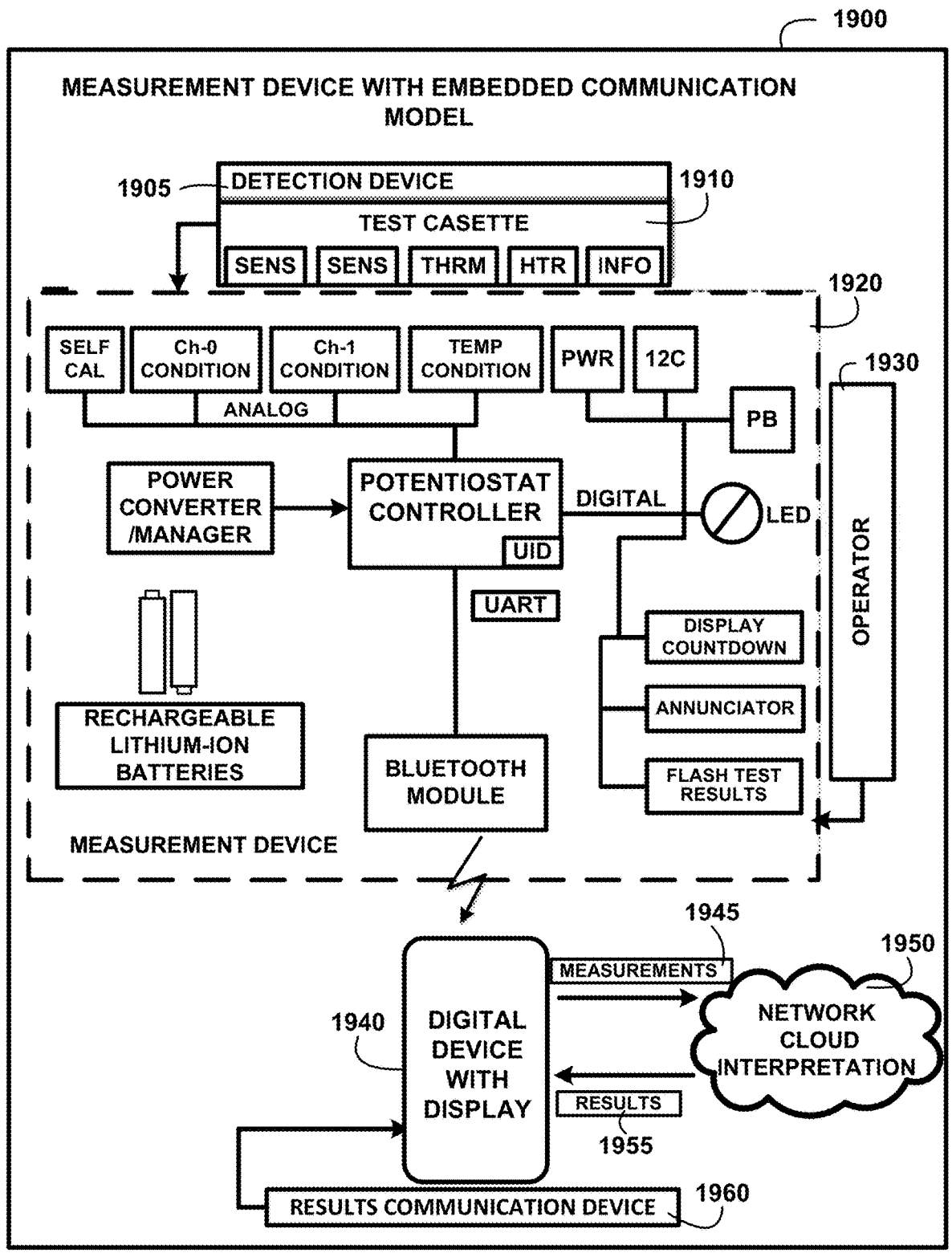
FIG. 19 shows for illustrative purposes only an example of a measurement device with embedded communication home use model of one embodiment.
Figure 20:
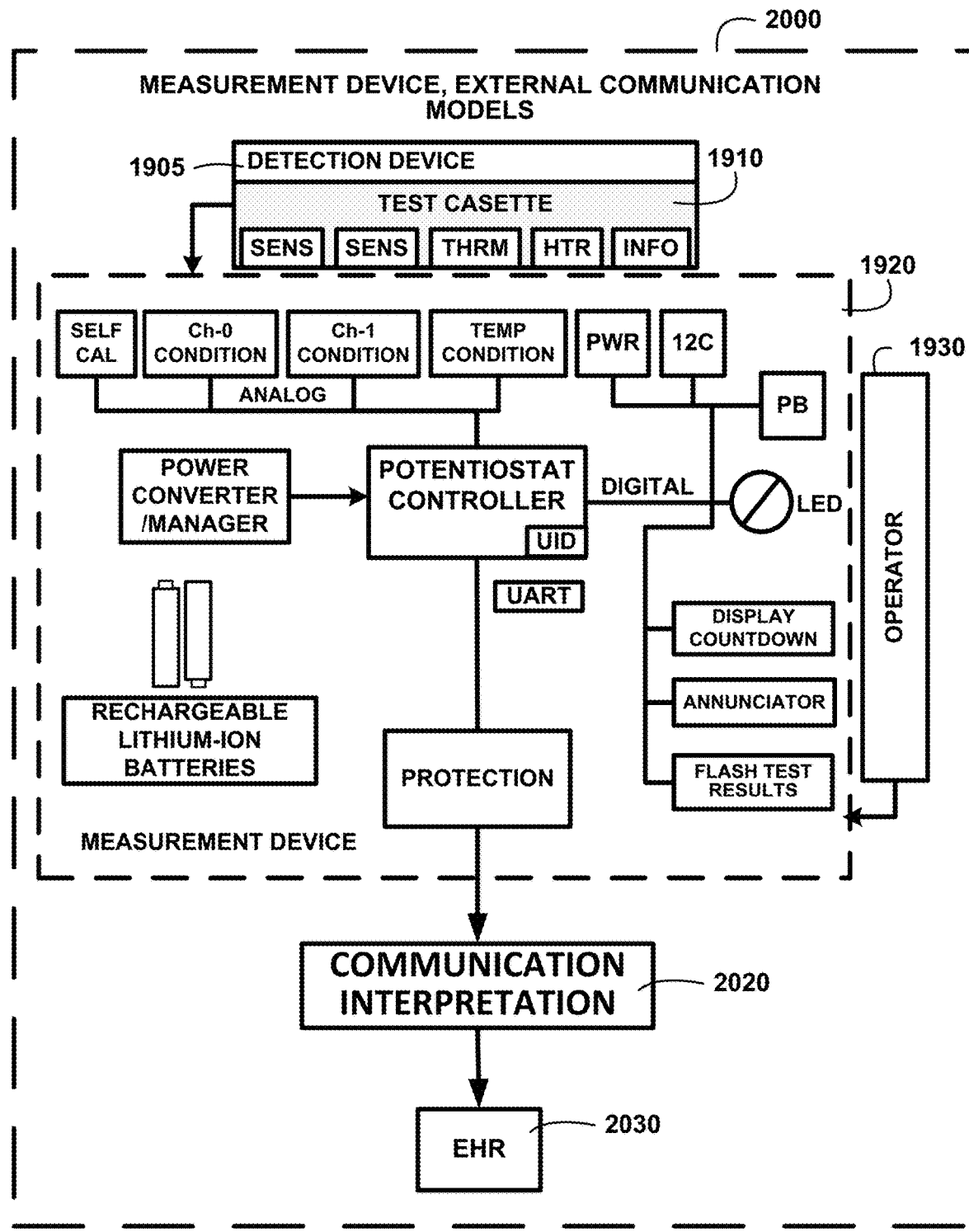
FIG. 20 shows for illustrative purposes only an example of a measurement device, external communication clinic, and mass use models of one embodiment.
Figure 21:
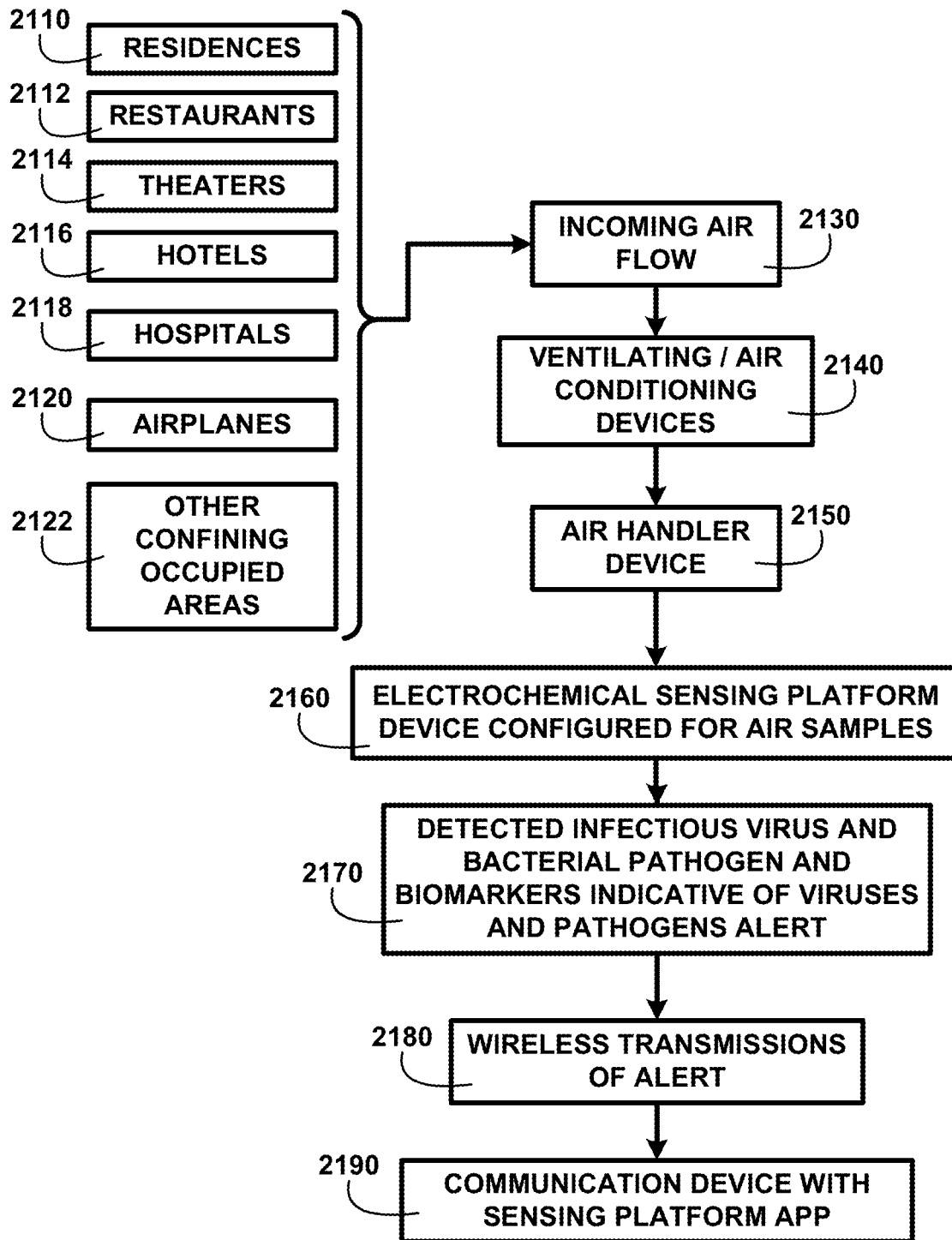
FIG. 21 shows a block diagram of an overview of electrochemical air sampling sensing platform devices of one embodiment.

Functionalized Printed Electrodes:

FIG. 15 shows a block diagram of an overview of functionalized printed electrodes of one embodiment. FIG. 15 shows functionalized printed electrodes 1500. The functionalized printed electrodes 1500 are functionalized with biologically sensitive molecules or pathogen aptamer materials 1510. In another embodiment, printed electrodes 1500 are functionalized with an electrically conductive material 1512. The DNA biologically sensitive molecules probes 850 of FIG. 8B consists of materials corresponding to the specific biologically sensitive molecules and bacterial pathogens biologically sensitive molecules and aptamer materials. The functionalized printed electrodes 1500 are configured for detection targeted for bacterial pathogens to remove bacterial before pathogens 1520.

Electrodes functionalized with biologically sensitive molecules are configured to bind the targeted biologically sensitive molecules and bacterial pathogens 1530 to the probes and aptamers. At least one wireless communication device reads any change in impedance and electrical current 1540 and records any changes for transmission to an interpretation means. Changes in impedance include interfacial resistance 1550. A calibration curve quantifies a change in impedance and electrical current after binding the targeted biologically sensitive molecules and bacterial pathogens 1560. A processor algorithm correlates the change in impedance and electrical current to a targeted concentration at micromolar levels 1570.

Functionalizing the sensor electrodes by electrostatically binding primers or aptamers of an analytical target pathogen to the sensor electrodes is configured for attracting and binding pathogen genetic material or proteins to add pathogen specific material to the conductive path of an electrode electrical circuit thereby changing the impedance and the electrical current. The measurement of the electrical current change is indicative of a positive or negative test result. Functionalizing the sensor electrodes by electrostatically binding primers or aptamers of an analytical target pathogen to the sensor electrodes is configured for attracting and binding pathogen genetic material or proteins to add pathogen specific material to the conductive path of an electrode electrical circuit thereby changing the impedance and the electrical current. The measurement of the electrical current change is indicative of a positive or negative test result of one embodiment.

Electrode Binding of Targeted Biologically Sensitive Molecules and Bacterial Pathogens:

FIG. 16 shows a block diagram of an overview of an example of electrode binding of targeted biologically sensitive molecules and bacterial pathogens of one embodiment. FIG. 16 shows the electrochemical detection device for COVID-19 SARS-CoV-2 virus in bodily fluids 1600. A nozzle deposits an electrically conductive electrode material 1604 on a substrate 1640 or other common thermoplastic polymers including Polyethylene terephthalate to make a printed sensor electrode 1610. A biologically sensitive molecule coating specific for SARS-CoV-2 is bound to the electrically conductive electrode 1620 to form a functionalized printed electrode. Coupled to the precision-printed sensor electrode 1610 are an external power source 1613 and an internal power source 1612. Also coupled to the printed sensor electrode 1610 is a solution compartment 1615 the receiver for the bodily fluid sample 1617.

An incubation temperature control device 854 is coupled underneath the solution compartment 1615. The internal power source 1612 is shown connected to the incubation temperature control device 854 for applying heat to the bodily fluid sample during the predetermined incubation time period. During incubation, the SARS-CoV-2 is bound to the electrically conductive electrodes with biologically sensitive molecule 1622. Each terminus of the sensor electrode forms a measurement circuit for processing an impedance measurement 1650. The impedance measurement 1650 is read with a WIFI transmission to a smartphone 1660. Interpretation is processed on a sensing platform smartphone app on a patient smartphone 1670. The testing results displayed on a sensing platform smartphone app 1680 let the patient know quickly if they are infected with the COVID-19 SARS-CoV-2 virus of one embodiment.

Electrochemical Sensing Platform Devices:

FIG. 17 shows a block diagram of an overview of electrochemical sensing platform devices of one embodiment. FIG. 17 shows electrochemical sensing platform devices 1700 that are configured with wireless communication devices 1792, at least one processor 1770, memory device 1780, interpretation circuitry and logic 1794, and impedance measurement circuitry 1790. Detection electrode modules 1740 are inserted into the electrochemical sensing platform devices 1700 for reading and interpretation of the detection testing. Coupled to the detection electrode modules 1740 is a patient bodily fluid sample including blood, serum, and other test samples solution compartment 1710. Coupled to the patient bodily fluid sample including blood, serum, and other test samples solution compartment 1710 are humidity sensors 1720 and other sensors used to measure sample fluid characteristics including volume, Ph, viscosity, ions 1722. Also coupled to the detection electrode modules 1740 are at least one digital memory testing protocol Identification activator 1730, temperature control device 1750, and active/passive airflow induction 1760. Another element coupled to the detection electrode modules 1740 is a power source 900 of one embodiment.

Application Environments:

FIGS. 18A, 18B, and 18C show application environments for use of the electrochemical sensing platform devices and processes 100 of FIG. 1. FIG. 18A shows for illustrative purposes only an example of the home use application environment of one embodiment. FIG. 18A shows in one embodiment the electrochemical sensing platform devices and processes 100 of FIG. 1 are configured for home use with an untrained user, following written instructions 1810. The home use processing of the electrochemical sensing platform device 1800 with detection, measurement, and interpretation means reported to the user via a sensing platform smartphone app 1812 that in this instance reports "Test Results no Covid-19".

FIG. 18B shows for illustrative purposes only an example of clinic use application environment of one embodiment. FIG. 18B shows in another embodiment Clinical Use with a semi-trained user 1824, having previously performed the test and follows written instructions 1820. Processing includes electrochemical sensing platform device 1100 with detection, measurement, and test data transmitted over WIFI to a network for reading and interpretation and reporting results on a sensing platform smartphone app in this instance waiting for the results report to be displayed.

FIG. 18C shows for illustrative purposes only an example of a mass-use application environment of one embodiment. FIG. 18C shows in yet another embodiment Mass Use with a trained operator 1830, repeatedly performing the tests from documented procedures, conversant in test sampling and preparation techniques. Mass Use utilizes an electrochemical sensing platform device 1100 with detection, measurement, and using an external multiple device multi-reader and interpretation device transceiver 1400. The interpretation device transceiver can be configured with hard-wire and wireless communication to the network interpretation means. The multiple device multi-reader and interpretation device transceiver 1400 facilitates processing test of a large number of people 1834 in a short period of time.

A Measurement Device with Embedded Communication Home Use Model:

FIG. 19 shows for illustrative purposes only an example of a measurement device with embedded communication home use model of one embodiment. FIG. 19 shows an example of a measurement device with embedded communication home use model 1900. The home-use model includes a detection device 1905 with a test cassette 1910 with modules for SENS, SENS, THRM, HTR, and INFO. A measurement device 1920 is configured with PWR, 12C, PB, and an LED. The measurement device 1920 includes operations of a displayed countdown, annunciator, and flash test results. An operator 1930 turns on and off and makes selections of the operations of the home use model.

The measurement device 1920 includes analog operations for self-cal (calibration), Ch-0 condition, Ch-1 condition, and temp condition. The measurement device 1920 includes a potentiostat controller UID, power converter/manager for rechargeable batteries, digital devices. UART and Bluetooth® module. The Bluetooth® module communicates with at least one communication device 1960 including a smartphone 1940 for transmitting and receiving data including measurements 1945, cloud (interpretation) 1950 and results 1955 of one embodiment.

A Measurement Device, External Communication Clinic, and Mass Use Models:

FIG. 20 shows for illustrative purposes only an example of a measurement device, external communication clinic, and mass use models of one embodiment. FIG. 20 shows an example of a measurement device, external communication clinic, and mass use models 2000. The clinic and mass use models include a detection device 1905 with a test cassette 1910 with modules for SENS, SENS, THRM, HTR, and INFO.

A measurement device 1920 is configured with PWR, 12C, PB, and an LED. The measurement device 1920 includes operations of a displayed countdown, annunciator, and flash test results. An operator 1930 turns on and off and makes selections of the operations of the home use model. The measurement device 1920 includes analog operations for self-cal (calibration), Ch-0 condition, Ch-1 condition, and temp condition.

The measurement device 1920 includes a potentiostat controller UID, power converter/manager for rechargeable batteries, digital devices. UART and protection. Communication interpretation 2020 is performed on external devices wherein the detection and measurement data is communicated to a network for interpretation. The interpretation results are transmitted to a patient EHR 2030 of one embodiment.

Electrochemical Air Sampling Sensing Platform Devices:

FIG. 21 shows a block diagram of an overview of electrochemical air sampling sensing platform devices of one embodiment. FIG. 21 shows areas where people congregate frequently including residences 2110, restaurants 2112, theaters 2114, hotels 2116, hospitals 2118, airplanes 2120, and other confining occupied areas 2122.

One commonality of these locations is the ventilating of the indoor air. Incoming airflow 2130 to ventilating/air conditioning devices 2140 is passed through the rooms and other occupied areas by the ventilating/air conditioning devices 2140 air handler device 2150. The testing of this air can detect the presence of infectious viruses and bacterial pathogens or biomarkers indicative of the presence of infectious viruses and bacterial pathogens including SARS-CoV-2 and other viruses, MSRA, Legionnaires770830, and other infectious microorganisms.

In one embodiment, an electrochemical sensing platform device configured for air samples 2160 will test the air as it passes through the electrochemical sensing platform device configured for air samples 2160. The electrochemical sensing platform device configured for air samples 2160 will be placed within the airflow.

Should the electrochemical sensing platform device detect any infectious viruses and bacterial pathogens in the air the device will broadcast a detected infectious virus and bacterial pathogen alert 2170. Communication devices in the electrochemical sensing platform device will initiate wireless transmissions of alert 2180 to a user communication device with sensing platform app 2190 so they can take appropriate actions of one embodiment.

Figure 22:
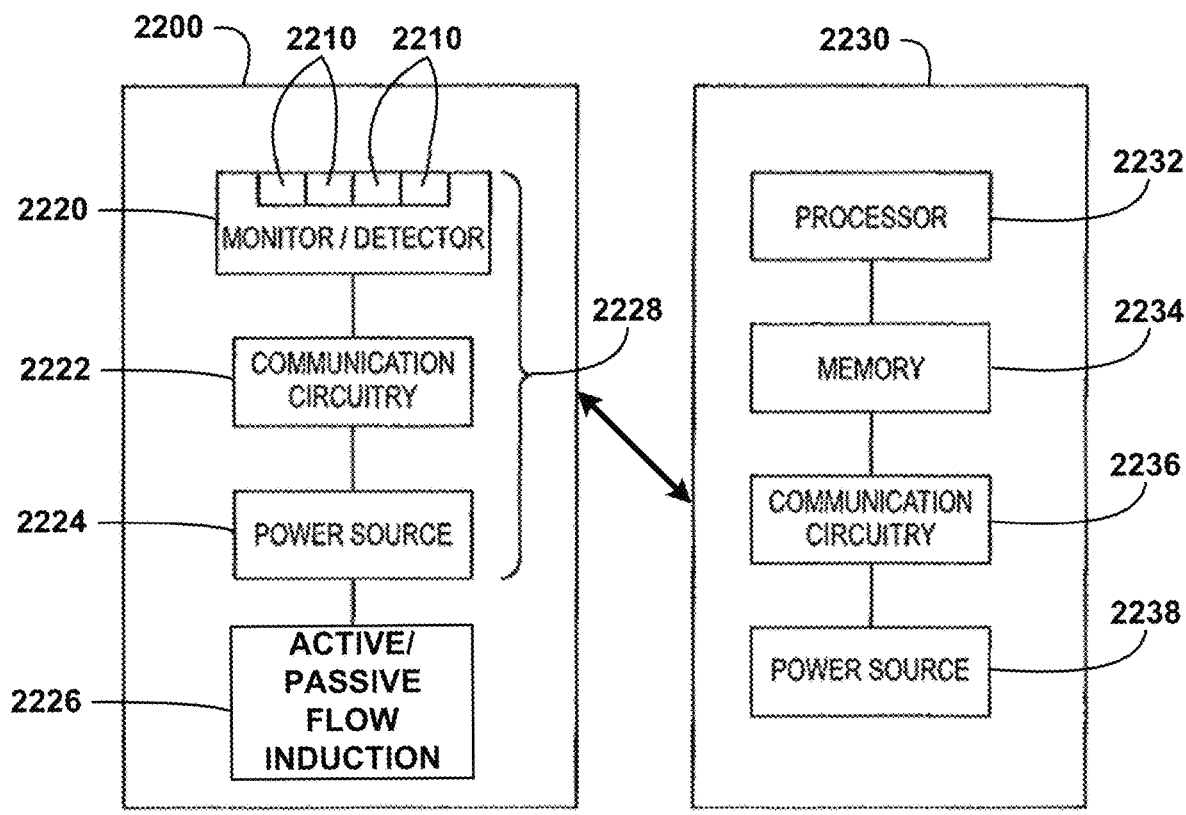
FIG. 22 shows for illustrative purposes only an example of an exemplary system of one embodiment.

Exemplary System:

FIG. 22 shows for illustrative purposes only an example of an exemplary system of one embodiment. FIG. 22 shows a monitor system 2200 generally includes a monitor/detector component 2220. One monitor/detector component 2220 that is particularly well-suited for purposes of the present disclosure is set forth in U.S. Pat. No. 8,629,770 to Hummer et al. and U.S. Pat. No. 7,176,793 to Hummer, both of which are incorporated herein by reference in their entireties. Other types of monitor/detector components can also be used in accordance with the present disclosure.

The monitor system 2200 further includes communication circuitry 2222 and a power source 2238. The monitor system 2200 communication circuitry 2222, in one embodiment, includes at least one of a near field communication device, Bluetooth® communication device, WIFI communication device, or any other suitable communication circuitry for establishing communications with a cell phone. The power source 2238 can be a power supply such as a battery (lithium or other) mounted or otherwise contained within case 2230.

In other embodiments, the power source 2238 can be an antenna configured to receive energy wirelessly and supply the received energy to one or both of the monitor/detector component 2220 and/or communication circuitry 2222 such that no onboard battery is required for the operation of the monitor system 2200. In still other arrangements, the monitor system 2200 power source 2224 can be a connector configured to couple with a port of the cell phone 2230 to receive power from a power source of the cell phone 2230.

An active or passive airflow induction device 2226 can be provided for ensuring adequate and or continuous flow of air to the monitor/detector component 2220. Such devices can include fans, micro pumps, louvers, vents, etc. An active induction device can be separately replaceable within the system and can include its own power supply. Alternatively, an active induction device can be configured to receive power from power supply 2224.

It should be appreciated that the monitor/detector component 2220 can comprise a plurality of sensors 2210. The sensors 2210 can be individually replaceable or can be replaced as a unit. Replacement of the sensors may be necessary due to sensor degradation. In other situations, a user may wish to detect certain chemicals and will choose which sensors to install in the system. In one embodiment, the entire monitor system 2200 is replaceable as a unit.

The sensors 2210 may detect harmful materials, such as explosives, radioactive materials, harmful chemicals, such as chemical warfare agents, nerve gases, biological materials, such as gases, anthrax, and other germ warfare agents, narcotics, and other illegal drugs, or combinations thereof. At least one of the sensors 2210 can be configured for generating a signal which is indicative of the presence of a nitrogen-based explosive, such as trinitrotoluene (TNT) and/or a peroxide-based explosives, such as triacetone triperoxide (TATP) or hexamethylenetriperoxidediamine (HMTD), or a combination thereof, for example.

It will be appreciated that the monitor system 2200 is configured to communicate with the cell phone 2230. That is the monitor system 2200 collects data and transmits or otherwise shares the collected data with the cell phone 2230 for processing. The cell phone 2230 of the illustrated embodiment includes a processor 2232, a memory 2234, a cell phone 2230 communication circuitry 2236, and a power source 2238. It will be appreciated that the cell phone 2230 can include a wide variety of additional components as is conventional. Such additional components can include a display device, input device, various sensors, various antennas, etc.

Data collected by the monitor/detector 2220 is transmitted via communication circuitry 2222 to communication circuitry 2236 of the cell phone 2230. Other data, such as sensor state, status, performance data, and the like can also be transmitted to the cell phone 2230. Any suitable manner of transmitting the data from the monitor system 2200 to the cell phone 2230 can be employed.

The data collected and transmitted by the monitoring system 2200 is then processed by the phone to detect one or more chemicals in accordance with one or more methods set forth in U.S. Pat. No. 8,629,770 to Hummer et al. and U.S. Pat. No. 7,176,793 to Hummer. To this end, suitable software for analyzing the data is stored in memory 2234 of the cell phone 2230. Other detection and/or analyzing methods and techniques may also be used in conjunction with aspects of the present disclosure.

In one embodiment, the software stored in memory 2234 can be in the form of an application, or "app", that is downloaded from an app store or the like. The app can be provided with various "signatures" of chemicals. The signatures can be compared to the data to determine whether the chemical signature was detected by the monitoring system 2200. The app can be configured to be automatically updated with new signatures as the need to detect particular chemicals arises. That is, it is possible to provide new and/or additional chemical signatures for the app to check against the data to detect specific chemicals.

The app can further include features such as adjustable thresholds. For example, for some chemicals that are routinely present in certain amounts and/or not generally considered dangerous below certain levels, the application can be configured to detect or trigger an alarm when a threshold amount is met or exceeded. For some chemicals which are considered dangerous in any amount, the thresholds would not generally be adjustable.

The app can be further configured to, once a chemical is detected, share the detection information. For example, the application can be configured to use the communication circuitry 2236 to broadcast an alert (or generate a notification) via any suitable communications network (e.g., WIFI, NFC, Bluetooth®, cell, etc.). The alert may be directly sent to other cell phones and/or personal communication devices in the area or may be sent to a server (or through a network) and then on to devices within a range of a given location. Accordingly, the application can be configured to use location information from a GPS chip, WIFI, or any other location information available to the cell phone 2230 to identify the location of the detected chemical.

The app can be configured to alert the authorities in the event certain chemicals are detected. For example, the detection of any amount of sarin gas (or other chemical/biological agents) can trigger information relating to the location, time, etc. of the detection to be forwarded to certain designated authorities for threat management/mitigation.

It should be appreciated that a network of devices having monitoring systems, each detecting a certain chemical, can be configured to share valuable data regarding the dispersion of the particular chemical. For example, devices in close proximity to each other and the point of origin of the chemical may detect a greater concentration of the chemical than devices further away from the point of origin. Using this data and an appropriate dispersion model, a point of origin can be calculated. This can allow responsive action to be taken more quickly than otherwise would be the case.

Similarly, the data (location, concentration, etc.) from a plurality of such devices can be used to predict the dispersion of the chemical so that preemptive action can be taken to minimize exposure of humans to the detected chemical.

Providing the monitoring system 2200 in a separate component that is attachable to a phone or other personal communication device has several advantages. For example, any and all such devices can become monitors/detectors upon the provision of a suitable case or other components. Accordingly, a consumer can decide whether to add the functionality. In addition, the orientation, location, and other aspects of the positioning of the sensor elements within the case or other component can be standardized to provide more consistent detection as compared to placing the sensor elements within various models of cell phones. This is because the myriad phone manufacturers and models each have different space constraints that would dictate different available locations, orientations, etc. for the sensor elements within the phone. As such, some sensor elements would be in a better position within a respective phone to detect chemicals than other phones. This can lead to widely varying detection accuracy between different phones exposed to the same concentration of a given chemical.

It should be appreciated that, although the monitoring system 2200 is illustrated as part of a case 2205, the monitoring system 2200 can also be provided as a separate unit attachable either directly to a cell phone or the like, or attachable to a case in which a cell phone is contained.

Figure 23:
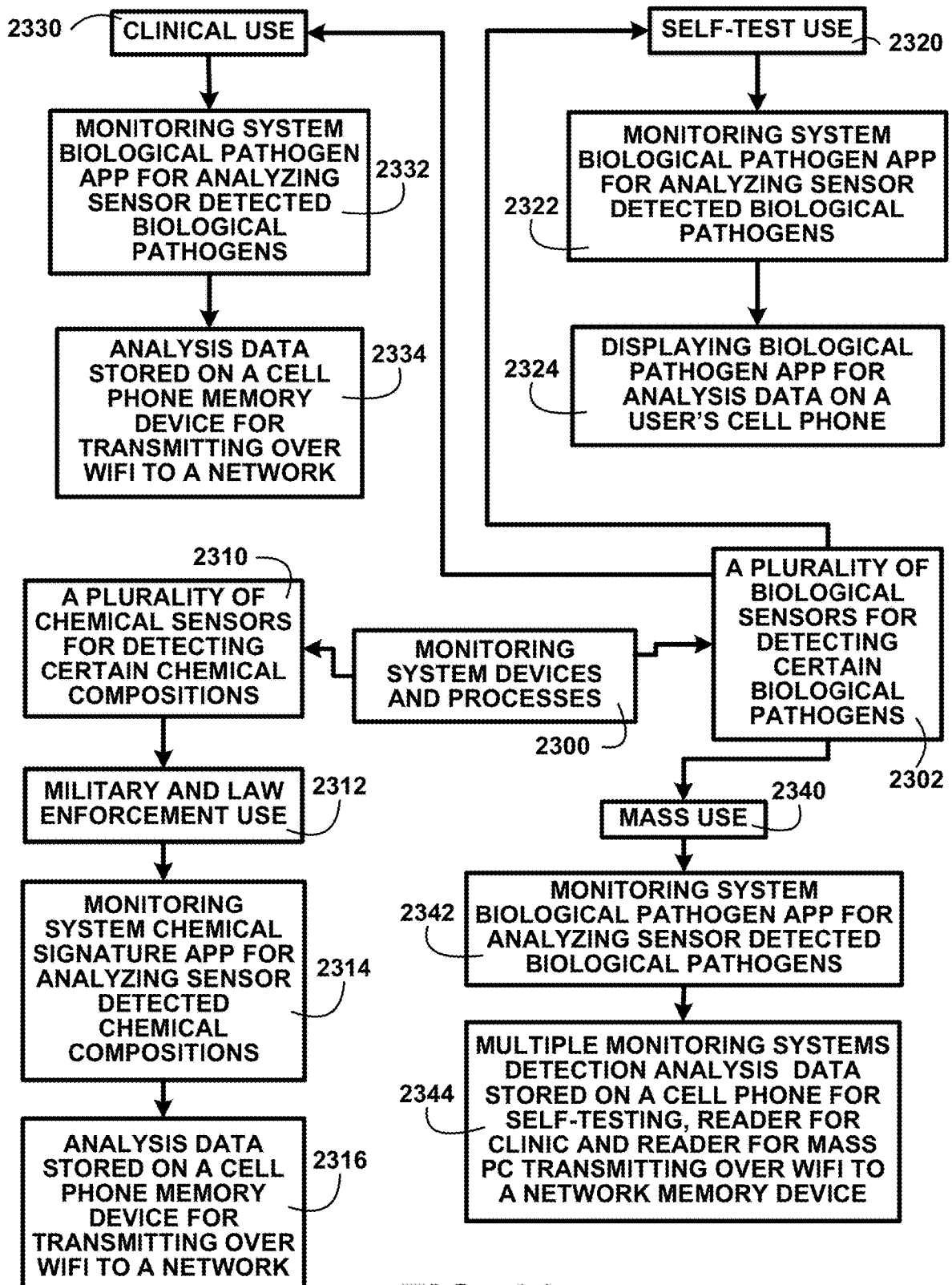
FIG. 23 shows a block diagram of an overview of a monitoring system device and processes of one embodiment.

Monitoring System Devices and Processes:

FIG. 23 shows a block diagram of an overview of monitoring system devices and processes of one embodiment. FIG. 23 shows monitoring system devices and processes 2300 including a plurality of chemical sensors for detecting certain chemical compositions 2310. In one embodiment, the plurality of chemical sensors for detecting certain chemical compositions 2310 are applied for military and law enforcement use 2312. A monitoring system chemical signature app for analyzing sensor detected chemical compositions 2314 is also used for analyzing data stored on a cell phone memory device for transmitting over WIFI to a network 2316.

FIG. 23 shows a plurality of biological sensors for detecting certain biological pathogens 2302. In one embodiment, the plurality of biological sensors for detecting certain biological pathogens 2302 is applied for home use 2320. A monitoring system biological pathogen app for analyzing sensor detected biological pathogens 2322 and for displaying biological pathogen app for analyzing data on a user's cell phone 2324.

In another embodiment, a monitoring system biological pathogen app for analyzing sensor detected biological pathogens 2332 is applied for clinical use 2330. The analysis data stored on a cell phone memory device for transmitting over WIFI to a network 2334. In yet another embodiment a mass use 2340 uses a monitoring system biological pathogen app for analyzing sensor detected biological pathogens 2342. Also uses multiple monitoring systems detection analysis data stored on a cell phone for transmitting over WIFI to a network memory device 2344 of one embodiment.

Figure 24:
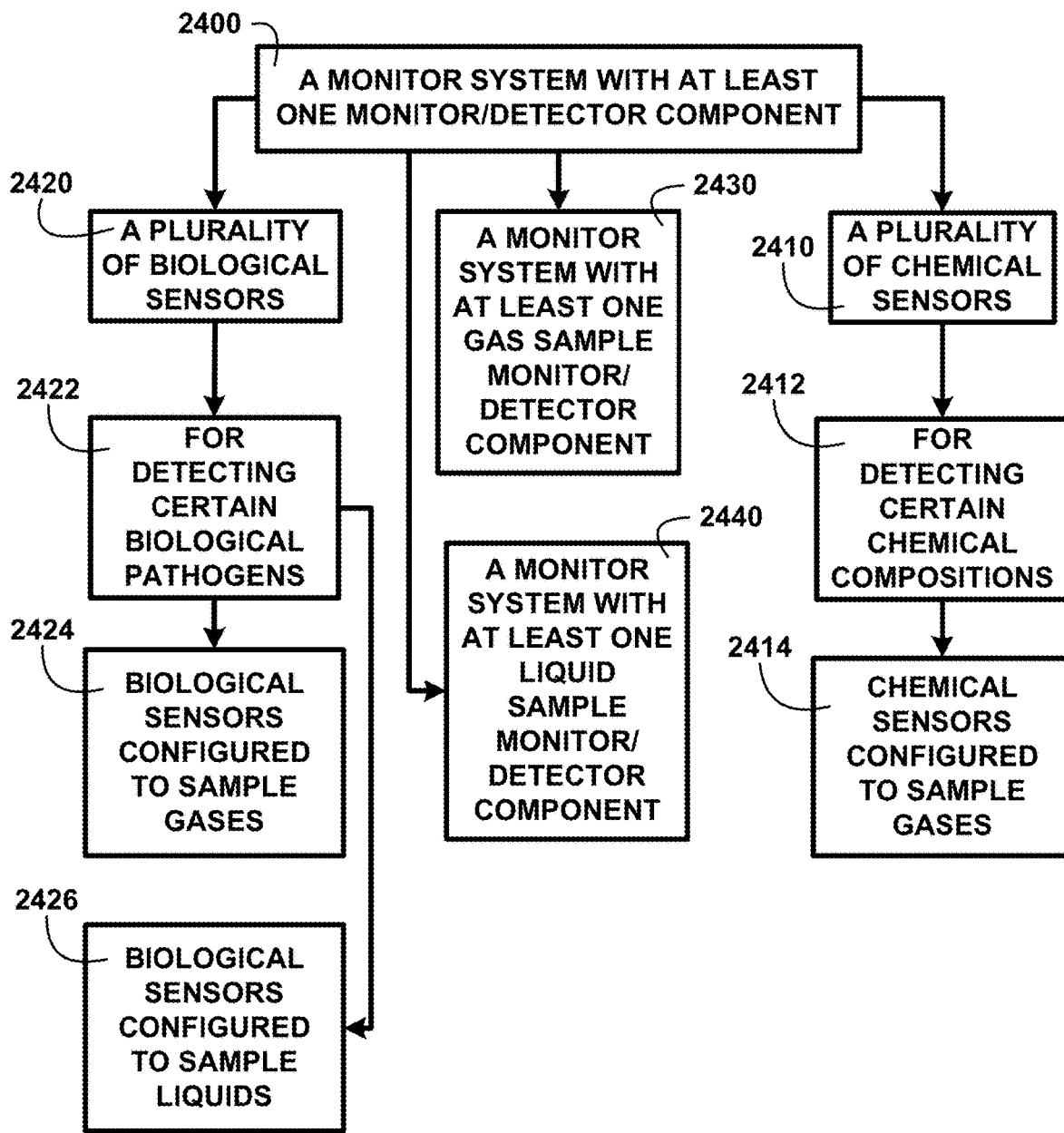
FIG. 24 shows a block diagram of an overview of a monitor/detector component of one embodiment.

Monitor/Detector Component:

FIG. 24 shows a block diagram of an overview of the monitor/detector component of one embodiment. FIG. 24 shows a monitor system with at least one monitor/detector component 2400 with a plurality of chemical sensors 2410 for detecting certain chemical compositions 2412. The plurality of chemical sensors 2410 includes chemical sensors configured to sample gases 2414. The monitor system with at least one monitor/detector component 2400 can be configured with a plurality of biological sensors 2420 for detecting certain biological pathogens 2422. The plurality of biological sensors 2420 includes biological sensors configured to sample gases 2424. The plurality of biological sensors 2420 includes biological sensors configured to sample liquids 2426. The devices include a monitor system with at least one gas sample monitor/detector component 2430. The devices include a monitor system with at least one liquid sample monitor/detector component 2440 of one embodiment.

Figure 25:
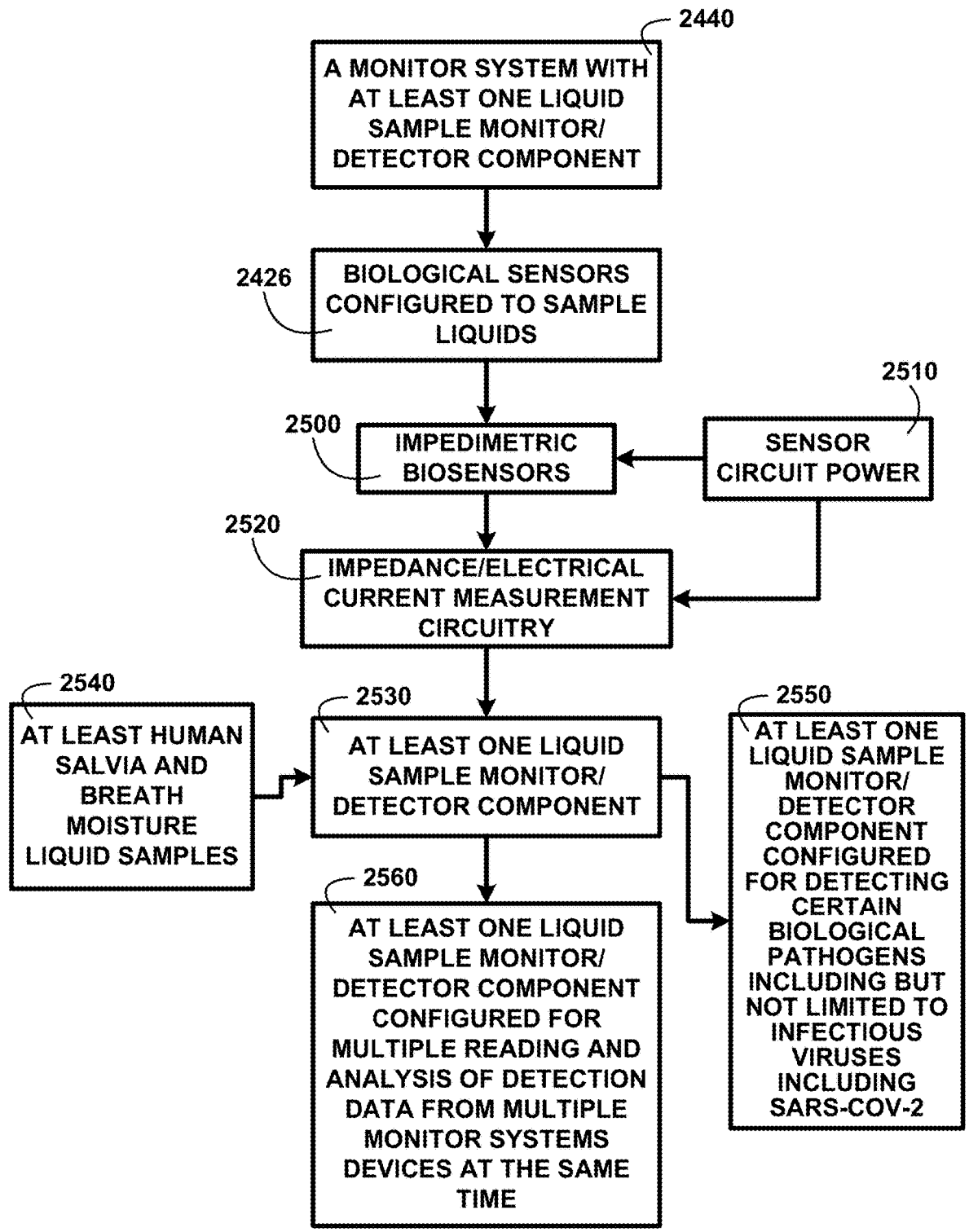
FIG. 25 shows a block diagram of an overview of a liquid sample monitor/detector component of one embodiment.

Liquid Sample Monitor/Detector Component:

FIG. 25 shows a block diagram of an overview of the liquid sample monitor/detector component of one embodiment. FIG. 25 shows a monitor system with at least one liquid sample monitor/detector component 2440 with biological sensors configured to sample liquids 2426. Detection using liquid samples is performed using impedimetric biosensors 2500. The impedimetric biosensors 2500 are powered using sensor circuit power 2510 and use impedance/electrical current measurement circuitry 2520 for an analysis process. At least one liquid sample monitor/detector component 2530 is configured for at least human *salvia*; breathe moisture, and nasopharyngeal liquid samples 2540.

At least one liquid sample monitor/detector component configured for detecting certain biological pathogens including but not limited to infectious viruses including SARS-CoV-2 2550. In another embodiment at least one liquid sample monitor/detector component configured for multiple reading and analysis of detection data from multiple monitor systems devices at the same time 2560 of one embodiment.

Figure 26:
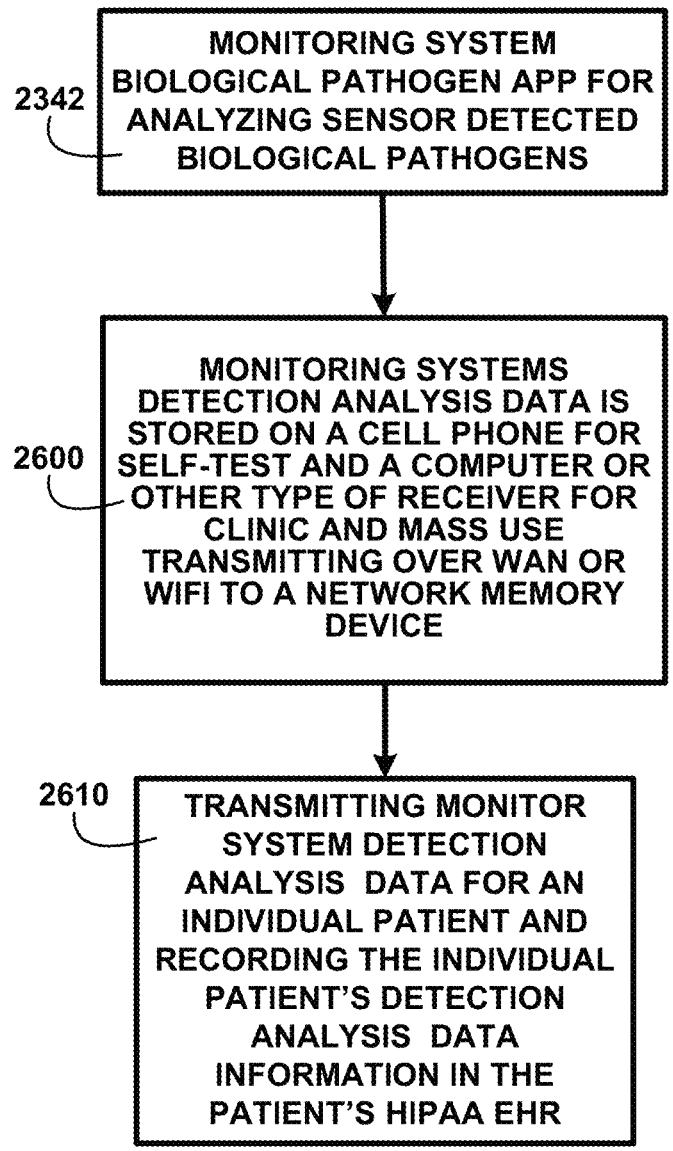
FIG. 26 shows a block diagram of an overview of recording the individual patient's detection analysis data information in the patient's HIPAA EHR of one embodiment.

Recording the Individual Patient's Detection Analysis Data Information in the Patient's HIPAA EHR:

FIG. 26 shows a block diagram of an overview of recording the individual patient's detection analysis data information in the patient's HIPAA EHR of one embodiment. FIG. 26 shows monitoring system biological pathogen app for analyzing sensor detected biological pathogens 2342. Monitoring systems detection analysis data is stored on a cell phone for self-test and a computer or other type of receiver for clinic and mass use transmitting over WAN or WIFI to a network memory device 2600. The process includes transmitting monitor system detection analysis data for an individual patient and recording the individual patient's detection analysis data information in the patient's HIPAA EHR 2610.

Figure 27:
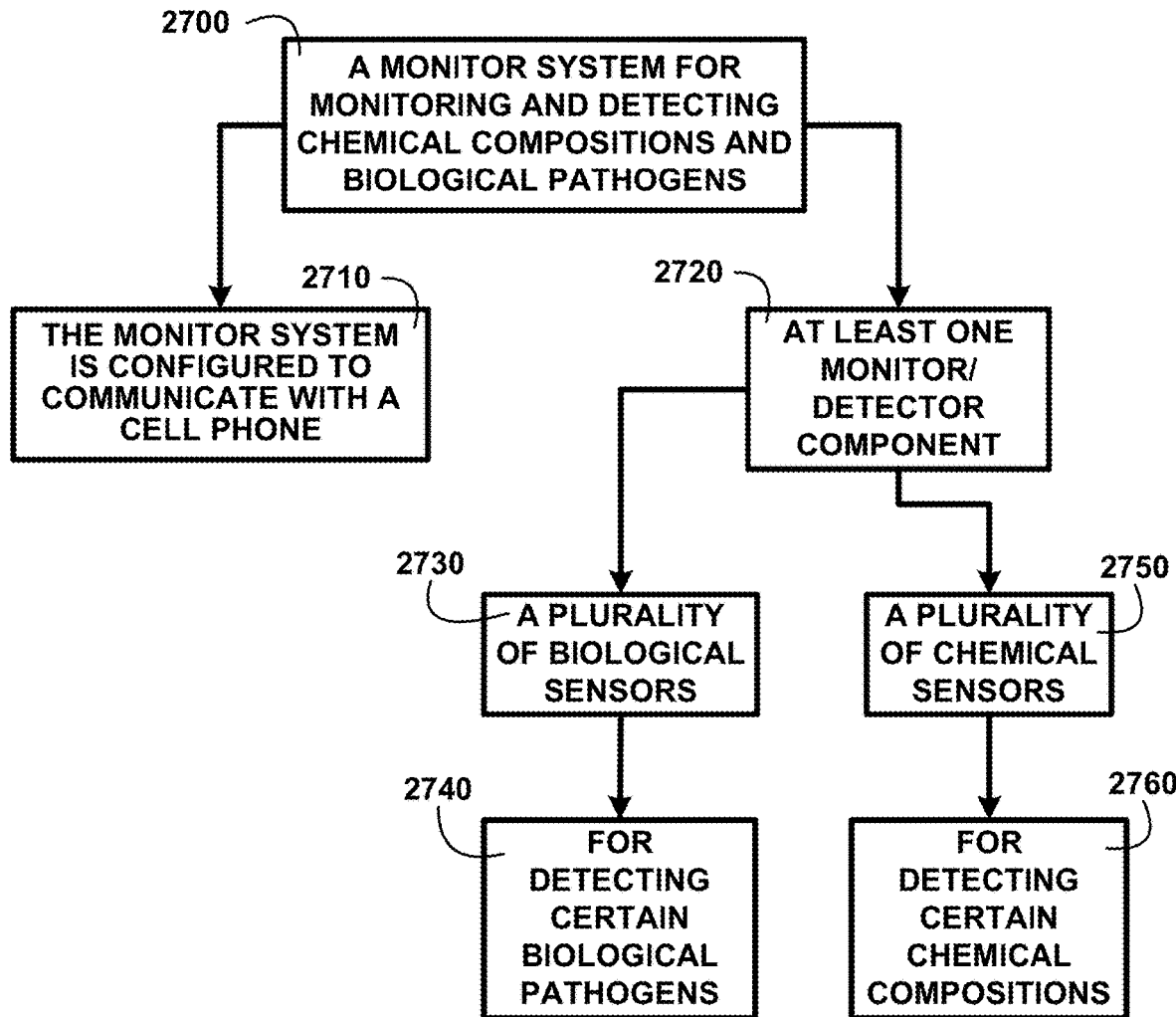
FIG. 27 shows a block diagram of an overview of a monitor system for monitoring and detecting chemical compositions and biological pathogens of one embodiment.

A Monitor System for Monitoring and Detecting Chemical Compositions and Biological Pathogens:

FIG. 27 shows a block diagram of an overview of a monitor system for monitoring and detecting chemical compositions and biological pathogens of one embodiment. FIG. 27 shows a monitor system for monitoring and detecting chemical compositions and biological pathogens 2700. The monitor system is configured to communicate with a cell phone 2710. The monitor system is configured with at least one monitor/detector component 2720. The monitor system is configured with a plurality of biological sensors 2730 for detecting certain biological pathogens 2740. The monitor system is configured with a plurality of chemical sensors 2750 for detecting certain chemical compositions 2760 of one embodiment.

Figure 28:
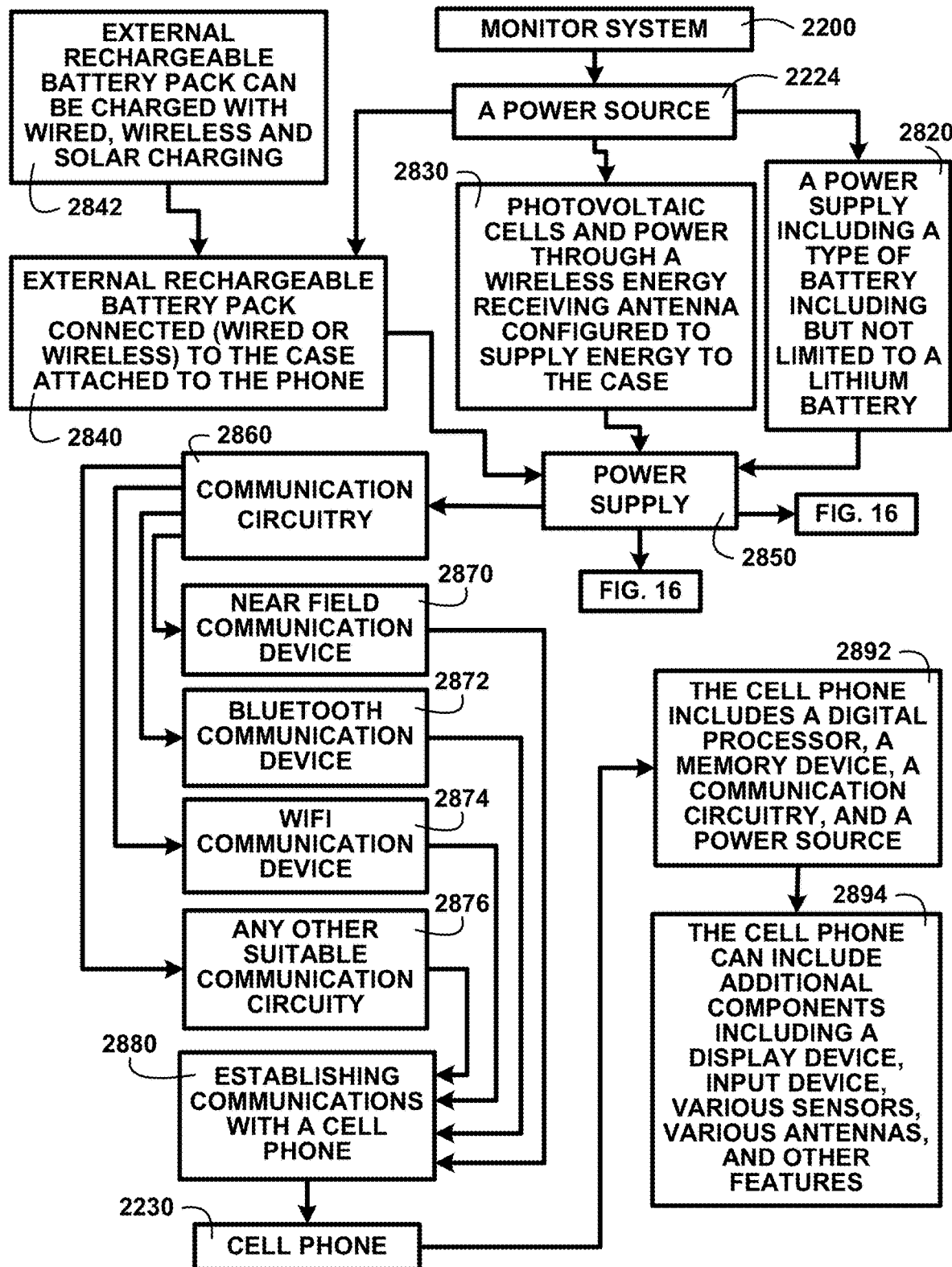
FIG. 28 shows a block diagram of an overview of a power source of one embodiment.

A Power Source:

FIG. 28 shows a block diagram of an overview of a power source of one embodiment. FIG. 28 shows the monitor system 2200 coupled to a power source 2224. The power source 2224 can be configured to include a power supply including a type of battery including but not limited to a lithium battery 2820. The power source 2224 can be configured to include photovoltaic cells and power through a wireless energy receiving antenna configured to supply energy to case 2830. The power source 2224 can be configured to include an external rechargeable battery pack connected (wired or wireless) to the case attached to the phone 2840. The external rechargeable battery pack can be charged with wired, wireless, and solar charging 2842.

The power source 2224 is configured to be a power supply 2850 as shown in FIG. 16. The power source 2224 is configured to be a power supply 2850 for communication circuitry 2860. Communication circuitry 2860 can be configured to include one or more from a group including a near field communication device 2870, Bluetooth® communication device 2872, WIFI communication device 2874, and any other suitable communication circuitry 2876. The communication circuitry 2860 is used for establishing communications with a cell phone 2880. A cell phone 2230 or other communication device is the communication link to the user. The cell phone includes a digital processor, a memory device, a communication circuitry, and a power source 2892. The cell phone 2230 can include additional components including a display device, input device, various sensors, various antennas, and other features 2894 of one embodiment.

Figure 29:
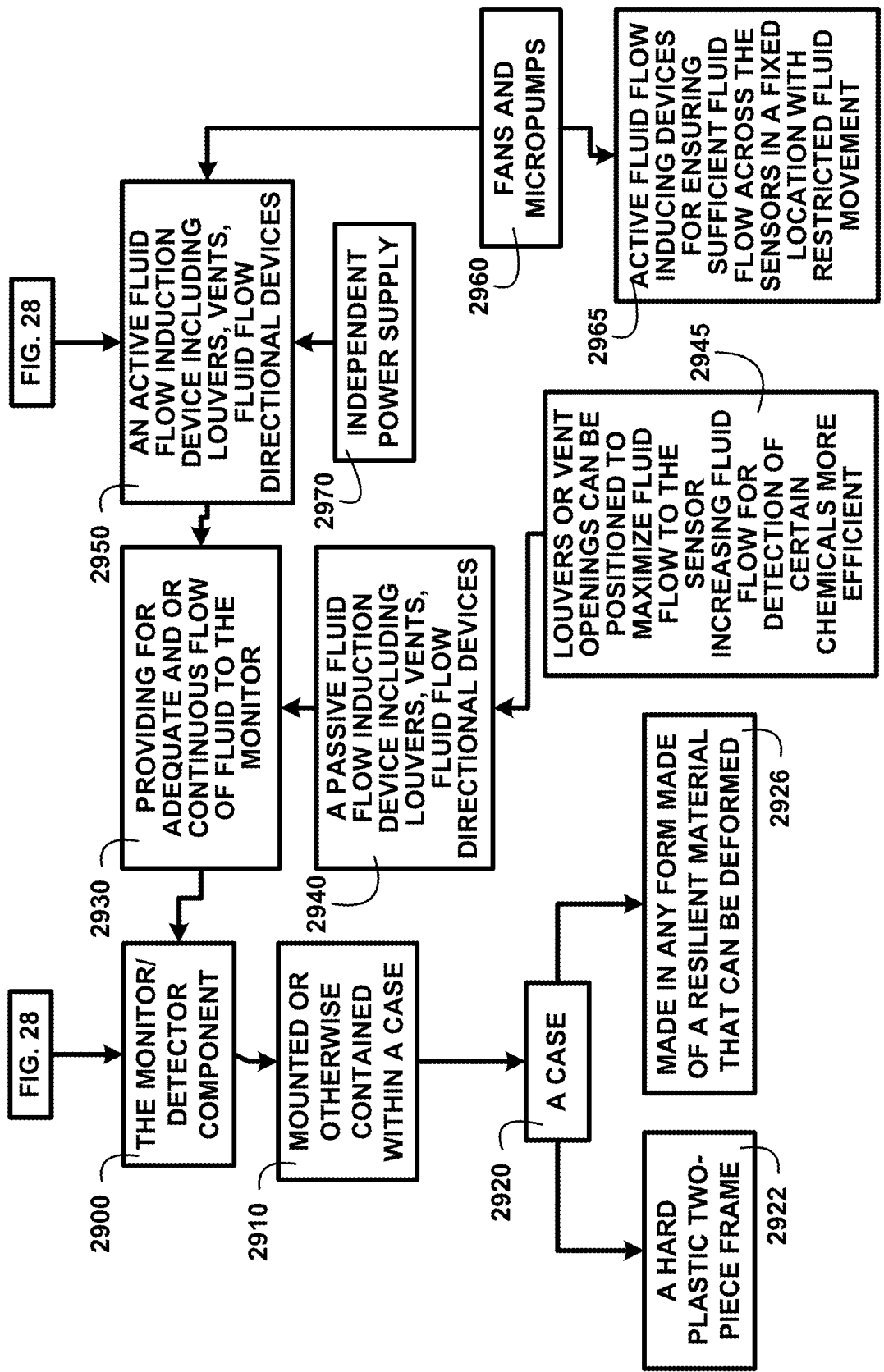
FIG. 29 shows a block diagram of an overview of an airflow induction device of one embodiment.

A Fluid Flow Induction Device:

FIG. 29 shows a block diagram of an overview of a fluid flow induction device of one embodiment. FIG. 29 shows a continuation from FIG. 28 the monitor/detector component 2900 mounted or otherwise contained within a case 2910. A case can be made of a hard plastic two-piece frame 2922. A case 2920 can be made in any form made of a resilient material that can be deformed 2926. A fluid flow induction device is used for providing for adequate and or continuous flow of fluid to monitor 2930. A passive fluid flow induction device including louvers, vents, fluid flow directional devices 2940. Louvers or vent openings can be positioned to maximize fluid flow to the sensor increasing fluid flow for detection of certain chemicals more efficient 2945.

Also continuing from FIG. 28 is showing an active fluid flow induction device including louvers, vents, fluid flow directional devices 2950 with an independent power supply 2970, fans and micro-pumps 2960, and active fluid flow inducing devices for ensuring sufficient fluid flow across the sensors in a fixed location with restricted fluid movement 2965 of one embodiment.

Figure 30:
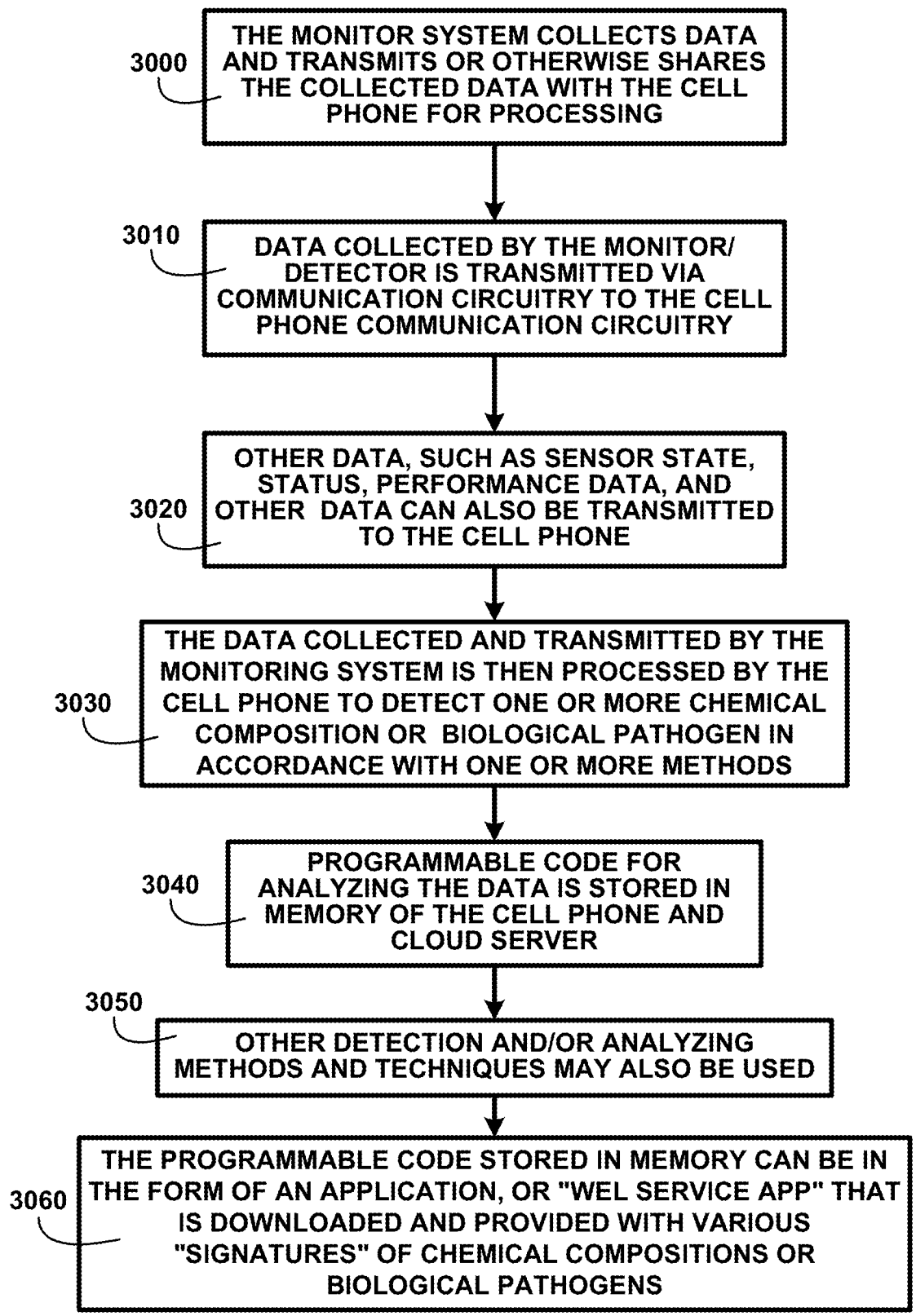
FIG. 30 shows a block diagram of an overview of a cell phone for processing of one embodiment.

A Cell Phone for Processing:

FIG. 30 shows a block diagram of an overview of a cell phone for processing of one embodiment. FIG. 30 shows the monitor system collects data and transmits or otherwise shares the collected data with the cell phone for processing 3000. The data collected by the monitor/detector is transmitted via communication circuitry to the cell phone communication circuitry 3010. Other data, such as sensor state, status, performance data, and other data can also be transmitted to the cell phone 3020. The data collected and transmitted by the monitoring system is then processed by the cell phone to detect one or more chemical composition or biological pathogen in accordance with one or more methods 3030.

Programmable code for analyzing the data is stored in the memory of the cell phone 3040. Other detection and/or analyzing methods and techniques may also be used 3050 The programmable code stored in memory can be in the form of an application, or "app", that is downloaded and provided with various "signatures" of chemical compositions or biological pathogens 3060 of one embodiment.

Figure 31:
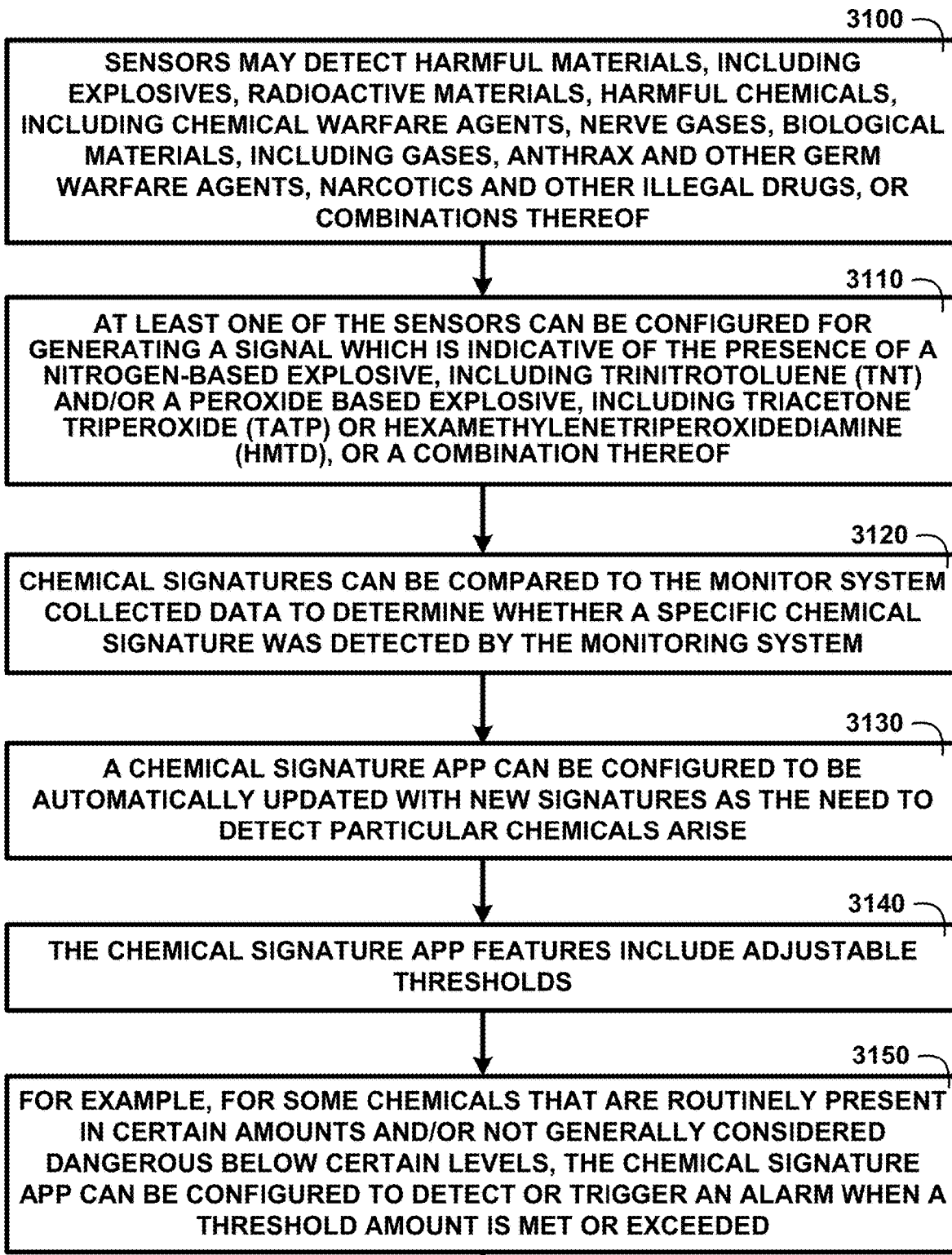
FIG. 31 shows a block diagram of an overview of sensors that may detect harmful materials of one embodiment.

Sensors May Detect Harmful Materials:

FIG. 31 shows a block diagram of an overview of sensors that may detect harmful materials of one embodiment. FIG. 31 shows sensors may detect unwanted or harmful materials, including explosives, radioactive materials, harmful chemicals, including chemical warfare agents, nerve gases, biological materials, including gases, anthrax, and other germ warfare agents, narcotics, other illegal drugs, and unwanted materials, or combinations thereof 3100. At least one of the sensors can be configured for generating a signal which is indicative of the presence of a nitrogen-based explosive, including trinitrotoluene (TNT) and/or a peroxide-based explosive, including triacetone triperoxide (TATP) or hexamethylenetriperoxidediamine (HMTD), or a combination thereof 3110.

Chemical signatures can be compared to the monitor system collected data to determine whether a specific chemical signature was detected by the monitoring system 3120. A chemical signature app can be configured to be automatically updated with new signatures as the need to detect particular chemicals arise 3130. The chemical signature app features include adjustable thresholds 3140, for example, for some chemicals that are routinely present in certain amounts and/or not generally considered dangerous below certain levels, the chemical signature app can be configured to detect or trigger an alarm when a threshold amount is met or exceeded 3150. The description is continued in FIG. 32.

Figure 32:
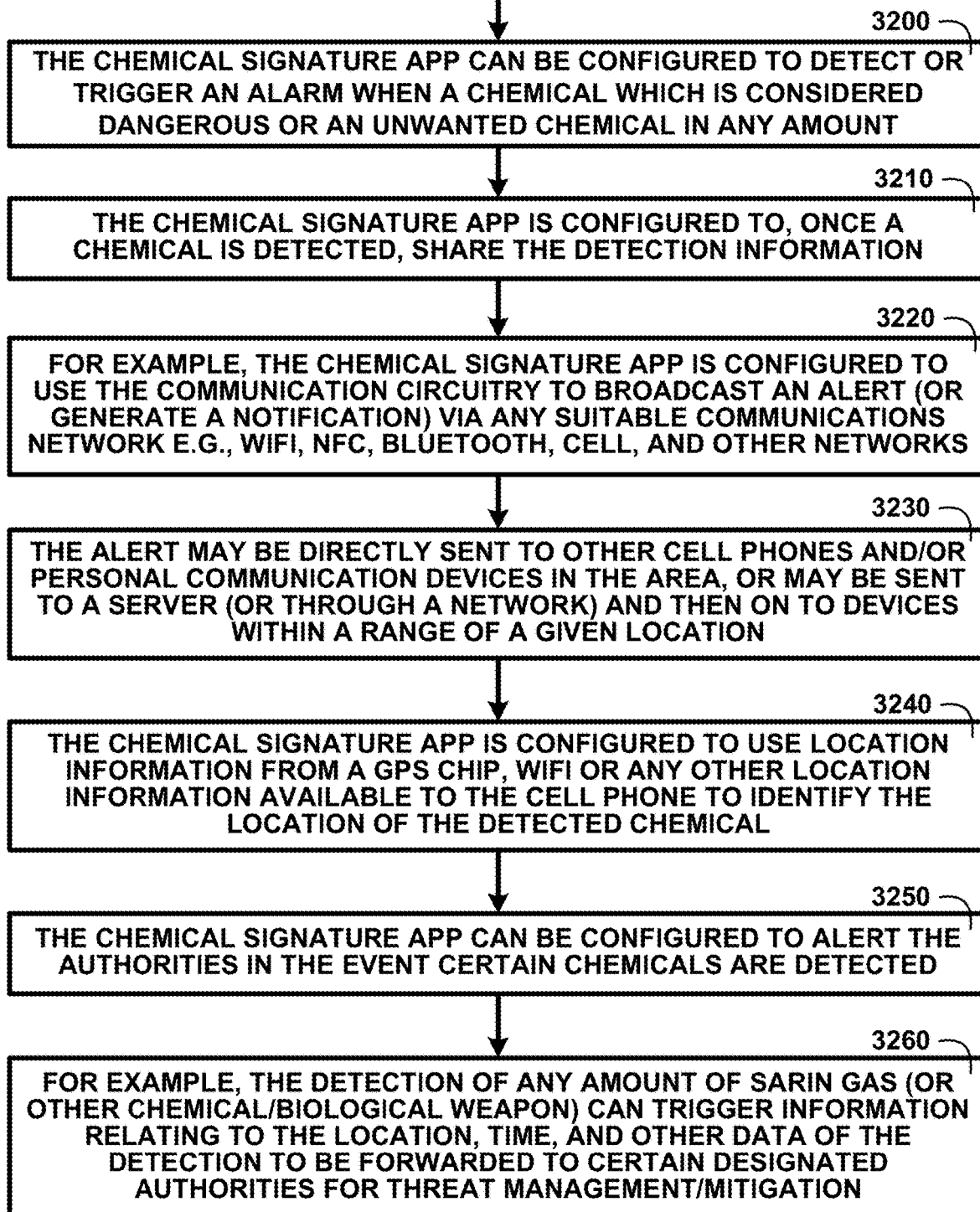
FIG. 32 shows a block diagram of an overview of a chemical signature app of one embodiment.

A Chemical Signature App:

FIG. 32 shows a block diagram of an overview of a chemical signature app of one embodiment. FIG. 32 shows a continuation from FIG. 31 shows the chemical signature app can be configured to detect or trigger an alarm when a chemical which is considered dangerous or an unwanted chemical in any amount 3200. The chemical signature app is configured to, once a chemical is detected, share the detection information 3210, for example, the chemical signature app is configured to use the communication circuitry to broadcast an alert (or generate a notification) via any suitable communications network e.g., WIFI, NFC, Bluetooth®, cell, and other networks 3220. The alert may be directly sent to other cell phones and/or personal communication devices in the area, or may be sent to a server (or through a network) and then on to devices within a range of a given location 3230.

The chemical signature app is configured to use location information from a GPS chip, WIFI, or any other location information available to the cell phone to identify the location of the detected chemical 3240. The chemical signature app can be configured to alert the authorities in the event certain chemicals are detected 3250, for example, the detection of any amount of sarin gas (or other chemical/biological weapons) can trigger information relating to the location, time, and other data of the detection to be forwarded to certain designated authorities for threat management/mitigation 3260 of one embodiment.

Figure 33:
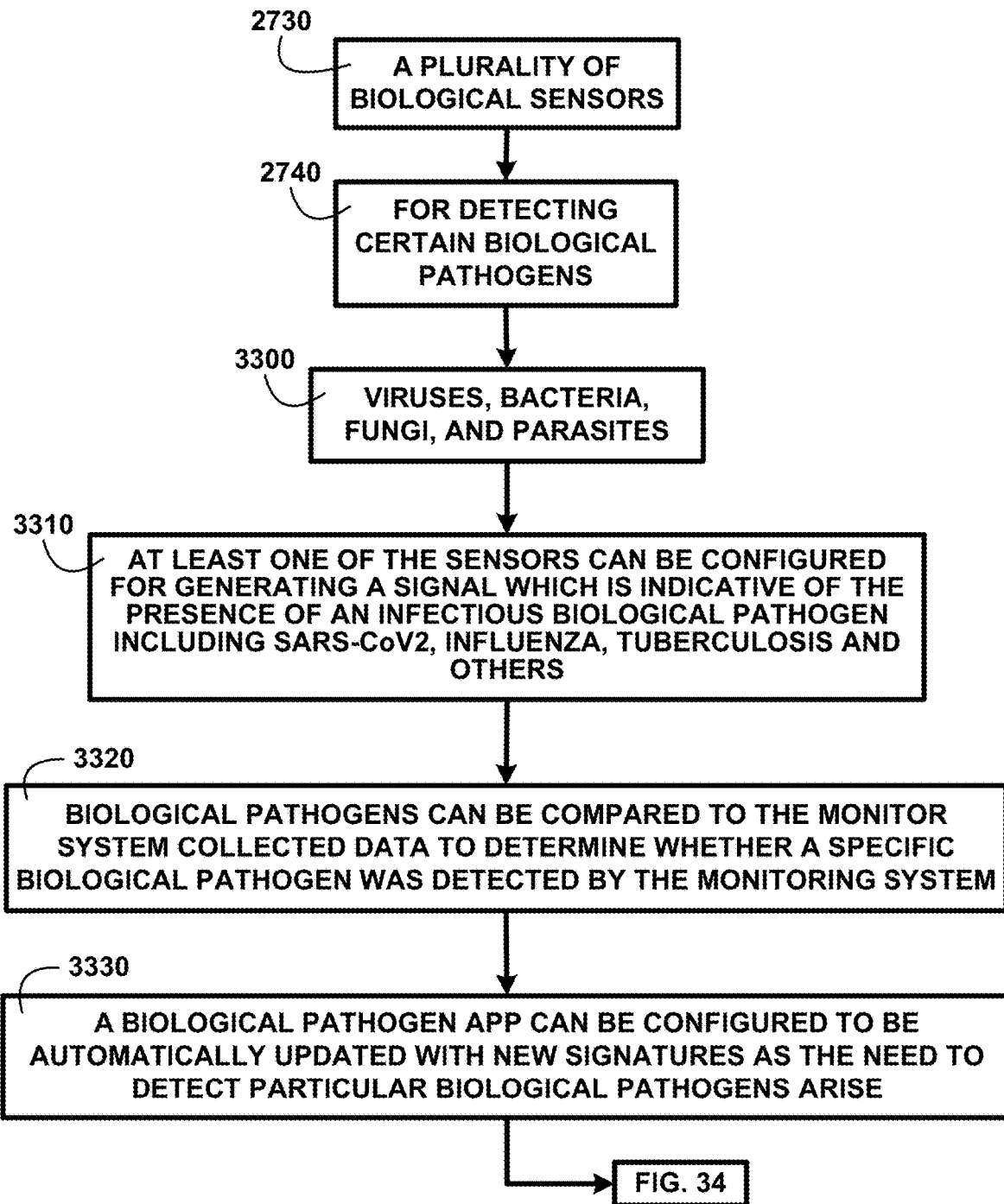
FIG. 33 shows a block diagram of an overview of a biological pathogen app of one embodiment.

A Biological Pathogen App:

FIG. 33 shows a block diagram of an overview of a biological pathogen app of one embodiment. FIG. 33 shows a plurality of biological sensors 2730 for detecting certain biological pathogens 2740 including viruses, bacteria, fungi, and parasites 3300. At least one of the sensors can be configured for generating a signal which is indicative of the presence of an infectious biological pathogen including SARS-CoV-2, influenza, tuberculosis, and others 3310. Biological pathogens can be compared to the monitor system collected data to determine whether a specific biological pathogen was detected by the monitoring system 3320. A biological pathogen app can be configured to be automatically updated with new signatures as the need to detect particular biological pathogens arise 3330. The description is continued in FIG. 34.

Communication Circuitry to Broadcast an Alert:

FIG. 34 shows a block diagram of an overview of communication circuitry to broadcast an alert of one embodiment. FIG. 34 shows a continuation from FIG. 33 the biological pathogen app can be configured to detect or trigger an alarm when a pathogen that is considered highly infectious is detected 3400. The biological pathogen app is configured to, once a highly infectious pathogen is detected, share the detection information 3410, for example, the biological pathogen app is configured to use the communication circuitry to broadcast an alert (or generate a notification) via any suitable communications network e.g., WIFI, NFC, Bluetooth®, cell, and other networks 3420. The alert may be directly sent to other cell phones and/or personal communication devices in the area, or may be sent to a server (or through a network) and then on to devices within a range of a given location 3430. The biological pathogen app is configured to use location information from a gps chip, wifi or any other location information available to the cell phone to identify the location of the detected highly infectious pathogen 3440. The biological pathogen app can be configured to alert the authorities in the event certain highly infectious pathogens are detected 3450. For example, the detection of sars-cov-2 can trigger information relating to the location, time, and other data of the detection to be forwarded to certain designated authorities for public health threat management/mitigation 3460 of one embodiment.

Figure 35:
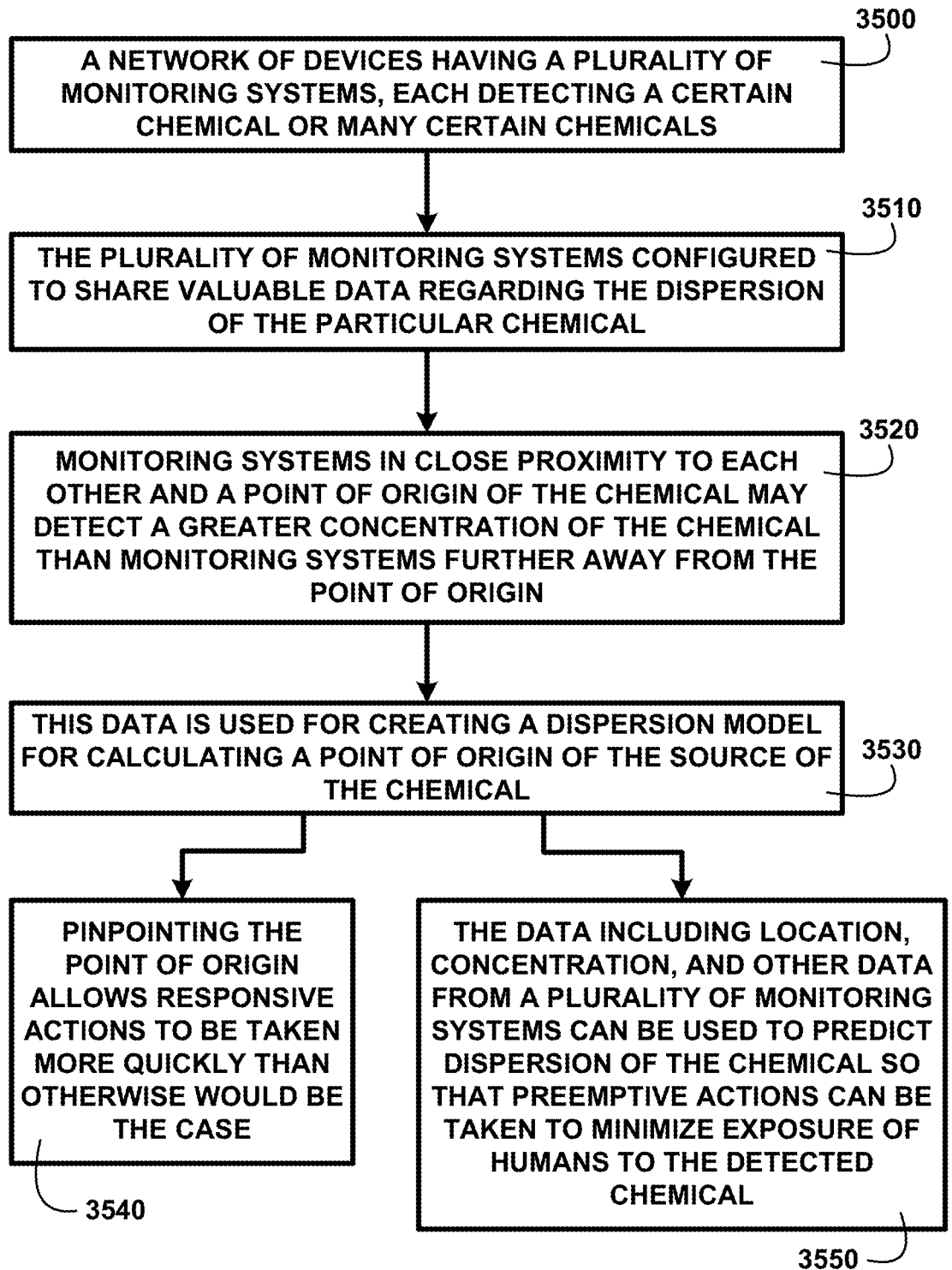
FIG. 35 shows a block diagram of an overview of a network of devices having a plurality of monitoring systems of one embodiment.

A Network of Devices Having a Plurality of Monitoring Systems:

FIG. 35 shows for illustrative purposes only an example of a network of devices having a plurality of monitoring systems of one embodiment. FIG. 35 shows a network of devices having a plurality of monitoring systems, each detecting a certain chemical 3500. The plurality of monitoring systems configured to share valuable data regarding the dispersion of the particular chemical 3510. Monitoring systems in close proximity to each other and a point of origin of the chemical may detect a greater concentration of the chemical than monitoring systems further away from the point of origin 3520.

This data is used for creating a dispersion model for calculating a point of origin of the source of the chemical 3530. Pinpointing the point of origin allows responsive actions to be taken more quickly than otherwise would be the case 3540. The data including location, concentration, and other data from a plurality of monitoring systems can be used to predict the dispersion of the chemical so that preemptive actions can be taken to minimize exposure of humans to the detected chemical 3550 of one embodiment.

Figure 36:
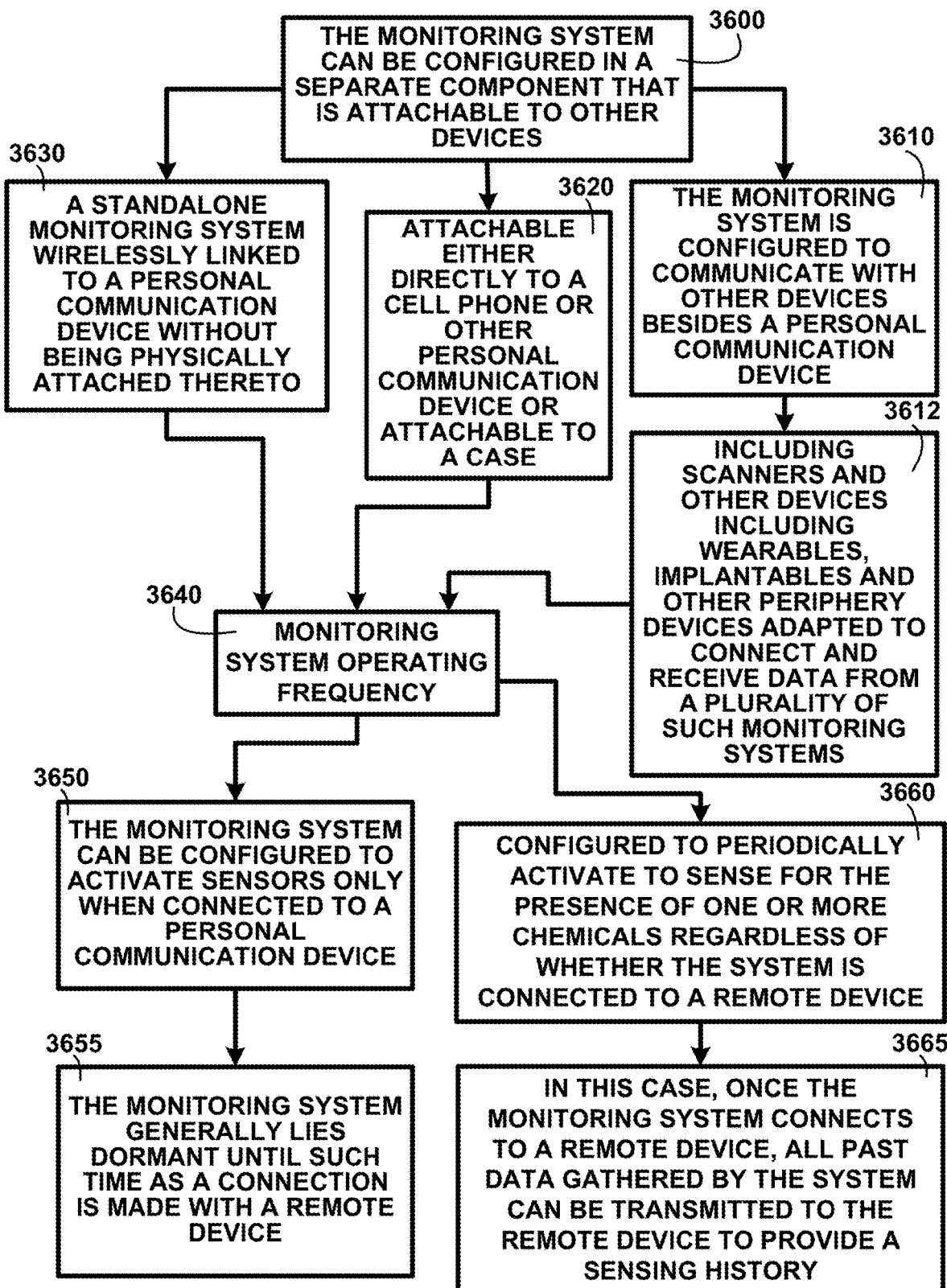
FIG. 36 shows a block diagram of an overview of the monitoring system configured in a separate component of one embodiment.

The Monitoring System Configured in a Separate Component:

FIG. 36 shows a block diagram of an overview of the monitoring system configured in a separate component of one embodiment. FIG. 36 shows the monitoring system can be configured in a separate component that is attachable to other devices 3600. The monitoring system is configured to communicate with other devices besides a personal communication device 3610 including scanners and other devices adapted to connect and receive data from a plurality of such monitoring systems 3612.

The monitoring system is attachable either directly to a cell phone or other personal communication device or attachable to a case 3620. A standalone monitoring system wirelessly linked to a personal communication device without being physically attached thereto 3630 can be used. The monitoring system operating frequency 3640 can be varied for a particular use. The monitoring system can be configured to activate sensors only when connected to a personal communication device 3650.

In this operating frequency, the monitoring system generally lies dormant until a connection is made with a remote device 3655. The monitoring system operating frequency 3640 can be configured to periodically activate to sense for the presence of one or more chemicals regardless of whether the system is connected to a remote device 3660. In this case, once the monitoring system connects to a remote device, all past data gathered by the system can be transmitted to the remote device to provide a sensing history 3665 of one embodiment.

Figure 37:
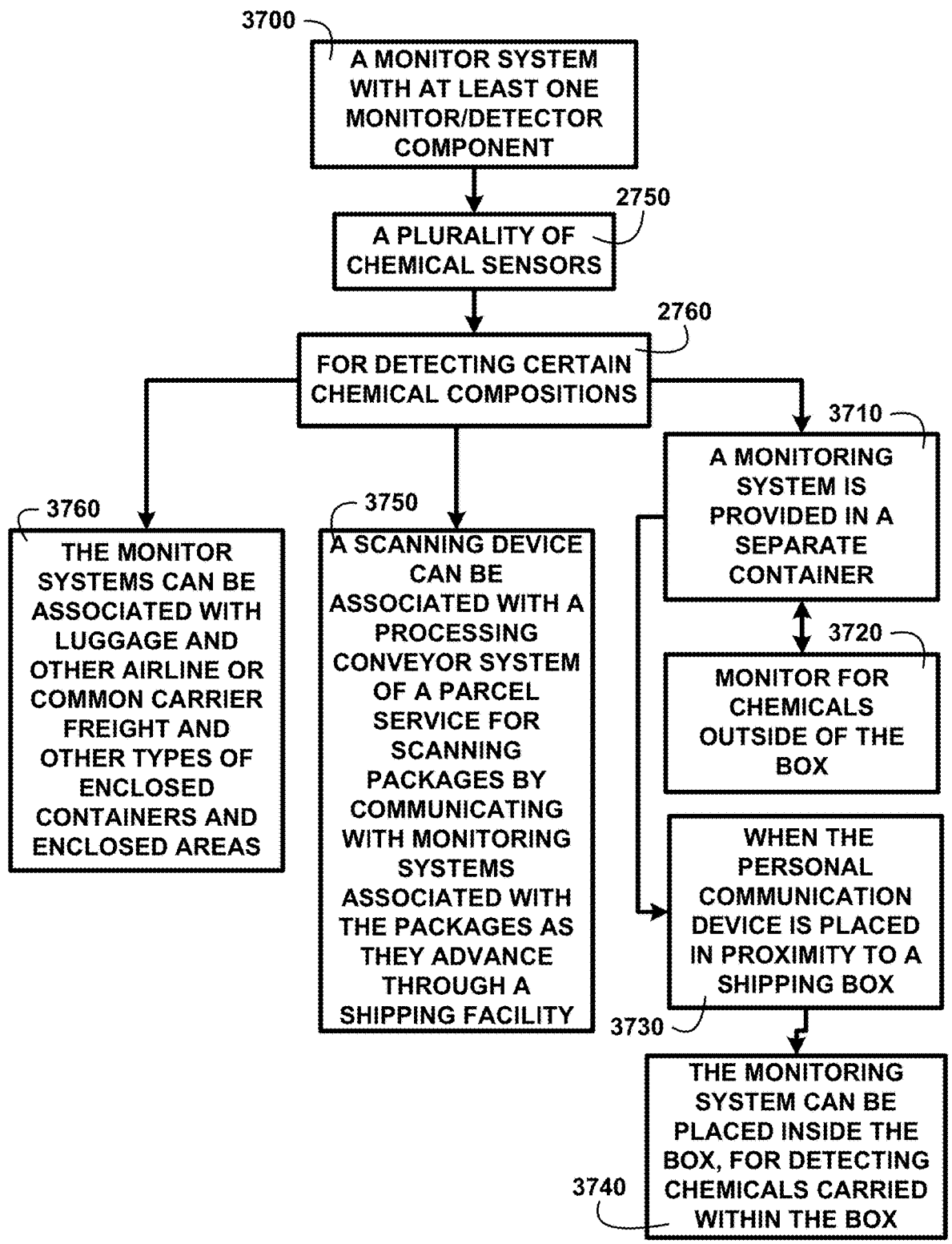
FIG. 37 shows a block diagram of an overview of a scanning device of one embodiment.

A Scanning Device:

FIG. 37 shows a block diagram of an overview of a scanning device of one embodiment. FIG. 37 shows a monitor system with at least one monitor/detector component 3700 and a plurality of chemical sensors 2750 for detecting certain chemical compositions 2760. A monitoring system is provided in a separate container 3710 to monitor for chemicals outside of the box 3720.

When the personal communication device is placed in proximity to a shipping box 3730 the monitoring system transmits the data to the personal communication device. The monitoring system can be placed inside the box, for detecting chemicals carried within the box 3740. A scanning device can be associated with a processing conveyor system of a parcel service for scanning packages by communicating with monitoring systems associated with the packages as they advance through a shipping facility 3750. The monitor systems can be associated with luggage and other airline or common carrier freight and other types of enclosed containers and enclosed areas 3760 of one embodiment.

Figure 38:
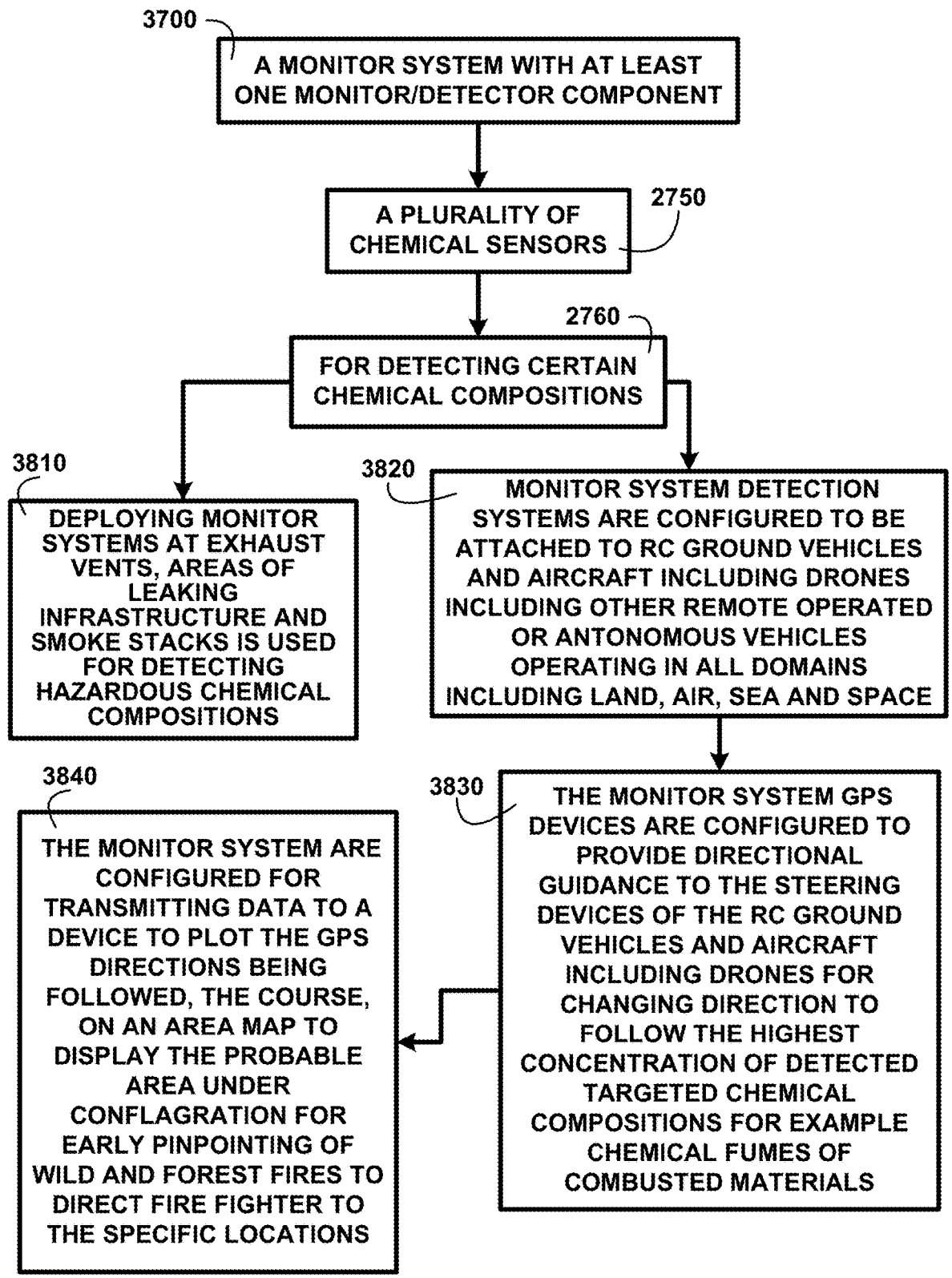
FIG. 38 shows a block diagram of an overview of RC ground vehicles and aircraft of one embodiment.

RC Ground Vehicles and Aircraft:

FIG. 38 shows a block diagram of an overview of RC ground vehicles and aircraft of one embodiment. FIG. 38 shows a monitor system with at least one monitor/detector component 3700 and a plurality of chemical sensors 2750 for detecting certain chemical compositions 2760. In one embodiment deploying monitor systems at exhaust vents, areas of leaking infrastructure and smokestacks is used for detecting hazardous chemical compositions 3810. Monitor system detection systems are configured to be attached to RC ground vehicles and aircraft including drones 3820.

The monitor system GPS devices are configured to provide directional guidance to the steering devices of the RC ground vehicles and aircraft including drones for changing direction to follow the highest concentration of detected targeted chemical compositions for example chemical fumes of combusted materials 3830. The monitor system is configured for transmitting data to a device to plot the GPS directions being followed, the course, on an area map to display the probable area under conflagration for early pinpointing of wild and forest fires to direct firefighter to the specific locations 3840 of one embodiment.

Figure 39:
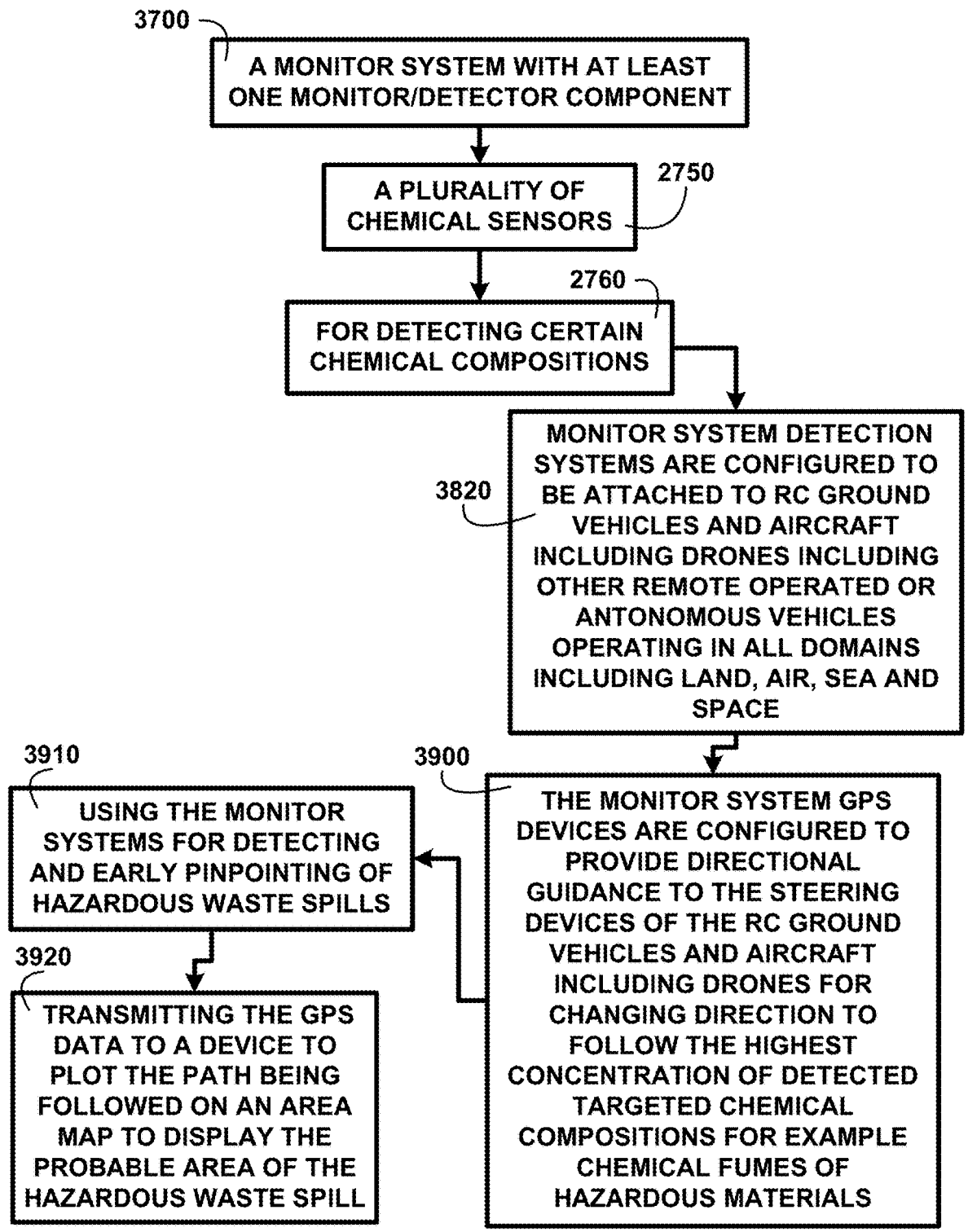
FIG. 39 shows a block diagram of an overview of directional guidance to the steering devices of one embodiment.

Directional Guidance to the Steering Devices:

FIG. 39 shows a block diagram of an overview of directional guidance to the steering devices of one embodiment. FIG. 39 shows a monitor system with at least one monitor/detector component 3700 with a plurality of chemical sensors 2750 for detecting certain chemical compositions 2760. Monitor system detection systems are configured to be attached to RC ground vehicles and aircraft including drones 3820. The monitor system GPS devices are configured to provide directional guidance to the steering devices of the RC ground vehicles and aircraft including drones for changing direction to follow the highest concentration of detected targeted chemical compositions for example chemical fumes of hazardous materials 3900. Using the monitor systems for detecting and early pinpointing of hazardous waste spills 3910. The monitor systems are configured for transmitting the GPS data to a device to plot the path being followed on an area map to display the probable area of the hazardous waste spill 3920 of one embodiment.

Figure 40:
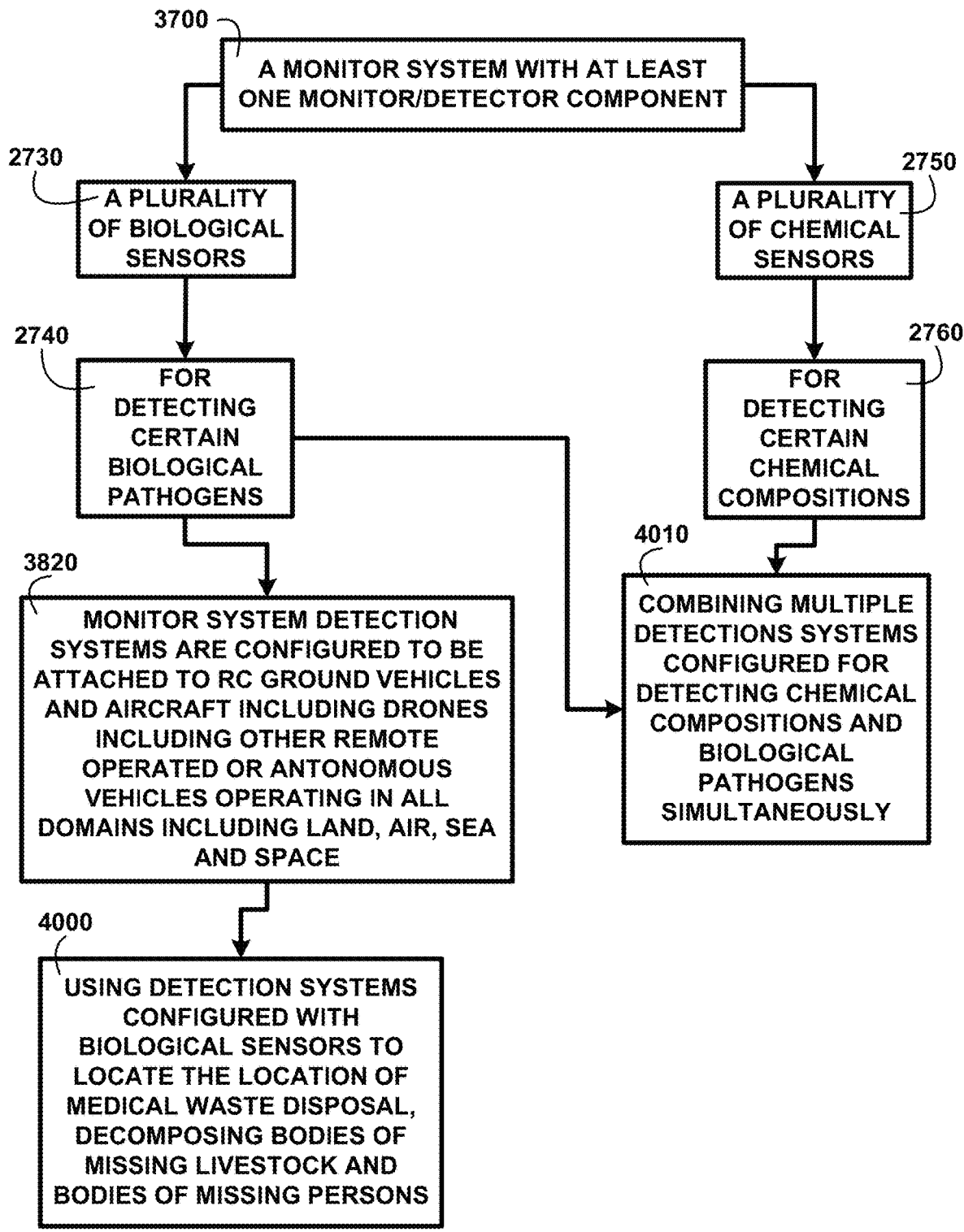
FIG. 40 shows a block diagram of an overview of the location of medical waste disposal of one embodiment.

Location of Medical Waste Disposal:

FIG. 40 shows a block diagram of an overview of the location of medical waste disposal of one embodiment. FIG. 40 shows a monitor system with at least one monitor/detector component 3700 with a plurality of chemical sensors 4050 for detecting certain chemical compositions 4060. In another embodiment, the monitor system is configured with a plurality of biological sensors 4030 for detecting certain biological pathogens 4040. Some applications are configured for combining multiple detection systems configured for detecting chemical compositions and biological pathogens simultaneously 4010.

The plurality of biological sensors 4030 for detecting certain biological pathogens 4040 can be used with the monitor system detection systems is configured to be attached to RC ground vehicles and aircraft including drones 3820. Application includes using detection systems configured with biological sensors to locate the location of medical waste disposal, decomposing bodies of missing livestock, and bodies of missing persons 4000 of one embodiment.

Figure 41:
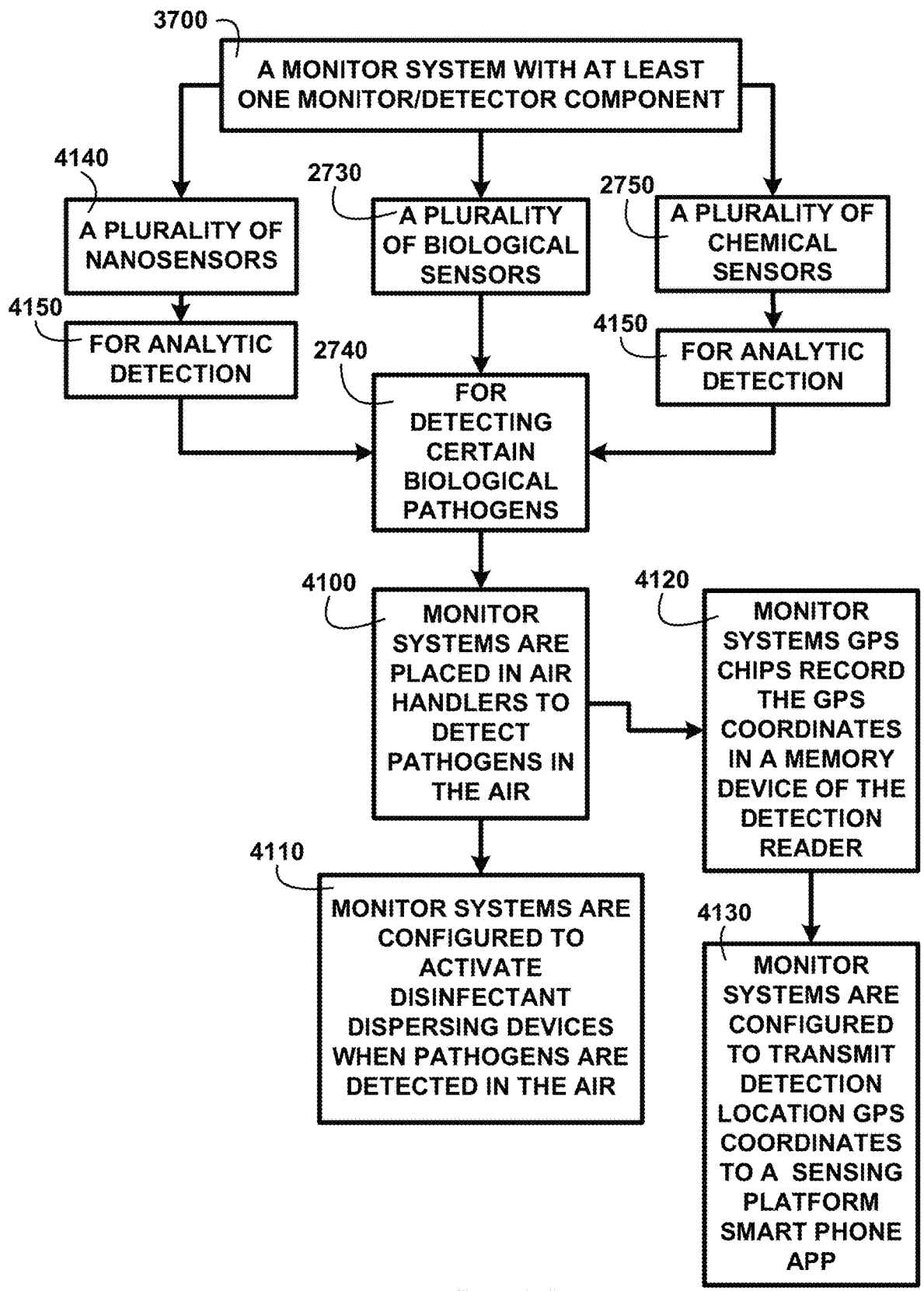
FIG. 41 shows a block diagram of an overview of monitor systems are placed in air handlers of one embodiment.

Monitor Systems are Placed in Air Handlers:

FIG. 41 shows a block diagram of an overview of monitor systems are placed in air handlers of one embodiment. FIG. 41 shows a monitor system with at least one monitor/detector component 3700 with a plurality of biological sensors 2730 for detecting certain biological pathogens 2740. A plurality of nanosensors 4140 for analytic detection 4150. A plurality of chemical sensors 2750 for analytic detection 4150. Monitor systems are placed in air handlers to detect pathogens in the air 4100. Monitor systems are configured to activate disinfectant dispersing devices when pathogens are detected in the air 4110. Monitor systems GPS chips record the GPS coordinates in a memory device of the detection reader 4120. The monitor systems are configured to transmit detection location GPS coordinates to a sensing platform smartphone app 4130 of one embodiment.

Figure 42A:
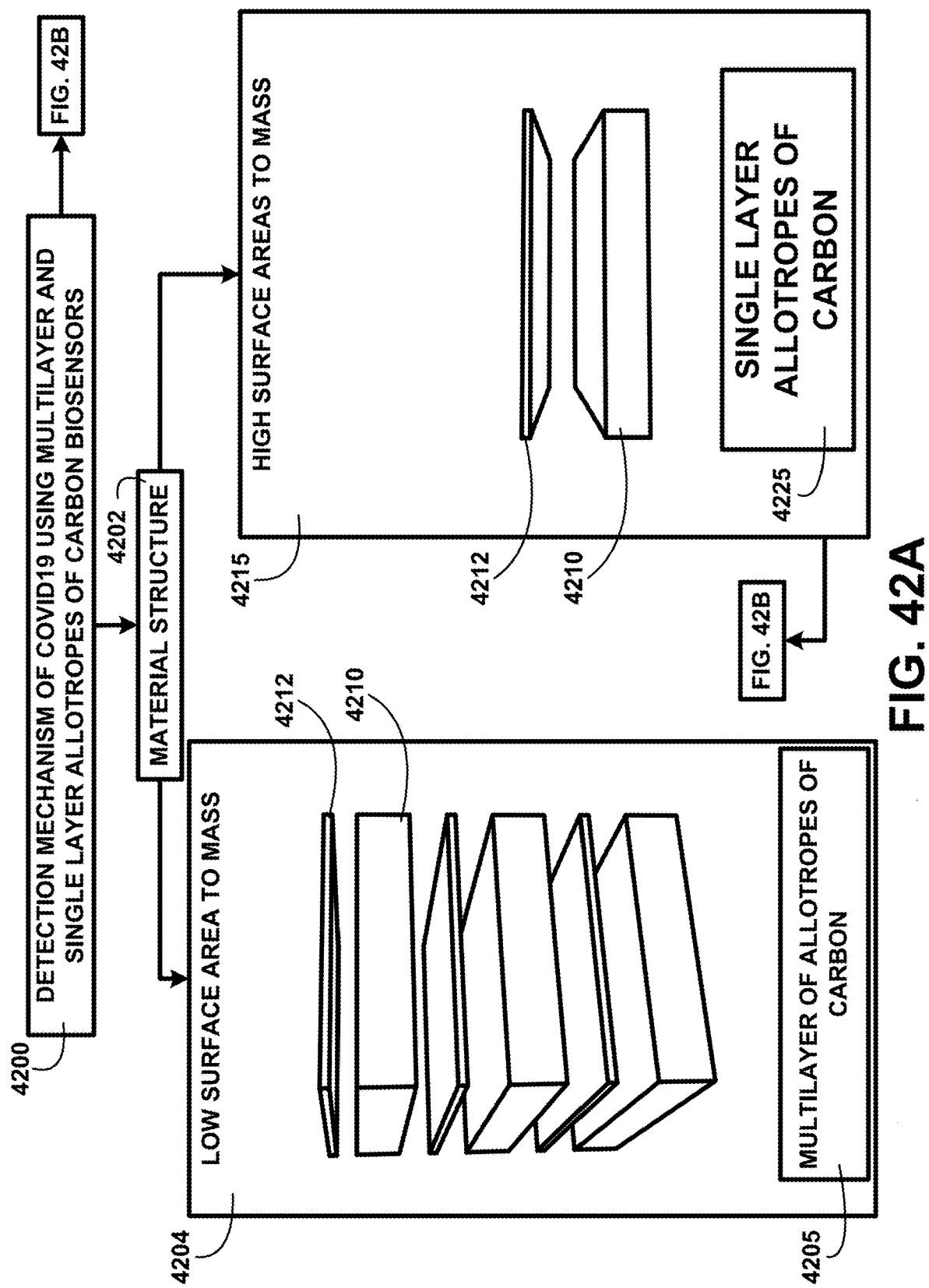
FIG. 42A shows for illustrative purposes only an example of the detection mechanism of COVID-19 using other allotropes of carbon biosensors of one embodiment.

Detection Mechanism of COVID-19 Using Other Allotropes of Carbon Biosensors:

FIG. 42A shows for illustrative purposes only an example of a detection mechanism of COVID-19 using other allotropes of carbon biosensors of one embodiment. FIG. 42A shows a Detection Mechanism of COVID19 using multi-layer and single layer allotropes of carbon biosensors 4200 with a process for generating material structure 4202 of other allotropes of carbon. The allotropes of carbon 4210 are functionalized by adding a layer of biologically sensitive molecules probe 4212. Multilayer of allotropes of carbon 4205 produce a low surface area to mass 4204. Single layer of allotropes of carbon 4225 produce a high surface area to mass 4215. The description continues in FIG. 42B of one embodiment.

Biologically Sensitive Molecules Complementary Pairing:

FIG. 42B shows for illustrative purposes only an example of a complementary pairing of biologically sensitive molecules of one embodiment. The complementary pairing is the process of combining two complementary single-stranded DNA or RNA molecules and allowing them to form a single double-stranded molecule through base pairing. FIG. 42B shows a continuation from 42A with a detection mechanism 4228 utilizing a plurality of biologically sensitive molecules probe 4230 and allotropes of carbon 4240. The plurality in this example of biologically sensitive molecules probes 4230 are SARS-CoV-2 biologically sensitive molecules 4250.

The SARS-CoV-2 biologically sensitive molecules 4250 layered onto the allotropes of carbon 4240 molecules stabilized inductively forming a weak electrostatic bond. A plurality of COVID-19 N genes 4260 from the SARS-CoV-2 DNA biologically sensitive molecules 4250 undergoes biologically sensitive molecules 4270. The DNA biologically sensitive molecules 4270 creates ssDNA biologically sensitive molecules functionalized single layer or multilayer allotropes of carbon changing allotropes of carbon conductivity with DNA biologically sensitive molecules 4275. The layers include allotropes of carbon 4210 and a layer of biologically sensitive molecules probe 4212.

The complementary pairing process is orienting the biologically sensitive molecules on the surface of the conductive layer consisting of one from a group of graphene or other allotropes of carbon to ensure that the stronger bond between the biologically sensitive molecules and the target genetic material (RNA of SARS-Cov-2) overpowers the weaker electrostatic bond between the surface of the conductive layer allotrope of carbon and the biologically sensitive molecules of one embodiment.

Figure 43A:
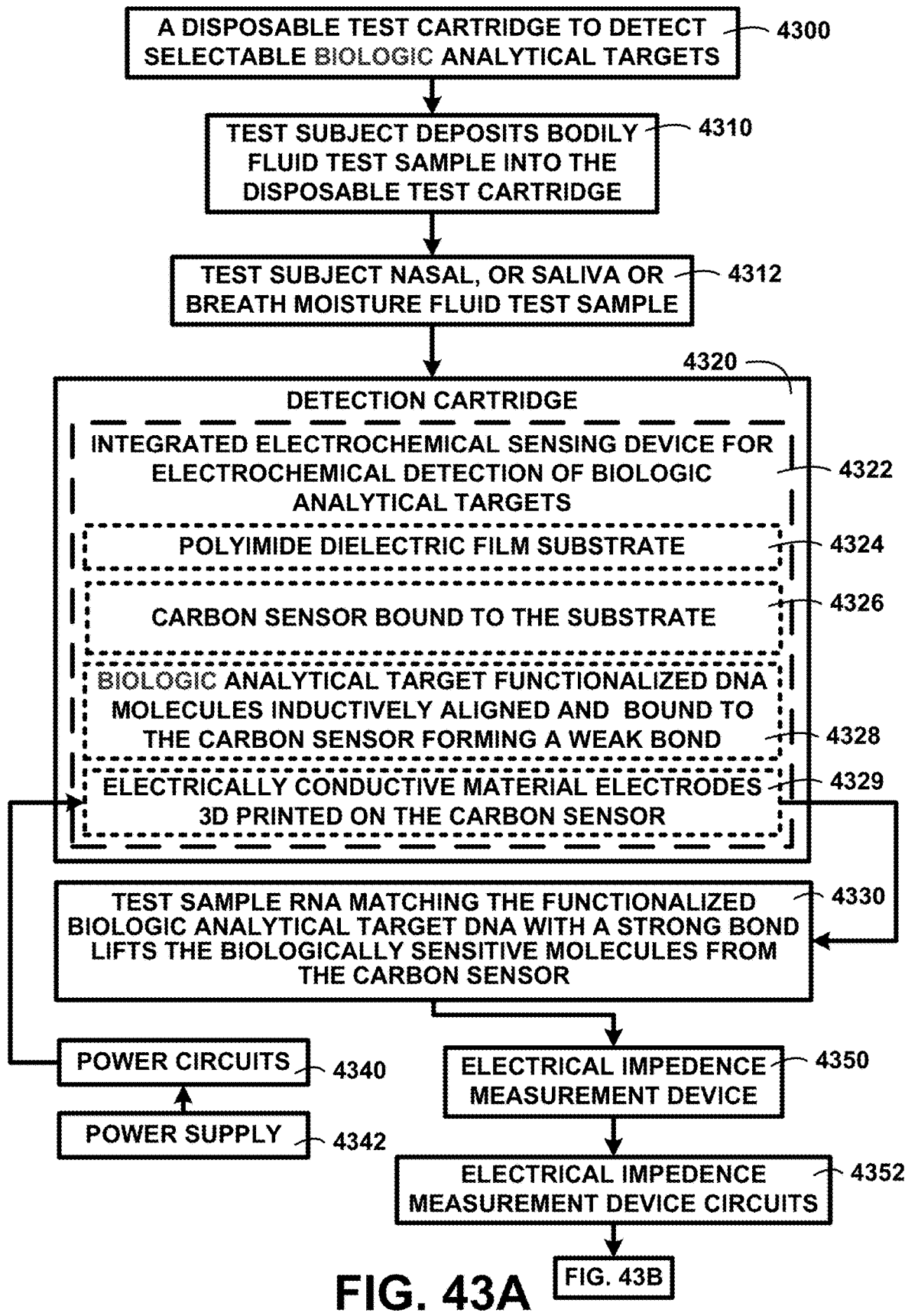
FIG. 43A shows a block diagram of an overview of a disposable detection cartridge of one embodiment.

A Disposable Detection Cartridge:

FIG. 43A shows a block diagram of an overview of a disposable detection cartridge of one embodiment. FIG. 43A shows a disposable detection cartridge to detect selectable biologic analytical targets 4300. A test subject deposits a bodily fluid test sample into the disposable detection cartridge 4310. The bodily fluid test sample may consist of a test subject bodily fluid test sample or nasopharyngeal fluid test sample 4312. The bodily fluid test sample may consist of a test subject breath moisture bodily fluid test sample 4314. The bodily fluid test sample is deposited into the detection cartridge 4320. The bodily fluid test sample comes in contact with an integrated electrochemical sensing device for electrochemical detection of biologic analytical targets 4322.

The integrated electrochemical sensing device for electrochemical detection of biologic analytical targets 4322 comprises a polyimide dielectric film substrate 4324 with a carbon sensor bound to the substrate 4326. The carbon sensor includes biologic analytical target functionalized DNA biologically sensitive molecules inductively aligned and bound to the carbon sensor forming a weak bond 4328. Electrically conductive material electrodes printed on the carbon sensor 4329.

A test sample of biologically sensitive molecules complementary to the functionalized biologic analytical target DNA biologically sensitive molecules with a strong bond lifts the DNA biologically sensitive molecules from the carbon sensor 4330. A power supply 4342 energizes through power circuits 4340 the electrically conductive material electrodes printed on the carbon sensor 4329.

A test sample RNA biologically sensitive molecules complementary to the functionalized biologic analytical target DNA biologically sensitive molecules with a strong bond lifts the DNA biologically sensitive molecules from the carbon sensor 4330. The electrical power in two phases arcs across two electrodes to complete the circuit. An electrical impedance measurement device 4350 measures the resistance in ohms across the electrical impedance measurement device circuits 4352. A temperature measurement device for measuring the temperature of the test sample. A saline detector for measuring the salt concentration of the test sample. An electrical field and ionic strength measuring device for measuring the electrical field and ionic strength of the test sample. The electrical field, ionic strength, temperature, and salt concentration of the bodily fluid test sample affect the speed of sensing performance. These factors are measured and recorded on a memory device in the detection cartridge 1110. A digital processor installed in the portable detection cartridge reader 1100 reads these factors received from detection cartridge 1110 after inserting the detection cartridge 1110 into the portable detection cartridge reader 1100. The portable detection cartridge reader 1100 digital processor calculates the anticipated optimal sensing performance time and adjusts the time of the operation of the electrical power and current level to complete the impedance measurement processing. The description continues in FIG. 43B of one embodiment.

Figure 43B:
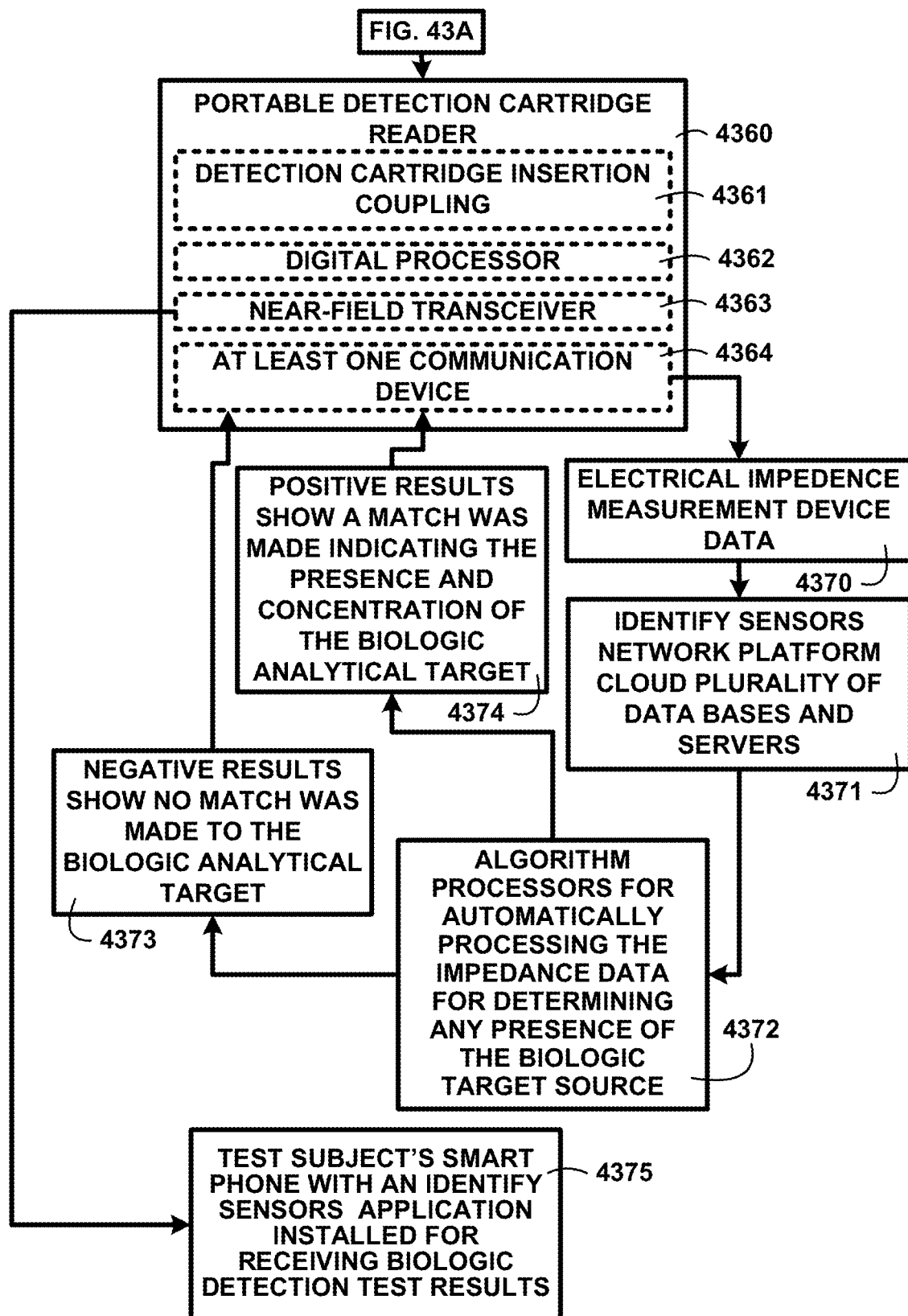
FIG. 43B shows a block diagram of an overview of a portable detection cartridge reader of one embodiment.

A Portable Detection Cartridge Reader:

FIG. 43B shows a block diagram of an overview of a portable detection cartridge reader of one embodiment. FIG. 43B shows a continuation from FIG. 43A with a portable detection cartridge reader 4360. The portable detection cartridge reader 4360 comprises a detection cartridge insertion connection port coupling 4361 with circuits for transferring data from the disposable detection cartridge to detect selectable biologic analytical targets 4300 of FIG. 43A. The portable detection cartridge reader 4360 further comprises a digital processor 4362 for formatting the disposable detection cartridge transferred data automatically.

Formatting the disposable detection cartridge transferred data includes adding the portable detection cartridge reader 4360 unique identifying number, the disposable detection cartridge identifying number showing the biologic analytical target identification code, the testing GPS location, date and time, base impedance measured without the test sample, and the impedance data with the test sample in contact with the sensor.

The portable detection cartridge reader 4360 further comprises a near-field transceiver 4363 for communicating with a test subject digital device automatically. At least one communication device 4364 is provided for transmitting electrical impedance measurement device data 4370 automatically. After formatting the data is transmitted to identify sensors network platform cloud plurality of databases and servers 4371 automatically. The data is stored on a plurality of databases automatically. The stored data is automatically transmitted to algorithm processors for automatically processing the impedance data for determining any presence of the biologic target source 4372. Negative results show no match was made to the biologic analytical target 4373. Positive results show a match was made indicating the presence and concentration of the biologic analytical target 4374.

The test results are transmitted to the portable detection cartridge reader 4360 and displayed automatically within minutes. The near-field transceiver 4363 automatically determines if the test subject digital device is in close proximity to receive the test results, if so then the results are transmitted to the test subject digital device. Should the test subject digital device be out of range for a near-field transmission then at least one communication device 4364 automatically transmits a cellular signal to the test subject digital device for displaying the test results on the test subject digital device. The test subject digital device may for example be a test subject's smartphone with an identify sensors application installed for receiving biologic detection test results 4375 of one embodiment.

Figure 43C:
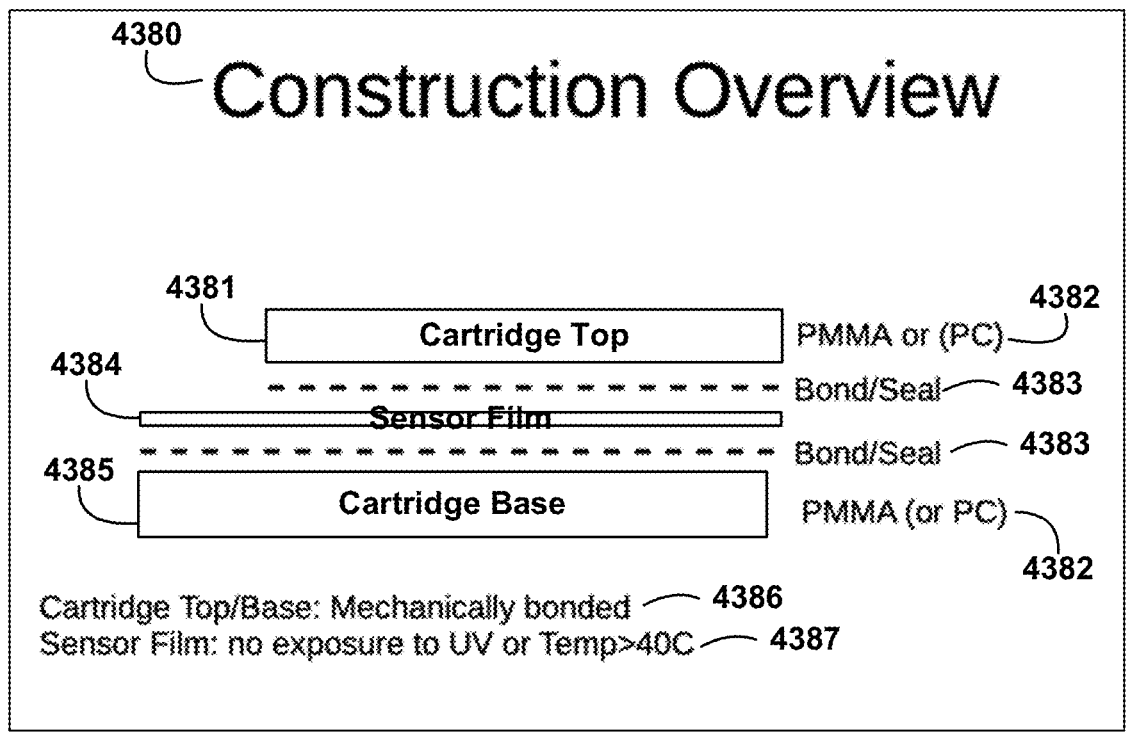
FIG. 43C shows for illustrative purposes only an example of a construction overview of one embodiment.

A Portable Detection Cartridge:

FIG. 43C shows for illustrative purposes only an example of a construction overview of one embodiment. FIG. 43C shows the sensor build-up for two different sensors. The "conductivity sensor" is one type of sensor and the "impedimetric antigen sensor" is another. The construction overview 4380 shows a cartridge top 4381 made of PMMA or (PC) 4382. A mechanical bond/seal 4383 couples the cartridge top 4381 to the sensor film 4384. A mechanical bond/seal 4383 couples the sensor film 4384 to a cartridge base 4385 made of PMMA or (PC) 4382. A cartridge top/base: mechanically bonded 4386 enclosing the sensor film: no exposure to UV or Temp>40C 4387 of one embodiment.

Figure 43D:
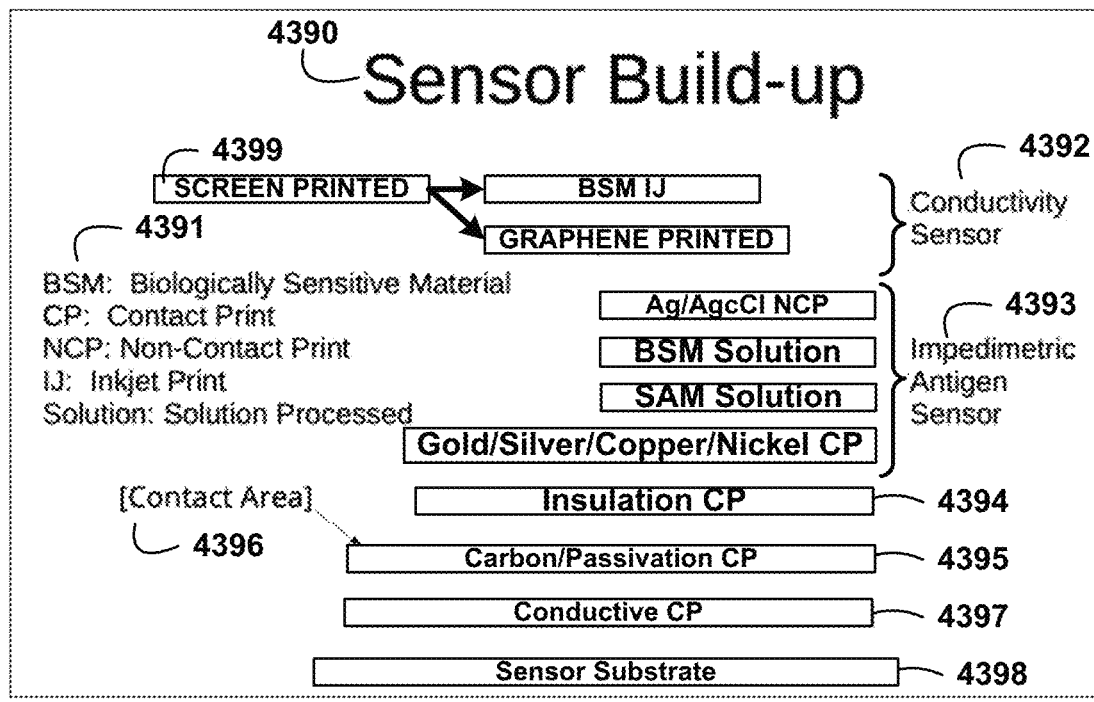
FIG. 43D shows for illustrative purposes only an example of a sensor build-up of one embodiment.

Sensor Build-Up:

FIG. 43D shows for illustrative purposes only an example of a sensor build-up of one embodiment. FIG. 43D shows a sensor build-up for two different types of sensors. The first is the "Conductivity Sensors" the second sensor is the "Antigen Sensor". The antigen sensor will be used for applications involving breath or in HVAC systems. FIG. 43D shows a sensor build-up 4390 for the two different types of sensors. The following are definitions 4391 used in this figure and include BSM: Biologically Sensitive Material; CP: Contact Print; NCP: Non-Contact Print; IJ: Inkjet Print; and Solution: Solution-Processed. A Conductivity Sensor 4392 includes a BSM IJ and graphene IJ. It should be appreciated that the BSM and graphene layers can also be screen printed 4399. An Impedimetric Antigen Sensor 4393 includes an Ag/AgCl NCP, BSM Solution, SAM Solution, and Gold/Silver/Copper/Nickel CP. The two different types of sensors include an Insulation CP 4394, Carbon/Passivation CP 4395 Contact Area 4396, Conductive CP 4397, and Sensor Substrate 4398 of one embodiment.

Figure 44:
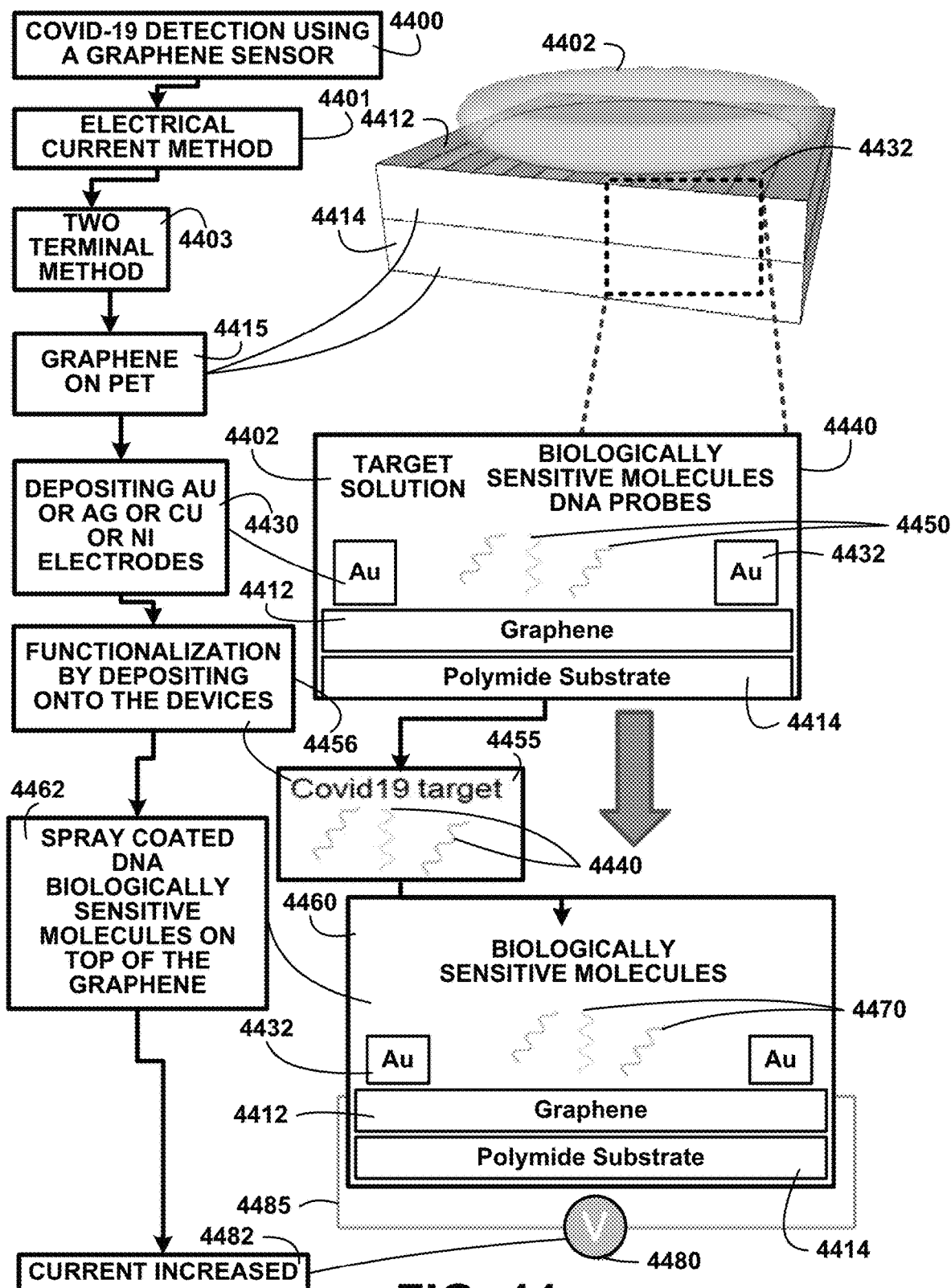
FIG. 44 shows for illustrative purposes only an example of an electrical current method of one embodiment.

An Electrical Current Method:

FIG. 44 shows for illustrative purposes only an example of an electrical current method of one embodiment. FIG. 44 shows a COVID-19 detection using a graphene sensor 4400 for an electrical current method 4401 of detecting selectable biologic analytical targets. A target solution 4402 of DNA probes 4550 is deposited on a plurality of an AU/AG/CU/NI electrode 4432 precision printed on a graphene 4412 material bonded to a polyimide substrate 4414. The electrical current method 4401 uses a two-terminal method 4403.

The sensor structure can be of embodiments including a graphene on PET 4415 or print graphene ink on a polyimide substrate and upon the graphene 4412 depositing AU/AG/CU/NI electrodes 4430. The chemical symbols used herein are AU for gold, AG for silver, CU for copper and NI for nickel. On the surface of the graphene 4412 bonded to the polyimide substrate 4414 and between each AU/AG/CU/NI electrode 4432, DNA biologically sensitive molecules probes 4440 are polarized and bonded to the graphene 4412.

In this example, the DNA biologically sensitive molecules probes 4440 are COVID-19 target 4455 DNA biologically sensitive molecules probes for detecting the selectable biologic analytical target COVID-19 also referred to herein as SARS-CoV-2. Graphene sensors are processed for functionalization by depositing onto the devices 4456 in a DNA biologically sensitive molecules probes 4440 solution. IDE electrodes can be functionalized by drop cast, dip coat, spray coat, and other means. The DNA biologically sensitive molecules probes 4440 solution may include spray-coated DNA biologically sensitive molecules on top of the graphene 4462 for DNA biologically sensitive molecules 4460. COVID-19 target RNA biologically sensitive molecules 4470 may be present in a test subject's bodily fluid sample target solution 4402.

A power supply 4480 energizes each AU/AG/CU/NI electrode 4432 through power supply circuits 4485. The power supply 4480 current increased 4482 sufficiently to complete a circuit between the pairs of the AU/AG/CU/NI electrode 4432 in the two-terminal methods 4403. Each selectable biologic analytical target produces different impedance results when power is applied. Proprietary experimentation has determined these unique impedance characteristics. No amplification or changes to the raw material (DNA biologically sensitive molecules probes and target RNA biologically sensitive molecules) are made to obtain a pure unadulterated impedance measurement of one embodiment.

Figure 45A:
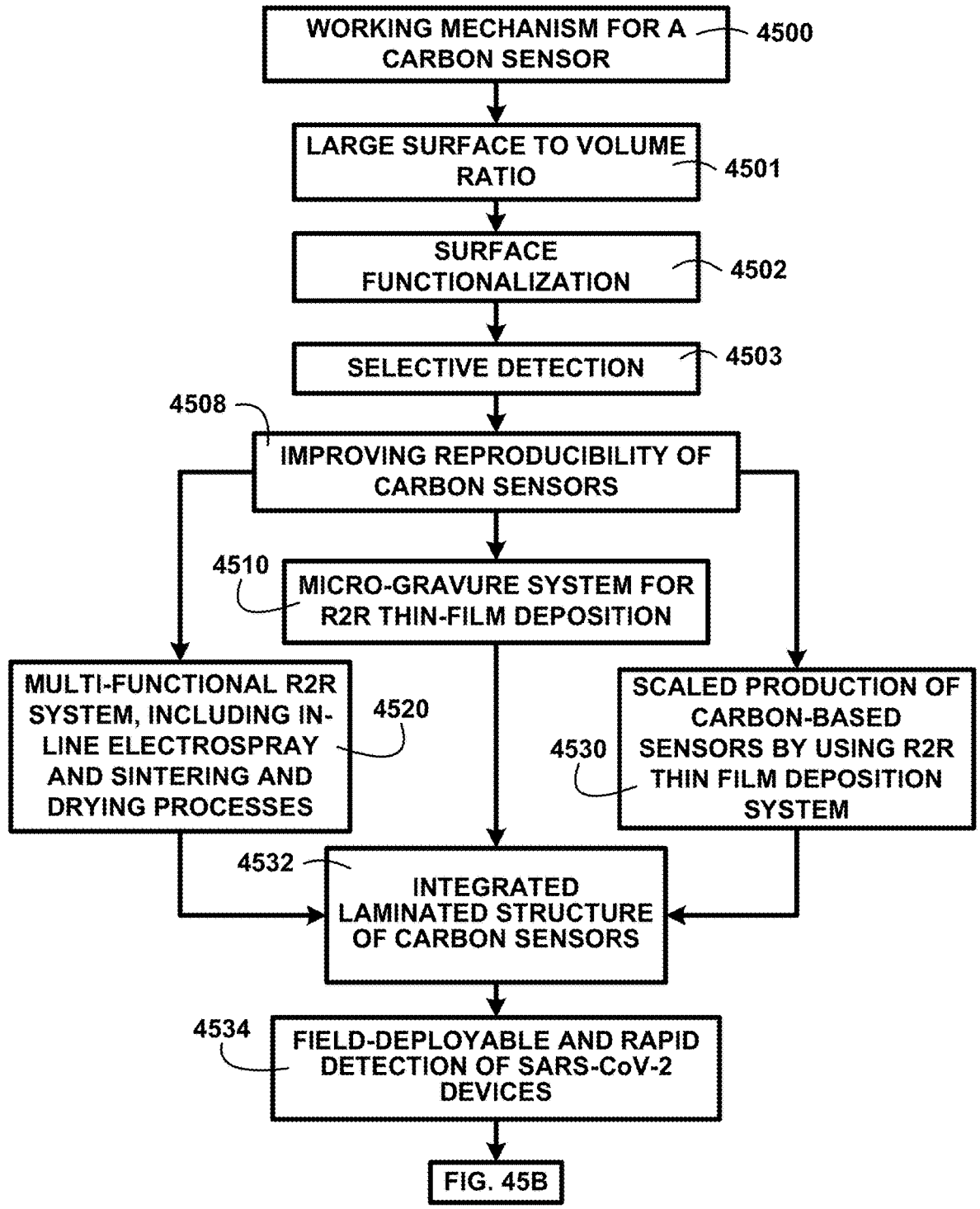
FIG. 45A shows a block diagram of an overview of a working mechanism for carbon sensors of one embodiment.

Working Mechanism for Carbon Sensors:

FIG. 45A shows a block diagram of an overview of the working mechanism for carbon sensors of one embodiment. FIG. 45A shows a working mechanism for carbon sensors 4500. The sensor may provide a carbon element of one from a group of other allotropes of carbon, graphene, and carbon materials with similar characteristics. The carbon element has a large surface to volume ratio 4501. The surface functionalization 4502 with DNA biologically sensitive molecules of a selectable biologic analytical target allows selective detection 4503 of biological organisms for example SARS-CoV-2 virus, influenza virus, swine flu, MSRA, Legionnaires, and many others. Improving reproducibility of carbon sensors 4508 includes a micro-gravure system for R2R thin-film deposition 4510 and R2R NIR drying and curing processes.

The term R2R herein refers to roll-to-roll processing or R2R. Roll-to-roll processing may include a multi-functional R2R system, including in-line electrospray 4520. Production costs are reduced using scaled production of carbon-based sensors by using R2R thin film deposition system 4530. The end product of the R2R process creates an integrated laminated structure of carbon sensors 4532. The detection cartridge 1310 of FIG. 13 provides a selectable biologic target detection system that is field-deployable and in one embodiment rapid detection of SARS-CoV-2 devices 4534 in one embodiment. The description continues in FIG. 45B.

Figure 45B:
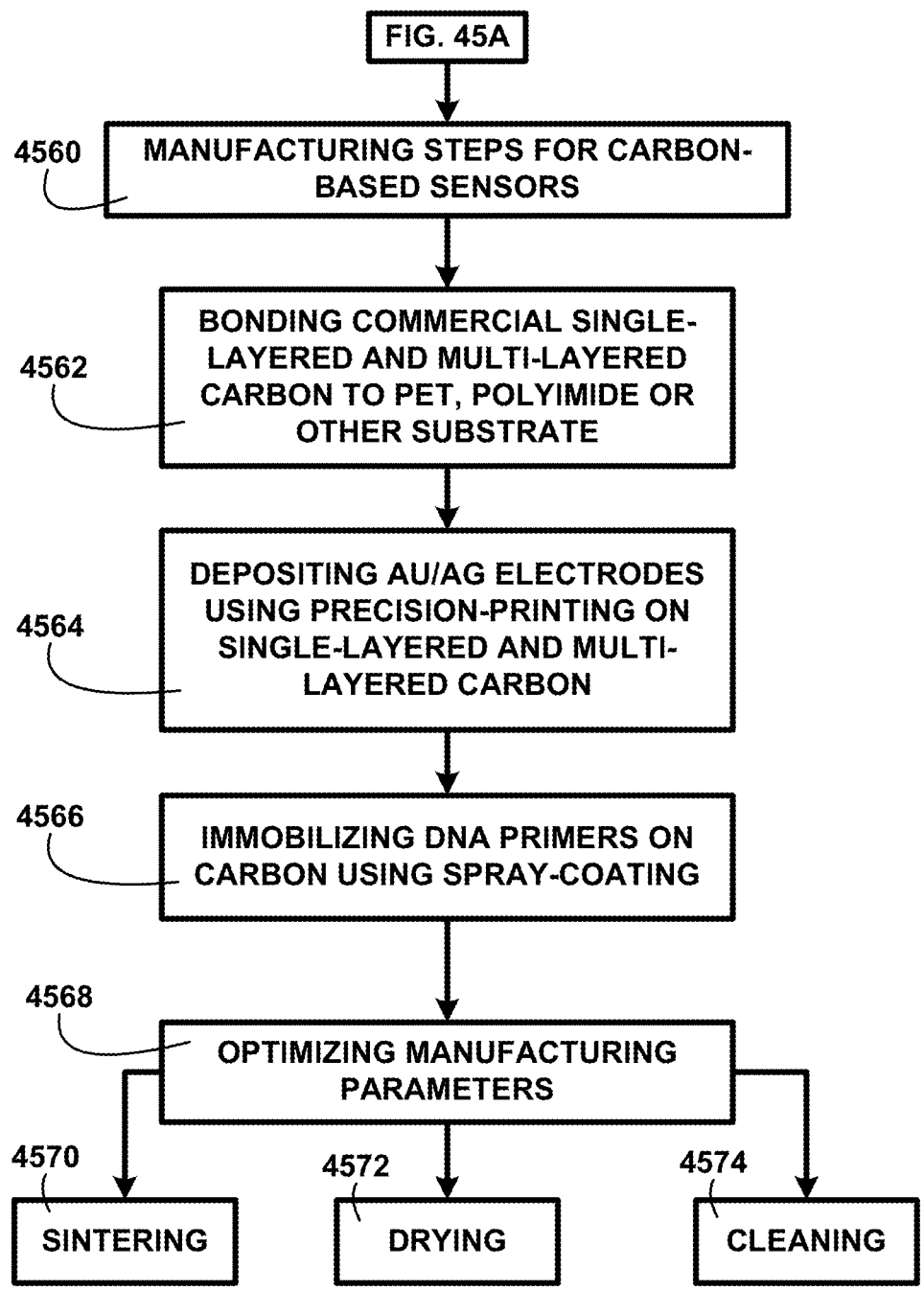
FIG. 45B shows a block diagram of an overview flow chart of manufacturing steps for carbon-based sensors of one embodiment.

Manufacturing Steps for Carbon-Based Sensors:

FIG. 45B shows a block diagram of an overview flow chart of manufacturing steps for carbon-based sensors of one embodiment. FIG. 45B shows a continuation from FIG. 45A and showing manufacturing steps for carbon-based sensors 4560 including bonding commercial single-layered and multi-layered carbon to PET, Polyimide or other substrate 4562. Another step is depositing AU/AG electrodes using precision-printing on single-layered and multi-layered carbon 4564. A subsequent step is immobilizing biologically sensitive molecules on carbon using spray-coating 4566. The manufacturing steps for the production of carbon-based sensors 4560 provide optimizing manufacturing parameters 4568 for sintering 4570, drying 4572, and cleaning 4574 of one embodiment.

Figure 46:
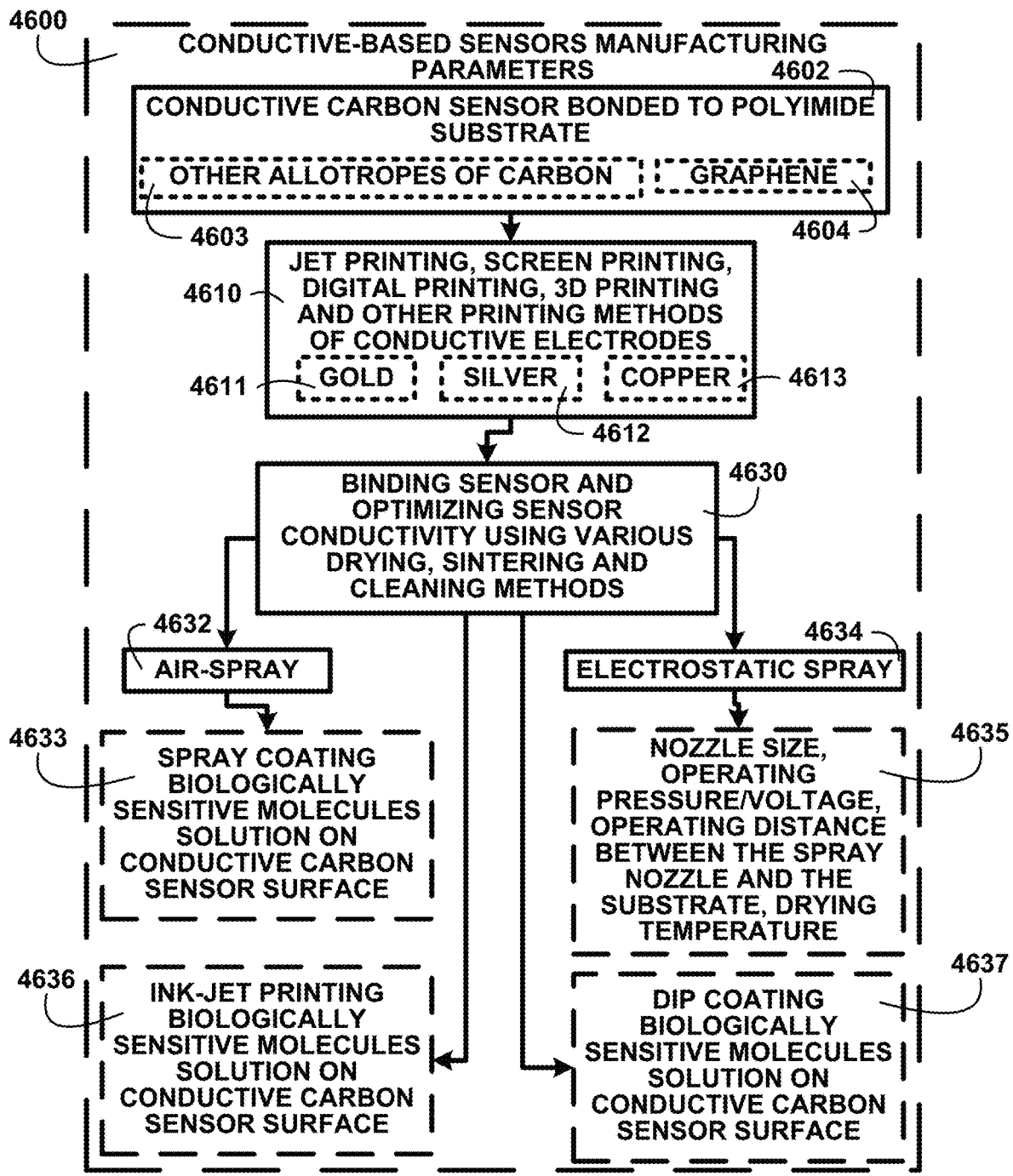
FIG. 46 shows a block diagram of an overview of conductive-based sensors manufacturing parameters of one embodiment.

Conductive-Based Sensors Manufacturing Parameters:

FIG. 46 shows a block diagram of an overview of conductive-based sensors manufacturing parameters of one embodiment. FIG. 46 shows conductive-based sensors manufacturing parameters 4600. One manufacturing parameter includes a conductive carbon sensor bonded to polyimide substrate 4602. The conductive carbon materials include one from a group of other allotropes of carbon 4603, graphene 4604, and other carbon materials with similar characteristics.

Another manufacturing parameter includes jet printing, screen printing, inkjet printing, digital printing, 3D printing, and additive manufacturing of conductive electrodes 4610. The conductive electrode materials include gold 4611, or silver 4612, or copper 4613 or nickel. Another manufacturing parameter includes depositing using ink-jet print or screen print at least one layer of graphene or other carbon ink. This step may require multiple layers, at different densities or ink volume, and a different speed, power, and duration setting.

Another manufacturing parameter includes drying/curing using various methods of drying including but not limited to NIR, laser, microwave, pulse forge, filter, paddle, spherical, and can be used at different speed and power settings. Another manufacturing parameter includes cleaning/treatment using various methods of cleaning or plasma treatment to remove interfering ions.

Another manufacturing parameter includes a binding sensor and optimizing sensor conductivity using various drying, curing, sintering and cleaning methods 4630. In one embodiment, drying target biologic material includes an air-spray 4632. The air-spray 4632 produces a spray coating biologically sensitive molecules solution on conductive carbon sensor surface 4633. The drying parameter includes various methods of drying including but not limited to (NIR, laser, microwave, pulse, etc. . . . ) can be used at a different speed, power, cycle, and distance setting. In another embodiment, drying target biologic material includes an electrostatic spray 4634.

The electrostatic spray 4634 is controlled according to nozzle size, operating pressure/voltage, operating distance between the spray nozzle and the substrate, drying temperature 4635. In another embodiment, deposition includes ink-jet printing biologically sensitive molecules solution on conductive carbon sensor surface 4636. In another embodiment, deposition includes dip-coating biologically sensitive molecules solution on conductive carbon sensor surface 4637.

Electrochemical Detection of SARS-CoV-2 Biologic Analytical Target:

FIG. 47A shows for illustrative purposes only an example of electrochemical detection of SARS-CoV-2 biologic analytical target of one embodiment. FIG. 47A shows a detection sensor for electrochemical detection of SARS-CoV-2 biologic analytical target 4700. The detection sensor for electrochemical detection of SARS-CoV-2 biologic analytical target 4700 comprises a bodily fluid deposition port 4710 for depositing bodily fluid drops 4711 onto the detection sensor. The detection sensor base is a polyimide dielectric flexible film substrate 4720. On the substrate, a carbon sensor is bonded to the polyimide substrate 4702. A plurality of target biologic biologically sensitive molecules specific for SARS-CoV-2, are bound to the carbon sensor and stabilized inductively 4724. Printed electrodes 4725 are positioned on the surface of the carbon sensor.

Biologic analytical target RNA biologically sensitive molecules 4740 in the bodily fluid showing in these examples SARS-CoV-2 RNA biologically sensitive molecules, if present in the bodily fluid creates a unique impedance to the electrical circuit flowing through the printed electrodes 4725. A measured power level is delivered through for example a first IDE 4730. The electrical power flows through the first IDE 4730 electrodes from printed IDEs 4722. The electrical power from a first IDE circuit 4732 is conducted by the plurality of target biologic DNA molecules specific for SARS-CoV-2 and SARS-CoV-2 RNA biologically sensitive molecules to the second IDE 4731 electrodes completing the circuit to a second IDE circuit 4734.

The plurality of target biologic DNA biologically sensitive molecules specific for SARS-CoV-2 and SARS-CoV-2 RNA biologically sensitive molecules create a resistance to the flow of the electricity (impedance). The resulting reduction in the flow of electricity (impedance) is measured. In this example, the impedance of the plurality of target biologic DNA biologically sensitive molecules specific for SARS-CoV-2 and SARS-CoV-2 RNA biologically sensitive molecules is known through proprietary experimentation. A positive test result shows the impedance measurement decreases and current measurement increases. Should the measured impedance match the experimentally determined known SARS-CoV-2 impedance, it indicates the presence of the SARS-CoV-2 virus. If the measured impedance does not match the experimentally determined known SARS-CoV-2 impedance, it indicates the SARS-CoV-2 virus is not present in the bodily fluid sample of one embodiment.

Breathe Moisture Test Sampling:

FIG. 47B shows for illustrative purposes only an example of breath moisture test sampling of one embodiment. FIG. 47B shows a test subject blowing moist breath 4750 into the bodily fluid deposition port 4710 of the detection cartridge 1310. A test subject breath moisture bodily fluid test sample 4314 deposits biologic analytical target RNA biologically sensitive molecules 4740, if present. If present, the detection sensor for electrochemical detection of SARS-CoV-2 biologic analytical target 4700 test results will be positive of one embodiment.

No Test Sample Impedance Measurement:

FIG. 48A shows for illustrative purposes only an example of a no test sample impedance measurement of one embodiment. FIG. 48A shows the detection sensor for electrochemical detection of SARS-CoV-2 biologic analytical target 4700. The detection sensor includes the polyimide substrate 4702, in one embodiment graphene 4412, target biologically sensitive molecules deposited onto the graphene 4800, and at least two AU/AG/CU/NI electrodes 4432. In one embodiment, the biologically sensitive molecules are drop cast onto the sensor surface. Other embodiments include spray coating and dip coating the biologically sensitive molecules onto the sensor surface. Drop casting is a thin film deposition onto a flat surface followed by evaporation of the solution. A thin film is a layer of material ranging from a few tenths of a nanometer to several micrometers in thickness.

At least two AU/AG/CU/NI electrodes 4432 carry an electrical current 4804 flow between two pole AU/AG/CU/NI electrodes. An electrode measurement circuit 4810 passes the electrical current 4804 in this example through a meter to measure the circuit electrical current 4804. The meter reading with no bodily fluid sample present 4812 shows the base current. The meter reading data is transmitted to a cloud 4814 for recording and analysis. A graph of detection cartridge data 4816 is shown with the flat line base current and determined by an algorithmic analysis of detection cartridge data no test sample present 4818 of one embodiment.

Test Sample with Low Biologic Target Concentration Impedance Measurement:

FIG. 48B shows for illustrative purposes only an example of a test sample with low biologic target concentration impedance measurement of one embodiment. FIG. 48B shows the detection sensor for electrochemical detection of SARS-CoV-2 biologic analytical target 4700. The detection sensor includes the polyimide substrate 4702, graphene 4412; target biologically sensitive molecules layered onto the graphene 4800, and at least two AU/AG/CU/NI electrodes 4432.

The bodily fluid sample in this example deposits target biologically sensitive molecules 4824 onto the target biologic molecules layered onto the graphene 4800 of FIG. 48A. The weak bond of the target biologically sensitive molecules layered onto the graphene 4800 is broken and lifts the target biological molecules due to the stronger bond with the biologically sensitive molecules 4820. The detection sensor automatically initiates an electrical current 4804 in the electrode measurement circuit 4810. The meter reading within a low concentration of target biologic biologically sensitive molecules 4826 measures the current through the biologically sensitive molecules.

The current data is automatically transmitted to the cloud 4814. The graph of detection cartridge data 4816 displays the algorithmic analysis of detection cartridge data of low concentration of target biologically sensitive molecules 4829 showing a spike in the current. The current measurement identifies the biologically sensitive molecules as the SARS-CoV-2 biologic analytical target and the magnitude of the impedance measurement indicates the low concentration of the numbers of COVID-19 biologically sensitive molecules. These test findings produce a positive result that the test subject is infected with COVID-19 of one embodiment.

Test Sample with High Biologic Target Concentration Impedance Measurement:

FIG. 48C shows for illustrative purposes only an example of a test sample with high biologic target concentration impedance measurement of one embodiment. FIG. 48C shows the detection sensor for electrochemical detection of SARS-CoV-2 biologic analytical target 4700. The detection sensor includes the polyimide substrate 4702, graphene 4412; target biologic molecules layered onto the graphene 4800, and at least two AU/AG/CU/NI electrodes 4432.

The bodily fluid sample in this example deposits target biologically sensitive molecules 4824 onto the target biologic molecules layered onto the graphene 4800 of FIG. 48A. The weak bond of the target biologic DNA molecules layered on to the graphene 4800 is broken and lifts the target biologic DNA molecules due to the stronger bond of the biologically sensitive molecules 4820. The detection sensor automatically initiates an electrical current 4804 in the electrode measurement circuit 4810.

The meter reading of the higher concentration of target biologically sensitive molecules 4840 measures the current through the biologically sensitive molecules. The current data is automatically transmitted to the cloud 4814. The graph of detection cartridge data 4816 displays the algorithmic analysis of detection cartridge data of low concentration of target biologically sensitive molecules 4836 showing a spike in the current. The current measurement identifies the biologically sensitive molecules as the SARS-CoV-2 biologic analytical target and the magnitude of the current measurement indicates the higher concentration of the numbers of COVID-19 biologically sensitive molecules. These test findings produce a positive result that the test subject is infected with COVID-19 of one embodiment.

Figure 49A:
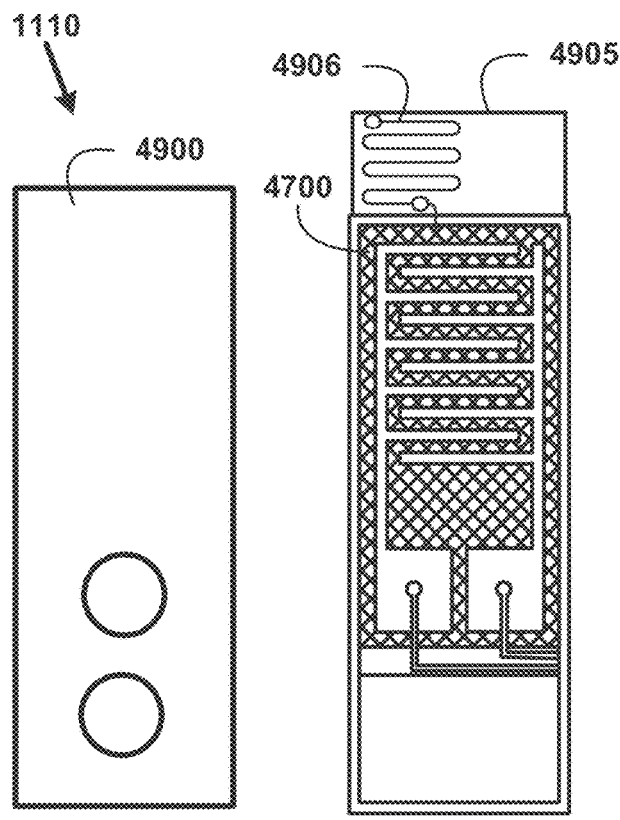
FIG. 49A shows for illustrative purposes only an example of opened test cartridge showing a sensor of one embodiment.

Opened Test Cartridge Showing Sensor:

FIG. 49A shows for illustrative purposes only an example of opened test cartridge showing a sensor of one embodiment. FIG. 49A shows the detection cartridge 1110 opened with a detection cartridge top cover 4900 to one side and an interior view of the detection cartridge bottom case 4905. The interior view shows the detection sensor for electrochemical detection of SARS-CoV-2 biologic analytical target 4700 installed in the detection cartridge bottom case 4905 of one embodiment. In one embodiment the detection cartridge bottom case 4905 includes a heater 4906 to test cartridge samples.

Figure 49B:
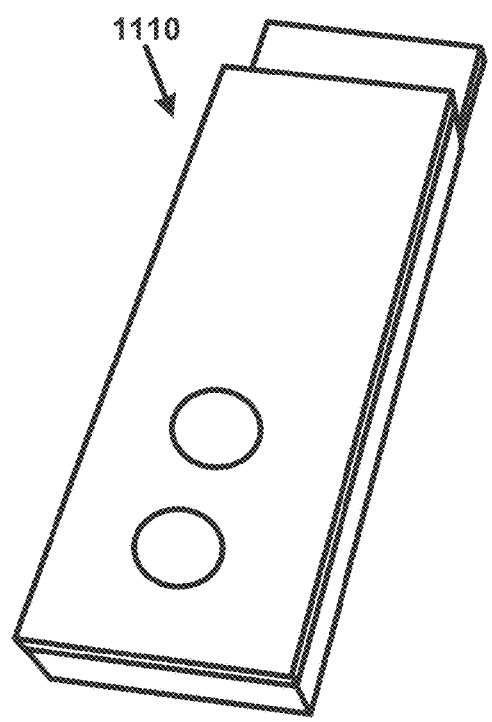
FIG. 49B shows for illustrative purposes only an example of a closed test cartridge of one embodiment.

Closed Test Cartridge:

FIG. 49B shows for illustrative purposes only an example of a closed test cartridge of one embodiment. FIG. 49B shows the detection cartridge 1110 closed with the detection sensor for electrochemical detection of SARS-CoV-2 biologic analytical target 4700 of FIG. 47A installed one embodiment.

Figure 49C:
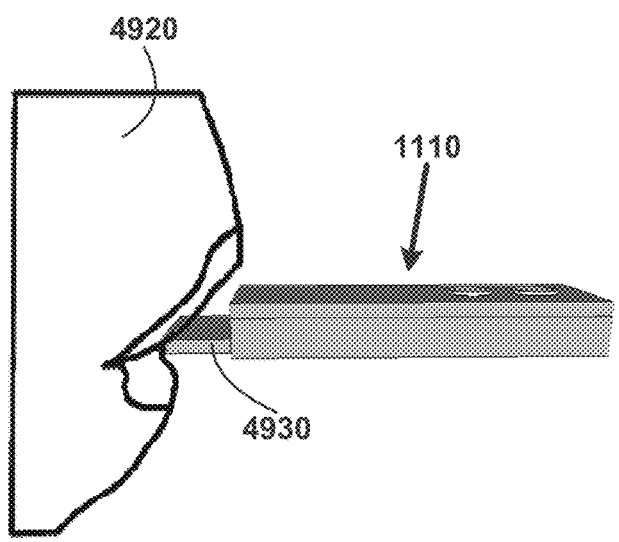
FIG. 49C shows for illustrative purposes only an example of a test subject depositing sample of one embodiment.

Test Subject Depositing Sample:

FIG. 49C shows for illustrative purposes only an example of test subject depositing sample of one embodiment. FIG. 49C shows the test subject blowing moist breath into the detection cartridge bodily fluid deposition port 4920. A bodily fluid deposition port 4930 includes a passageway for the moisture in the test subject's breath to deposit on the detection sensor for electrochemical detection of SARS-CoV-2 biologic analytical target 4700 of FIG. 47A within the detection cartridge 1110 of one embodiment.

Figure 49D:
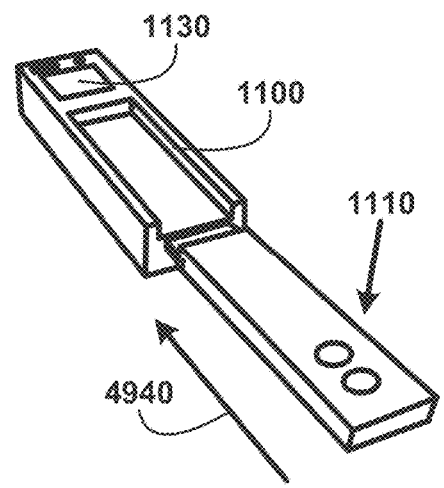
FIG. 49D shows for illustrative purposes only an example of a test cartridge inserting into a portable detection cartridge reader of one embodiment.

Test Cartridge Inserting into Portable Detection Cartridge Reader:

FIG. 49D shows for illustrative purposes only an example of a test cartridge inserting into a portable detection cartridge reader of one embodiment. FIG. 49D shows the detection cartridge 1110 after a test subject deposits bodily fluid into the detection cartridge 1110. Inserting the detection cartridge into the portable detection cartridge reader 4940 allows the portable detection cartridge reader 1100 to read the detection data from the detection cartridge 1110 automatically upon insertion including a unique device identification code and a biologic analytical target identification code number. The portable detection cartridge reader display 1130 will display progress milestones as the processing of the test proceeds of one embodiment.

Figure 50A:
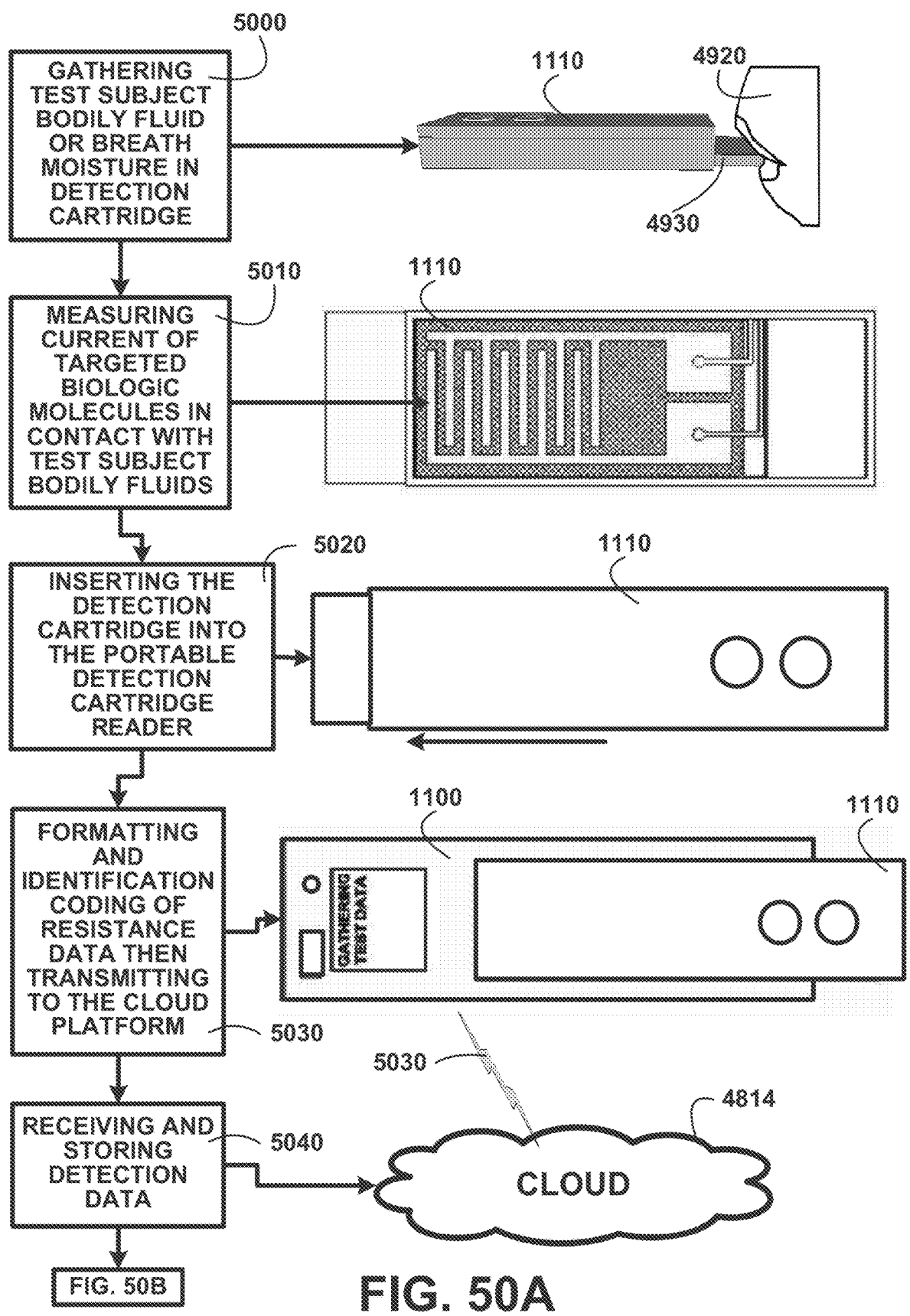
FIG. 50A shows for illustrative purposes only an example of an overview flow chart of gathering test subject samples of one embodiment.

Gathering Test Subject Sample:

FIG. 50A shows for illustrative purposes only an example of an overview flow chart of gathering test subject samples of one embodiment. FIG. 50A shows gathering test subject bodily fluid or breathe moisture in detection cartridge 5000. Gathering test subject test samples include for example a test subject blowing moist breath into the bodily fluid deposition port 4920. A bodily fluid deposition port 4930 provides a passageway for the test subject bodily fluids to be deposited on the detection cartridge 1110 detection sensor surface. The detection cartridge 1110 is for measuring the resistance of targeted biologic biologically sensitive molecules in contact with test subject bodily fluids 5010.

Inserting the detection cartridge into the portable detection cartridge reader 5020 begins the impedance measuring process. The impedance data is transmitted from the detection cartridge 1110 to the portable detection cartridge reader 1100 for formatting and identification coding of resistance data then transmitting to the cloud platform 5030 the formatted and identified data. The cloud 4814 is receiving and storing detection data 5040 for further processing as described in FIG. 50B of one embodiment.

Figure 50B:
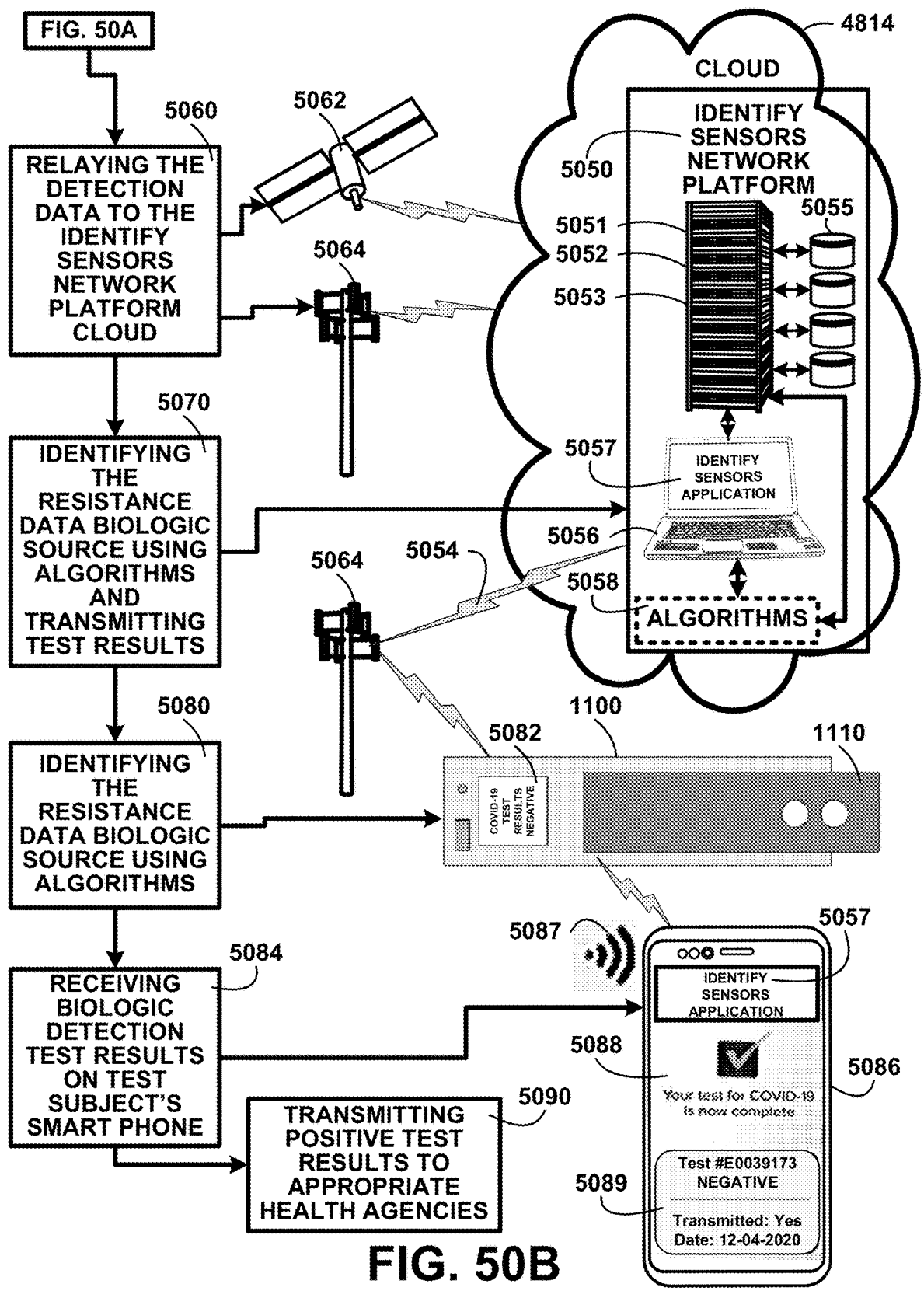
FIG. 50B shows for illustrative purposes only an example of an overview flow chart of identifying the resistance data biologic source of one embodiment.

Identifying the Resistance Data Biologic Source:

FIG. 50B shows for illustrative purposes only an example of an overview flow chart of identifying the resistance data biologic source of one embodiment. FIG. 50B shows a continuation from FIG. 50A including alternates of communication using satellite 5062 and cellular 5064 communications for relaying the detection data to the identify sensors network platform cloud 5060.

The detection data received in the cloud 4814 is processed using a identify sensors network platform 5050. The identify sensors network platform 5050 provides at least one server 5051, at least one digital processor 5052, at least one communication device 5053, a plurality of databases 5055, at least one network computer 5056, an identify sensors application 5057 and algorithms 5058 for analyzing the detection data. The algorithms 5058 analysis provides identifying the resistance data biologic source using algorithms and transmitting test results 5070.

Transmitting test results 5054 for example over cellular 5064 communications to the portable detection cartridge reader 1100 and alternatively to a test subject's smartphone 5086. In this example COVID-19 test results negative 5082 are determined after identifying the resistance data biologic source using algorithms 5080 does not show the presence of the SARS-CoV-2 biologically sensitive molecules in the test subject bodily fluids. The COVID-19 test results negative 5082 are transmitted to the portable detection cartridge reader 1100.

The test results are displayed on the portable detection cartridge reader 1100. The portable detection cartridge reader 1100 transmits the test results to a test subject's smartphone 5086. Receiving biologic detection test results on the test subject's smart phone 5084. The test results message in this example can be audible using Bluetooth® 5087 technology and also displayed on the test subject's smartphone 5086. The display of the test results may include as shown in this example "Your Test for COVID-19 is now complete" 5088 and "Test #E0039173 NEGATIVE Transmitted: Yes Date: Dec. 4, 2020" 5089. In instances where the test results are determined to be positive for COVID-19 transmitting positive test results to appropriate health agencies 5090 may be required of one embodiment.

Figure 51:
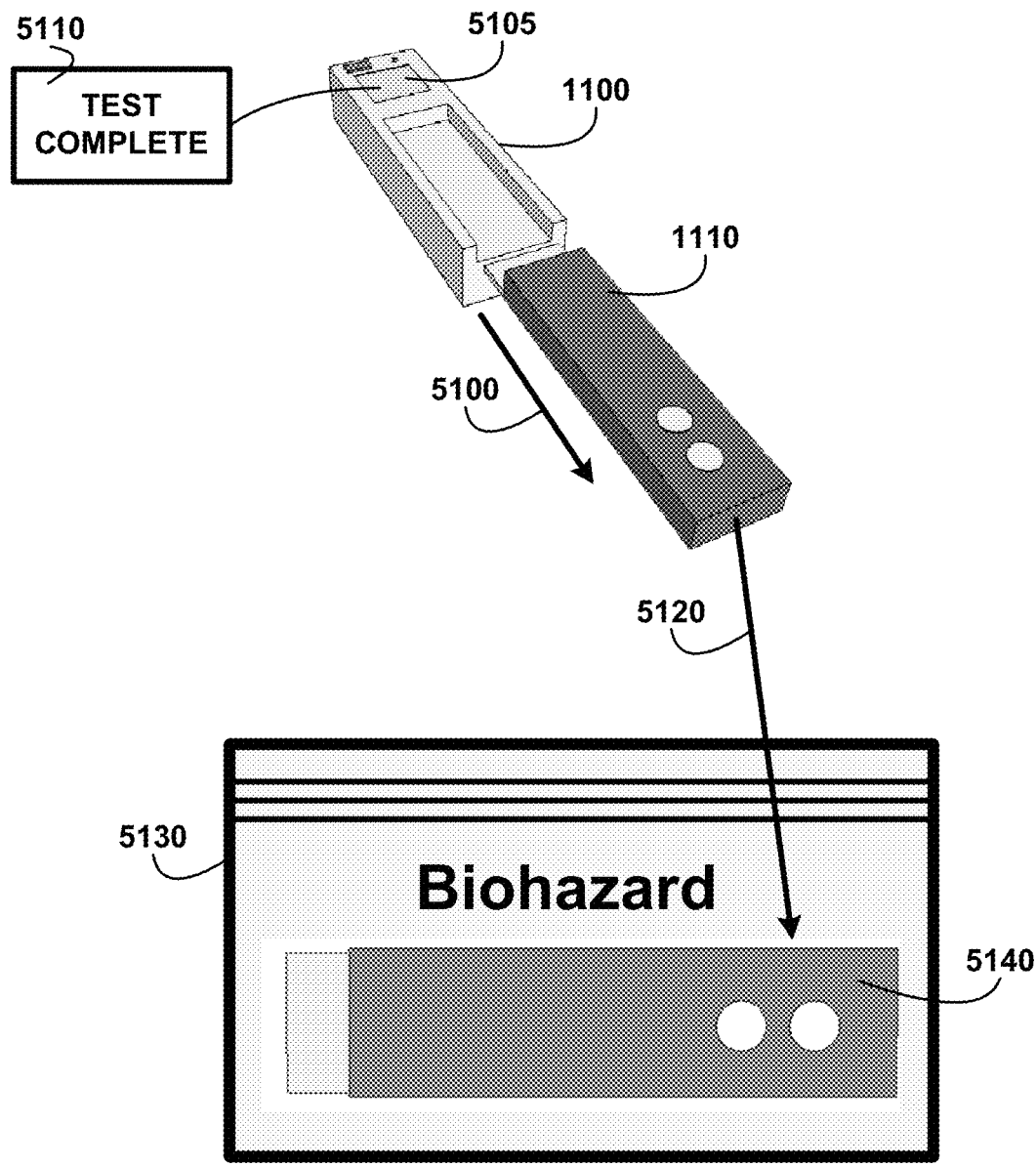
FIG. 51 shows for illustrative purposes only an example of disposal of used test cartridge of one embodiment.

Disposal of Used Test Cartridge:

FIG. 51 shows for illustrative purposes only an example of disposal of used test cartridge of one embodiment. FIG. 51 shows the portable detection cartridge reader 1100, detection cartridge 1110, display 5105 with the message test complete 5110. After test results are transmitted to the test subject, removing the disposable detection cartridge after completion of the test 5100 is performed for appropriate disposal of the detection cartridge 5120. In those instances where the target biologic is transmittable infectious biological materials that are showing as positive a sealable biohazard container 5130 may be required for appropriate disposal of the detection cartridge 5120. The detection cartridge in the biohazard container 5140 may be required to be taken to a facility designated for approved biohazard disposal of one embodiment.

Figure 52:
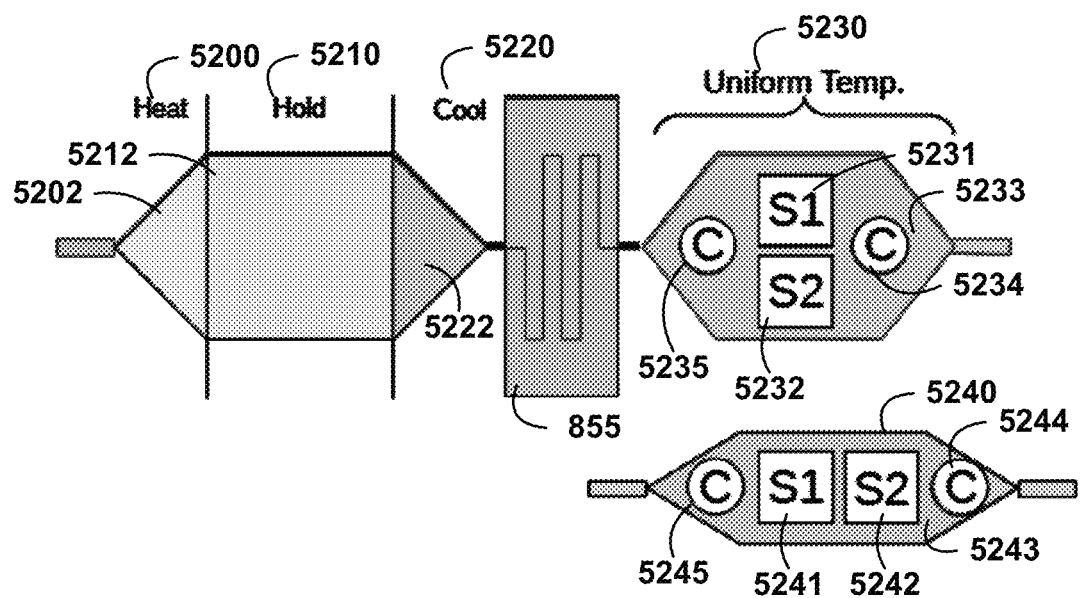
FIG. 52 shows for illustrative purposes only an example of a temperature control device of one embodiment.

Temperature Control Device:

FIG. 52 shows for illustrative purposes only an example of a temperature control device of one embodiment. FIG. 52 shows a temperature control device arrangement for testing samples. An initial area for applying heat 5200 in a heater section 5202 for a period time measured in seconds. A hold 5210 stage for the heated sample is held in the hold section 5212. An area to cool 5220 the sample in a cooling section 5222 for a period time measured in seconds. The temperature control device 855 applies heat or cooling to regulate the sample at a uniform temp. 5230, wherein temp.=temperature. A sensing section 5233 includes sensors S1 5231 and S2 5232, sensing section 5233, first C 5234, second C 5235. In this example FIG. 52A shows an alternative configuration for the sensing section 5240 with sensors S1 5241 and S2 5242 in the sensing section 5243 with the first C 5244 and second C 5245 of one embodiment.

Figure 53:
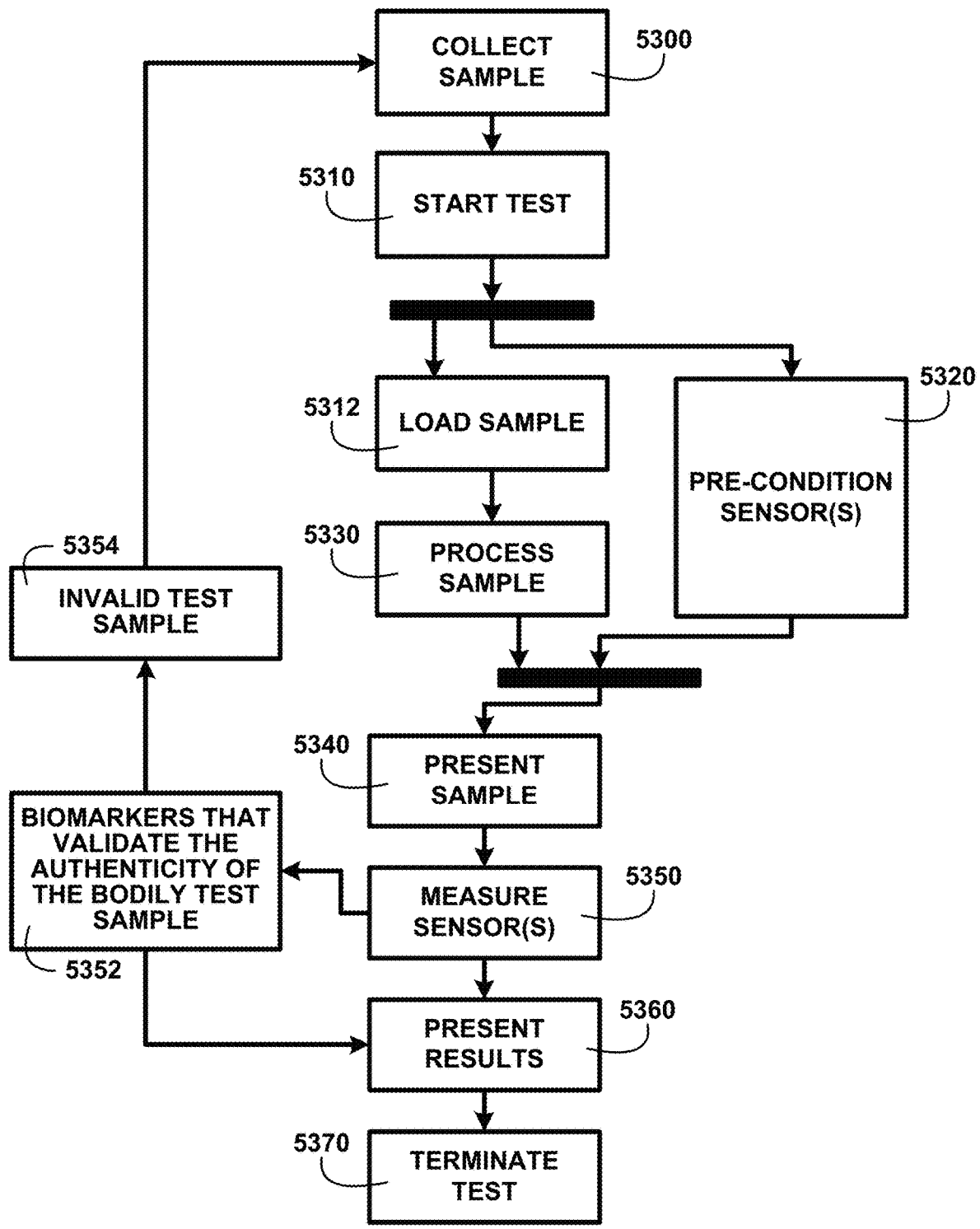
FIG. 53 shows a block diagram of an overview of a general test flow of one embodiment.

General Test Flow:

FIG. 53 shows a block diagram of an overview of a general test flow of one embodiment. FIG. 53 shows a general test flow for detection of infectious virus and bacterial pathogen and biomarkers indicative of viruses and pathogens. The test starts with collect sample 5300 and start test 5310. The test continues with load sample 5312 for processing and a portion of the sample for pre-condition sensor(s) 5320 to determine a base. The testing includes a process sample 5330 stage and then to present sample 5340 to measure sensor(s) 5350 for measuring factors in the sample. Among the factors measured in the sample include biomarkers that validate the authenticity of the bodily test sample 5352. For example the biomarker RNase P is used for CoVID-19 authentication of test samples. If the test sample is an invalid test sample 5354 the test is invalid and a new test sample is taken. The final step is to present results 5360 for evaluation and then terminate test 5370 of one embodiment.

Chemical and Pathogen Detection Air Sample and HVAC:

FIG. 54 shows a block diagram of an overview of chemical and pathogen detection in an air sample and HVAC system of one embodiment. FIG. 54 shows a process for chemical and pathogen detection in the air sample and HVAC 5400. The process begins with an air sample collected and electrically changed (usually negatively charged) 5410. A nebulizer containing a solution (buffer or other solutions) creates electrically charged (usually positively charged) aerosols 5420. The negatively charged air sample is attracted to the positively charged aerosols forming a uniform aerosolized test sample 5430.

The aerosolized test sample is transformed into a liquid test sample using an impactor nozzle to spray the aerosolized sample into an impaction plate, which causes the sample to transform into a liquid 5440. The liquid test sample is captured by a temperature-controlled fluidic path or chamber where the liquid sample can be electrically charged again if necessary 5450. The liquid test sample is presented to the sensor array for measurement through the temperature-controlled fluidic path or chamber 5460 of one embodiment. The test sample is disposed of in a waste reservoir using various active or passive induction devices such as vacuums or pumps 5470 of one embodiment.

Figure 55:
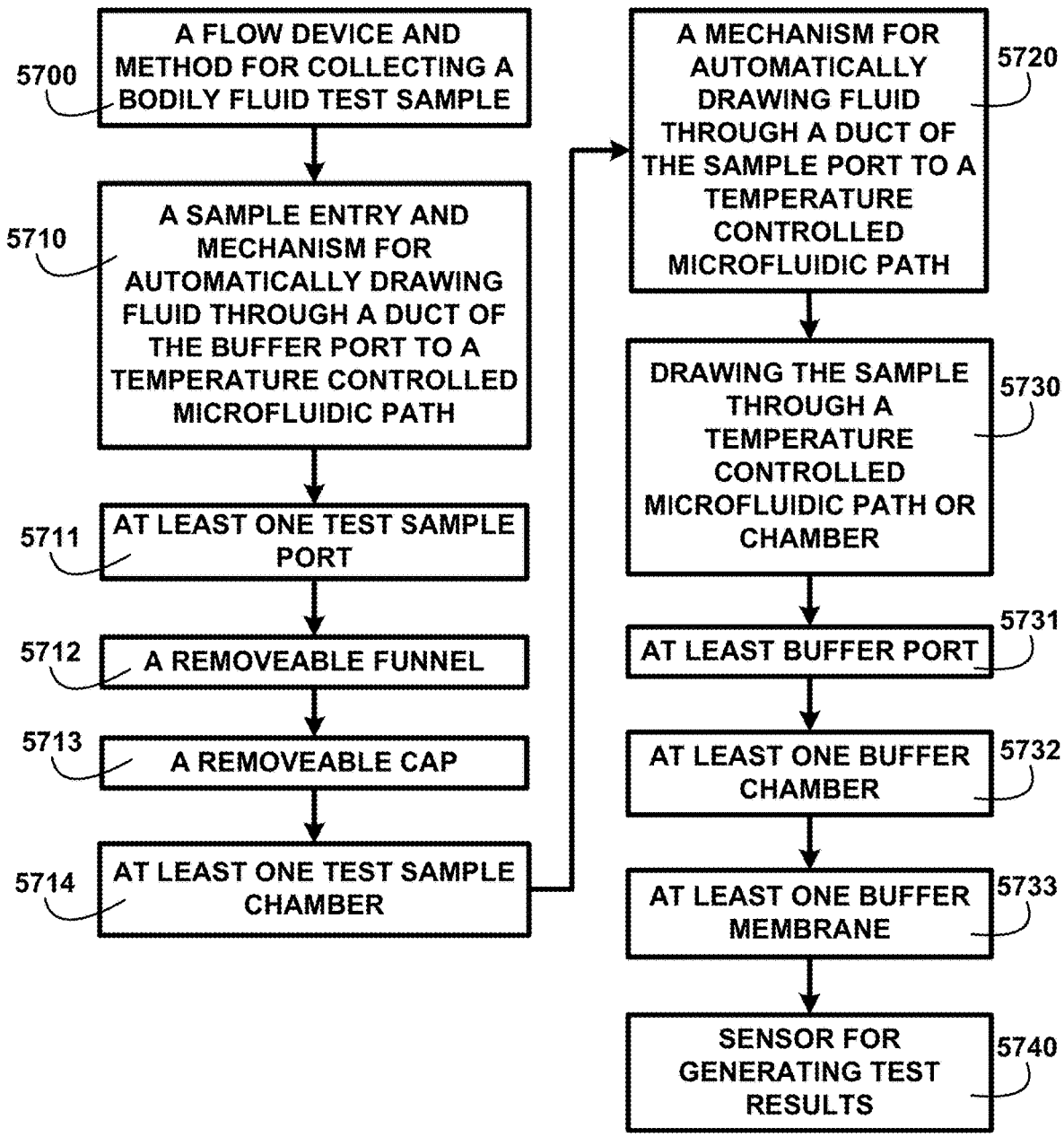
FIG. 55 shows a block diagram of an overview of a flow device of one embodiment.

Flow Device:

FIG. 55 shows a block diagram of an overview of a flow device of one embodiment. FIG. 55 shows a flow device and method for collecting a bodily fluid test sample 5700. The flow device includes a sample entry and mechanism for automatically drawing fluid through a duct of the buffer port to a temperature-controlled microfluidic path 5710. The flow device includes at least one test sample port 5711, a removable funnel 5712, a removable cap 5713, and at least one test sample chamber 5714. The flow device and method include a mechanism for automatically drawing fluid through a duct of the sample port to a temperature-controlled microfluidic path 5720. The mechanism is used for drawing the sample through a temperature-controlled microfluidic path or chamber 5730. The temperature-controlled microfluidic path or chamber includes at least buffer port 5731, at least one buffer chamber 5732, and at least one buffer membrane 5733. The flow device and method include a sensor for generating test results 5740 of one embodiment.

Figure 56:
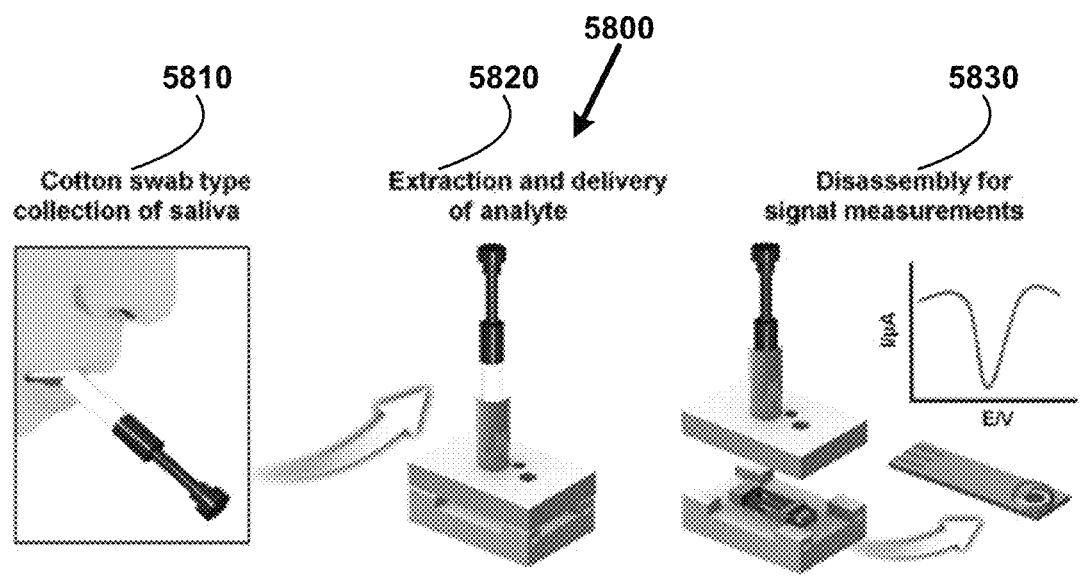
FIG. 56 shows for illustrative purposes only an example of a swabbing device for collecting and processing bodily test sample of one embodiment.

Swab Device for Collecting and Processing Bodily Test Sample:

FIG. 56 shows for illustrative purposes only an example of a swab device for collecting and processing bodily test sample of one embodiment. FIG. 56 shows a device and method for collecting a bodily fluid test sample and flowing the sample through a temperature-controlled microfluidic path or chamber to the sensor for generating test results 5800. The device includes a bodily fluid test sample collection swab for example for swab type collection of saliva 5810. The device includes a port for extracting test sample fluid from the swab. The extraction and delivery of analyte 5820 to test the sample fluid is processed. The device includes a printed component for flowing the bodily test sample through a temperature-controlled microfluidic path or chamber to the sensor for measurement and disposal of the bodily fluid test sample. A disassembly for signal measurements 5830 removes the sensor for electronic collection of the sensor signal measurements of one embodiment.

Figure 57:
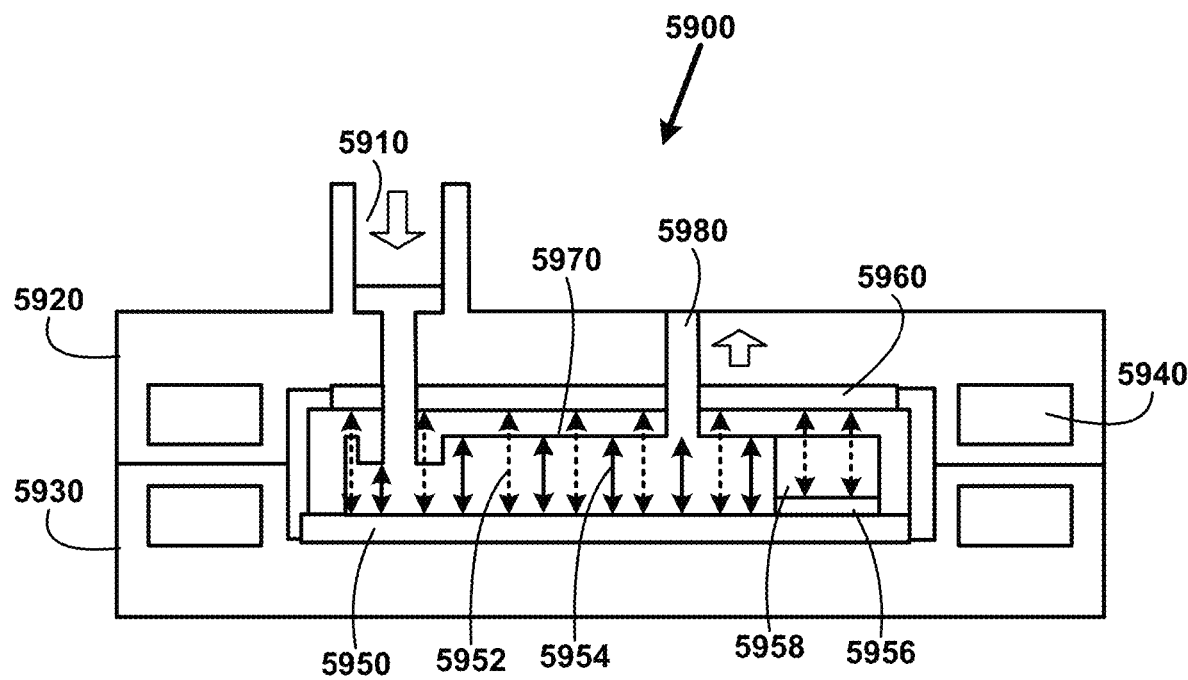
FIG. 57 shows for illustrative purposes only an example of a platform for processing and flowing the test samples of one embodiment.

Platform for Processing and Flowing the Test Sample to Sensor for Measurement:

FIG. 57 shows for illustrative purposes only an example of a platform for processing and flowing the test sample of one embodiment. FIG. 57 shows a platform for processing a bodily fluid test sample and flowing the sample through a temperature-controlled microfluidic path or chamber to the sensor for generating test results 5900. The exemplary platform includes a cover 5920, a holder 5930, an inlet 5910, an outlet 5980, PDMS 5970, jig 5960, a sensor 5950 including a working electrode 5956, and magnetic connectors 5940 that securely join the cover 5920 and holder 5930. The exemplary platform can also include a filter for removing interfering substances. Once the bodily fluid test sample in the swab is compressed by the extraction port, the bubble-depleted bodily fluid is injected into the temperature-controlled microfluidic path or chamber through the inlet. The sample then flows on top of the working electrode then onto the outlet and deposited in a waste reservoir.

The cover includes a jig on the bottom of the cover. The jig applies magnetic force 5952 to the outer wall of the PDMS channel 5954. The holder includes a grip on the top of the holder to hold the temperature-controlled fluidic chip and sensor in position. In the exemplary embodiment, the microfluidic path or chamber 5958 is separate from the sensor. In other embodiments, the microfluidic path or chamber is printed on the sensor film.

Figure 58:
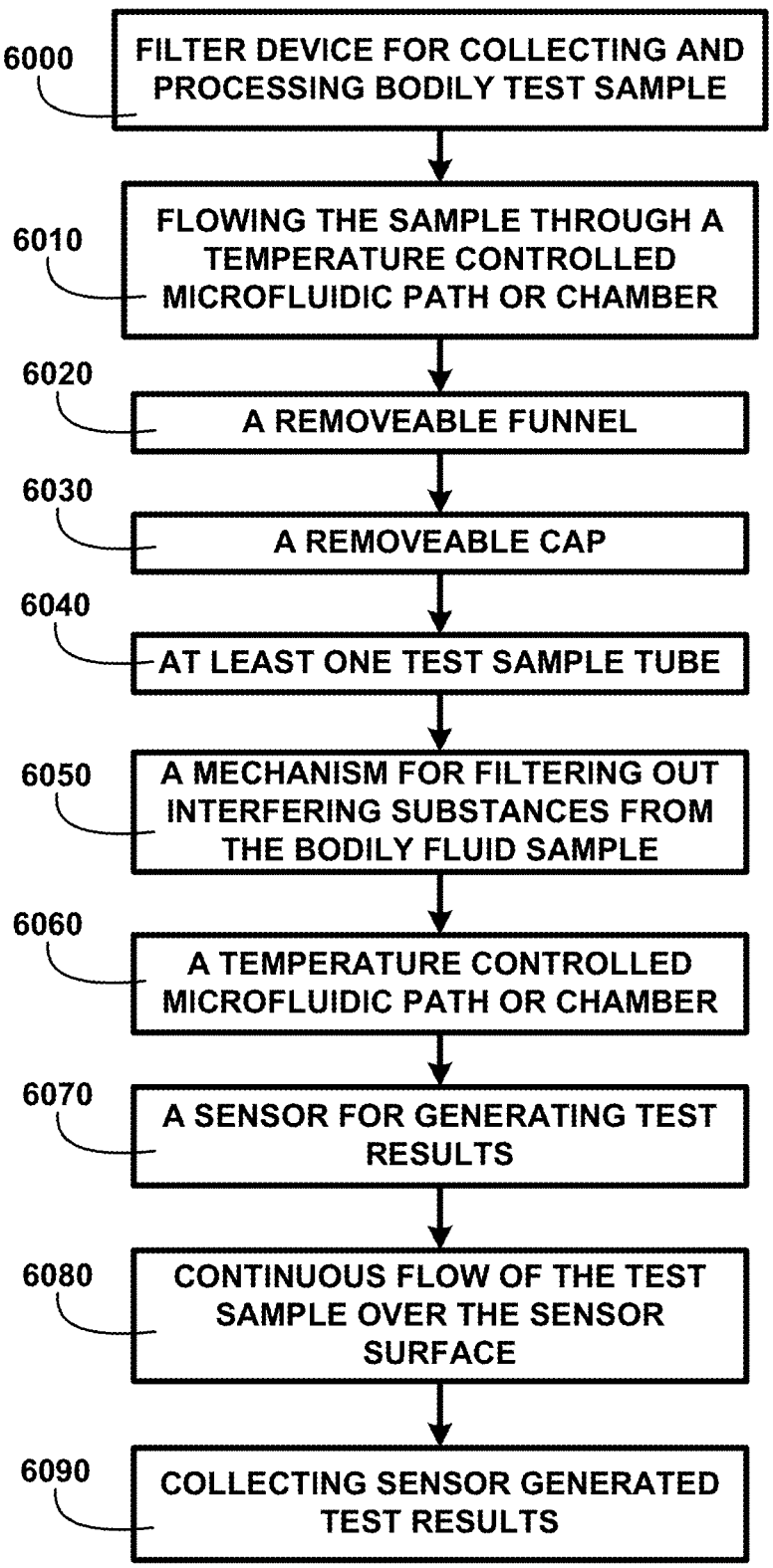
FIG. 58 shows a block diagram of an overview of a filter device of one embodiment.

Filter Device:

FIG. 58 shows a block diagram of an overview of a filter device of one embodiment. FIG. 58 shows a filter device for collecting and processing bodily test sample 6000 and flowing the sample through a temperature-controlled microfluidic path or chamber 6010. The filter device includes a removable funnel 6020, a removable cap 6030, at least one test sample tube 6040, a mechanism for filtering out interfering substances from the bodily fluid sample 6050, a temperature-controlled microfluidic path, or chamber 6060, a sensor for generating test results 6070. The filter device creates a continuous flow of the test sample over the sensor surface 6080. The filter device includes collecting sensor-generated test results 6090 of one embodiment.

Figure 59A:
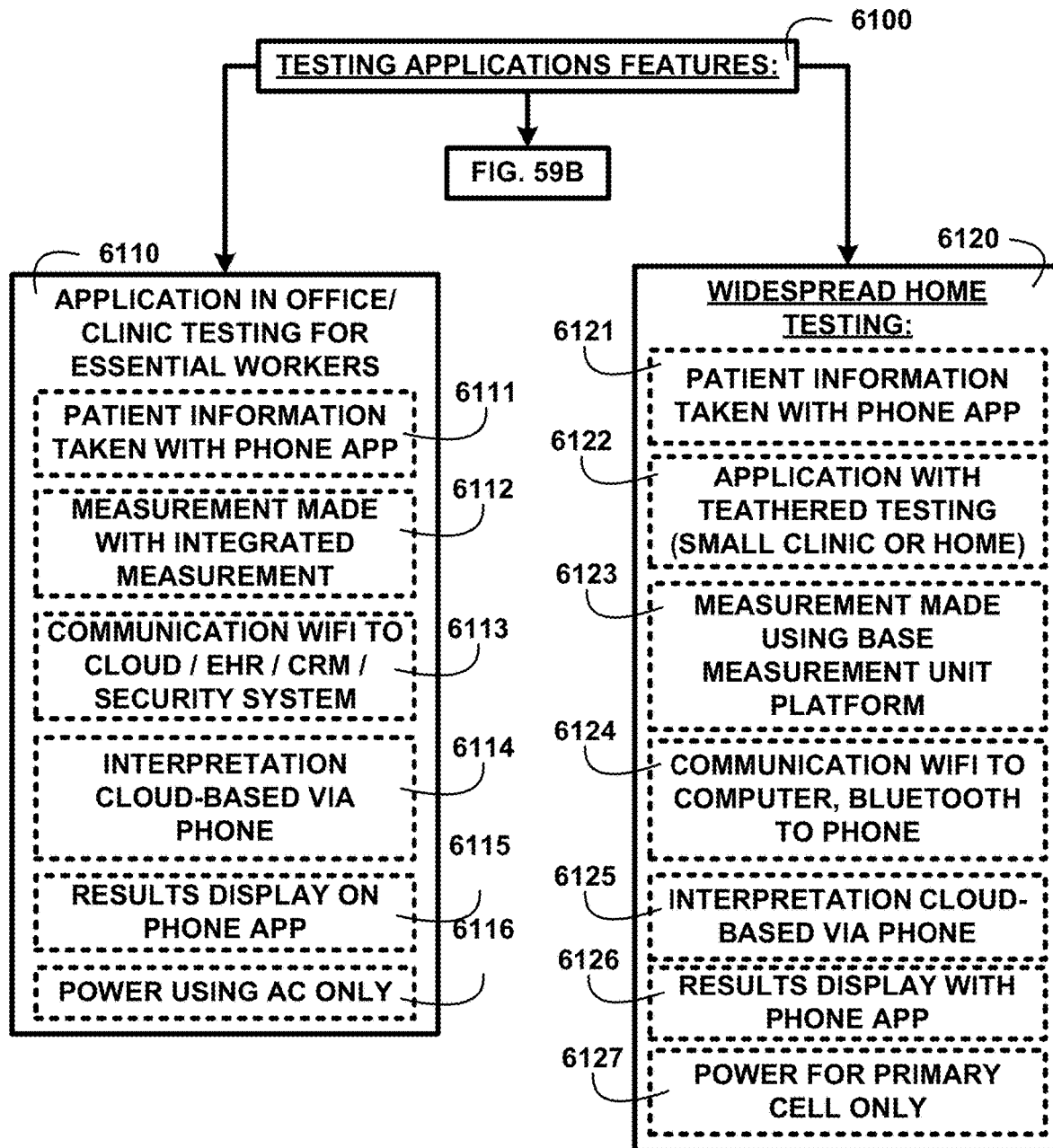
FIG. 59A shows a block diagram of an overview of testing applications features: of one embodiment.

Testing Applications Features:

FIG. 59A shows a block diagram of an overview of testing applications features: of one embodiment. FIG. 59A shows testing applications features: 6100. In one embodiment the testing applications features: 6100 include an application in office/clinic testing for essential workers 6110. This application includes patient information taken with phone app 6111. Testing measurement made with integrated measurement 6112. Communication WIFI to cloud/EHR/CRM/security system 6113 is performed for Interpretation cloud-based via phone 6114. Testing results display on phone app 6115. The application devices connect to power using AC only 6116.

In another embodiment a widespread home testing: 6120 testing application includes features including patient information taken with phone app 6121. Application with tethered testing (small clinic or home) 6122 is used for a measurement made using base measurement unit platform 6123.

Communication WIFI to computer, Bluetooth® to phone 6124 is used to perform interpretation cloud-based via phone 6125. Test results display with phone app 6126. The testing uses power for primary cell only 6127. Another testing application is described in FIG. 59B.

Figure 59B:
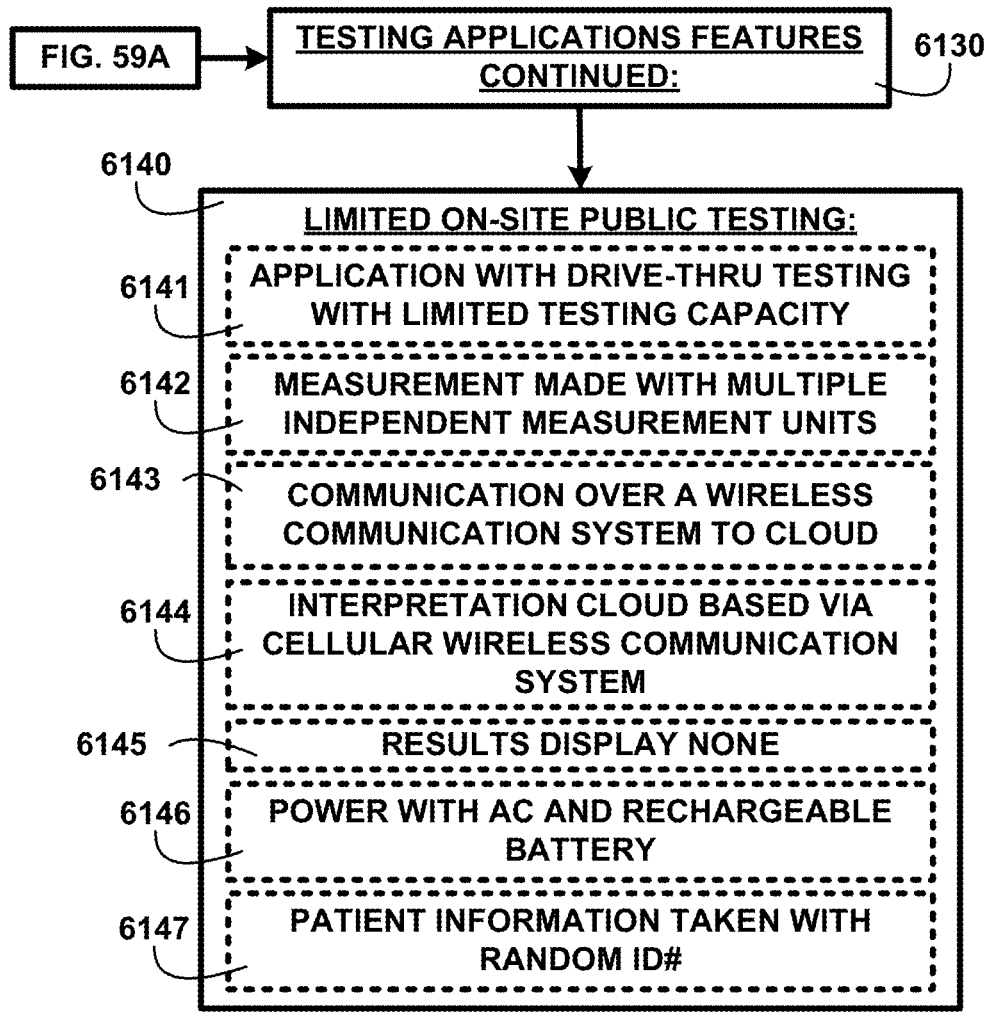
FIG. 59B shows a block diagram of an overview of testing applications features continued: of one embodiment.

Testing Applications Features Continued:

FIG. 59B shows a block diagram of an overview of testing applications features continued: of one embodiment. FIG. 59B shows a continuation from FIG. 59A of testing applications features continued: 6130 in an embodiment of limited on-site public testing: 6140. Limited on-site public testing: 6140 is an application with patient information taken with random id #6147. Limited on-site public testing: 6140 is performed with drive-thru testing with limited testing capacity 6141. Testing measurement made with multiple independent measurement units 6142. Communication over a wireless communication system to cloud 6143 is used for interpretation cloud-based via cellular wireless communication system 6144. Results display none 6145 as the cars are driving through with only a brief time for the test sampling. Power with AC and rechargeable battery 6146 is used to operate the devices of one embodiment.

Figure 60:
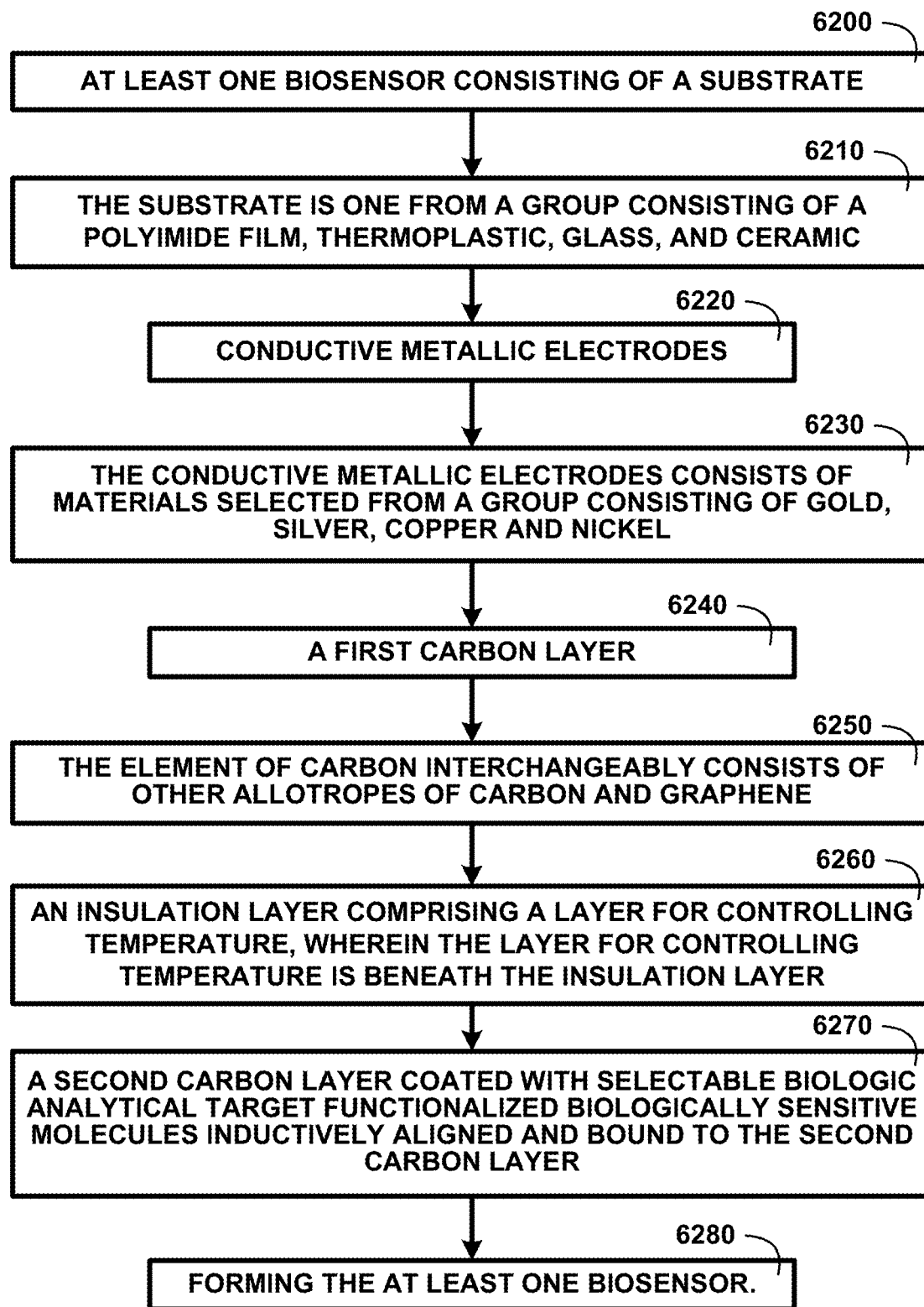
FIG. 60 shows for illustrative purposes only an example of two carbon layer biosensor of one embodiment.

Two Carbon Layer Biosensor:

FIG. 60 shows for illustrative purposes only an example of two carbon layer biosensor of one embodiment. FIG. 60 shows at least one biosensor consisting of a substrate 6200. The substrate is one from a group consisting of a polyimide film, thermoplastic, glass, and ceramic 6210. A plurality of conductive metallic electrodes 6220 are printed on the substrate. The conductive metallic electrodes consists of materials selected from a group consisting of gold, silver, copper and nickel 6230. A first carbon layer 6240 is deposited onto the substrate and plurality of conductive metallic electrodes.

The element of carbon interchangeably consists of other allotropes of carbon and Graphene 6250. An insulation layer comprising a layer for controlling temperature, wherein the layer for controlling temperature is beneath the insulation layer 6260 is deposited on the first carbon layer 6240. On top of the insulation layer 6260 a second carbon layer coated with selectable biologic analytical target functionalized biologically sensitive molecules inductively aligned and bound to the second carbon layer 6270 forming the at least one biosensor 6280 of one embodiment.

Figure 61:
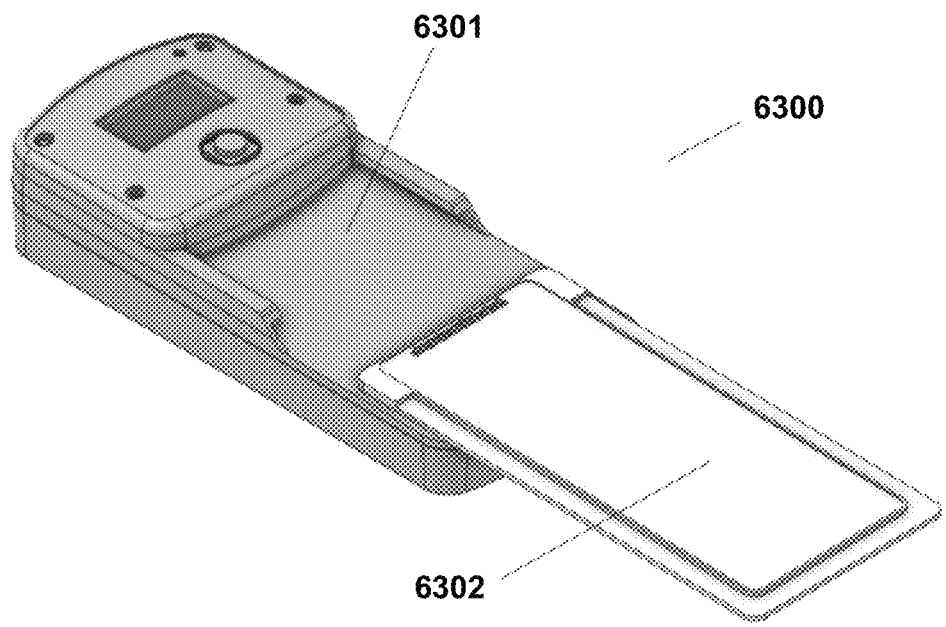
FIG. 61 shows for illustrative purposes only an example of an overview of physical implementation of a pathogen test system of one embodiment.

Physical Implementation of a Pathogen Test System:

FIG. 61 shows for illustrative purposes only an example of an overview of physical implementation of a pathogen test system of one embodiment. FIG. 61 shows the physical implementation of a Pathogen Test System 6300. The Pathogen Test System 6300 comprises a Reader 6301 and a Test Cartridge 6302. The Reader 6301 provides for the reading, processing of the readings, and transmitting test result data to another computer for further evaluation and notification. The Test Cartridge 6302 contains all of the necessary components for electronically identifying the test and processing steps required to execute the test, conditioning a sample, including heating, presenting the sample to one or more sensors, and providing an electronic connection to the Reader 6301 for gathering the test related data of one embodiment.

Figure 62:
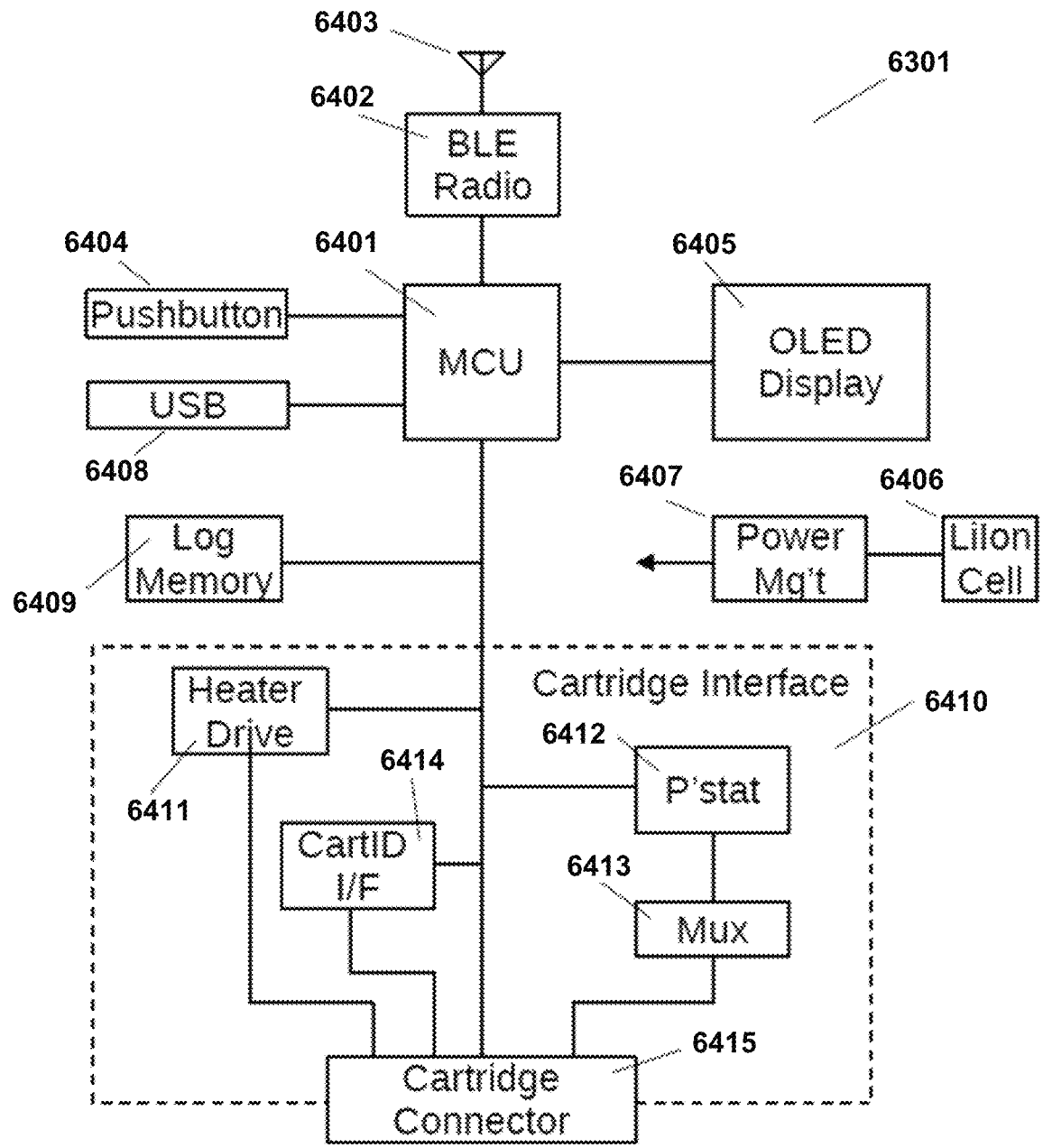
FIG. 62 shows for illustrative purposes only an example of a reader of one embodiment.

A Reader:

FIG. 62 shows for illustrative purposes only an example of a reader of one embodiment. FIG. 62 shows structure of the Reader 6301. The Reader 6301 comprises an MCU 6401 (Microcontroller Unit) which performs the main control and processing functions, and orchestrates all the functionality, for the Reader 6301. A USB connection 6408 provides wired power for charging and communication to the MCU from a wired interface. The USB connection 6408 is preferably an industry standard USB-C connection. Additional functionality in the MCU 6401 includes directly reading capacitive fluid sensors in the Test Cartridge 6302.

A BLE Radio 6402 provides for an RF link between the MCU 6401 and an external processing system such as a cellphone, PC, tablet computer, etc. The BLE Radio 6402 implements the standard Bluetooth® Special Interest Group protocol for Bluetooth® Low Energy communication. An Antenna 6403 performs the RF transmission and reception functions for the BLE Radio 6402.

An operator interface is provided by a Pushbutton 6404 in communication with the MCU 6401, allowing the operator to power the system and indicate the successful completion of operational steps. An OLED Display 6405 provides a visual display for the operator indicating status and requesting operator actions.

Power to the Reader 6301 is provided by an on-board LiIon Cell 6406. The LiIon Cell 6406 is an industry standard, rechargeable, Lithium Ion battery cell with internal protection from overcharging and under-discharging. A Power Management function 6407 receives power from the LiIon Cell 6406, controls the various voltage supplies for the Reader 6301, and provides battery status information to the MCU 6401. Additionally, the Power Management function 6407 receives power from the USB Connection 6408 and controls the voltage and current required to charge the LiIon Cell 6406.

A Log Memory 6409 is provided for non-volatile storage of operational parameters, intermediate test data, and completed test results. These test results may be communicated by the Reader 6301 immediately through the BLE Radio 6402 when a compatible computer is available, or at a later time when a compatible computer becomes available.

A Cartridge Interface 6410 is provided to adapt the interface of the Test Cartridge to the Reader 6301. The Cartridge Interface 6401 consists of a Heater Drive 6411 providing power and measurement of the heater function inside the Test Cartridge 6302, a Potentiostat 6412 used to drive and acquire measurements from the sensor functions inside the Test Cartridge 6302, a Multiplexer 6413 used to select which of the sensor functions to connect to the Potentiostat 6412 for measurement, a Cartridge ID Interface 6414 to protect and allow communication between the MCU 6401 and the electronic ID and processing step functions inside the Test Cartridge 6302, and a Cartridge Connector 6415 providing an electrical and electronic connection to the Test Cartridge 6302.

The Potentiostat 6412 can read 3-terminal electrochemical sensors or 2-terminal resistive sensors. The sensors can be read using techniques such as chronoamperometry, potentiometry, electro-impedance spectroscopy, etc., or a combination of techniques of one embodiment.

Figure 63:
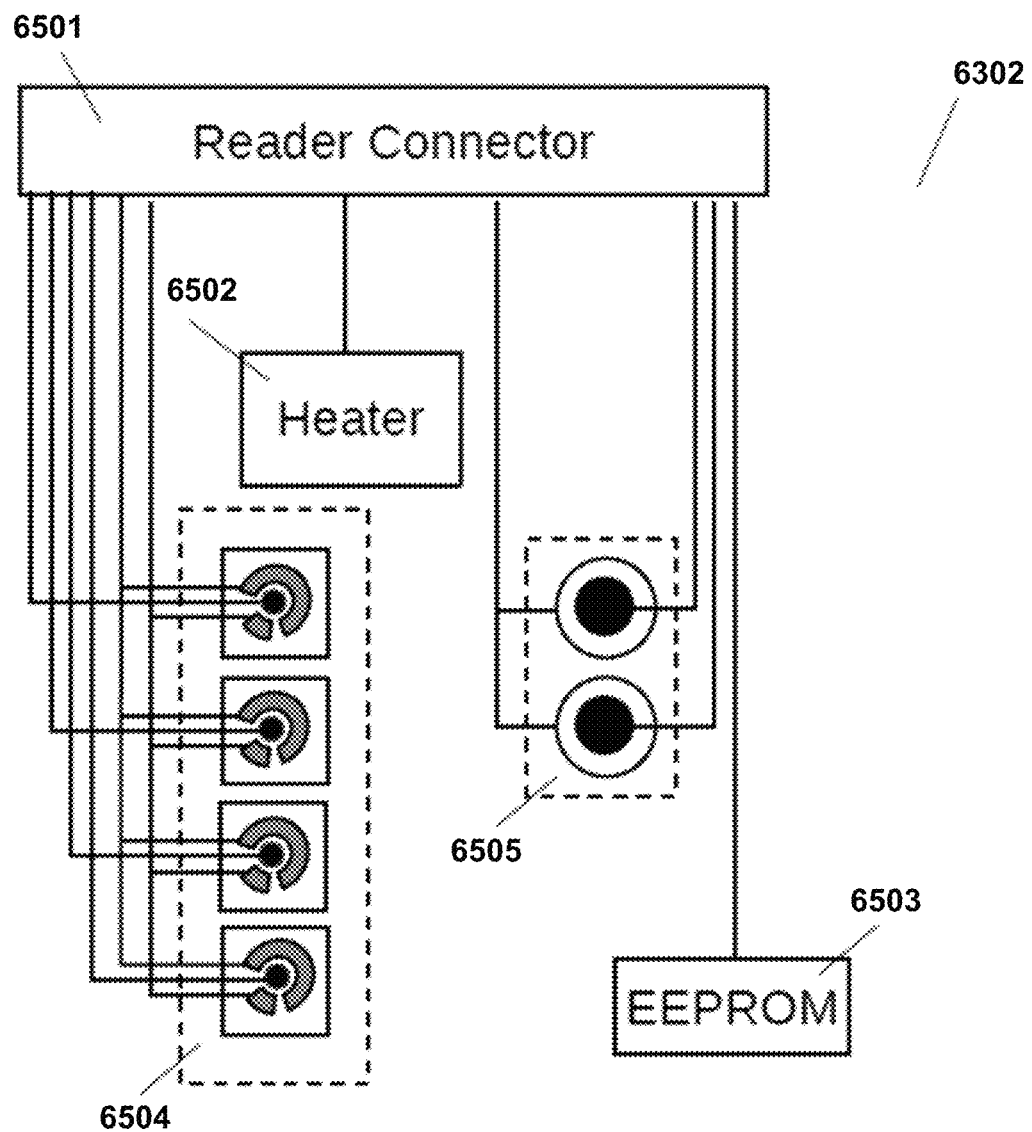
FIG. 63 shows for illustrative purposes only an example of an electrical diagram of the test cartridge of one embodiment.

An Electrical Diagram of the Test Cartridge:

FIG. 63 shows for illustrative purposes only an example of an electrical diagram of the test cartridge of one embodiment. FIG. 63 shows the electrical diagram of the Test Cartridge 6302. A Reader Connector 6501 provides for the electrical and electronic connection to the Cartridge Connector 6415.

A Heater 6502 provides a means for heating the sample. The Heater 6502 is preferably a PTC heater with a fixed setpoint temperature. The PTC resistance profile should be such that the resistance at the setpoint temperature is a fixed ratio to the resistance at ambient temperature. The Heater Drive 6411 first measures the resistance at ambient temperature, calculates a target resistance value at the setpoint temperature using the fixed ratio, then drives the Heater 6502, periodically measuring the PTC resistance, to achieve the setpoint temperature.

An EEPROM 6503 is provided for storing Test Cartridge 6302 and test execution information for the MCU 6401. This function may be implemented in one of a number of non-volatile memories including EEPROM, FRAM, FLASH, etc. Information is programmed in the EEPROM 6503 during manufacturing. Upon use of the Test Cartridge 6302 to perform a test, the MCU 6401 causes information to be written to the EEPROM 6503 indicating the Test Cartridge 6302 is no longer usable for testing.

A Sensor Array 6504 contains one or more electrochemical sensors for sensing analytes in the sample. The sensors in the Sensor Array 6504 may be 3-terminal electrochemical sensors, 2-terminal resistive sensors, or a combination of both. Other types of sensors contained in the sensor array can include: Microelectrochemical systems (MEMS) and/or Nanoelectromechanical systems (NEMS), metal oxide semiconductor, infrared sensor (nondispersive), thermal sensor (pellitor), photoionization (PID), chemiresistors, nano-particle based sensors, hybrid nanostructures, Quartz Microbalance, and/or field-effect transistor (FET) and Surface Acoustic Wave Sensors. Shown in FIG. 63, the Sensor Array 6504 consists of four electrochemical sensors. The sensors are arranged with a common Counter Electrode, common Reference Electrode, and four independent Working Electrodes.

Other sensors may be added, such as Fluid Presence 6505, depending on the requirements of the test performed. The Fluid Presence 6505 sensors are capacitive sensors which can sense the presence or absence of fluid at various points in the Test Cartridge 6302.

The EEPROM 6503 contains identification information (ie. serial number, manufacturing information, etc.) as well as storing a script to direct the MCU 6401 as to the proper sequence and operations required to successfully perform the test and extract the necessary data for further processing on external devices or systems. This capability allows the Test Cartridge 6302 itself to define how the test(s) physically implemented in it are to be executed and interpreted.

To access the test information from the EEPROM 6503, the MCU 6401 communicates through the Cartridge ID Interface 6414 to the EEPROM 6503 through the Cartridge Connector 6415, to retrieve the appropriate information from the Test Cartridge 6302. After retrieval of the test information, the MCU 6401 begins executing the script to perform the test.

The script portion of the test information contains a number of instructions for HMI interaction, timers, event management, acquisition engines and program control. The execution of these instructions defines the successful test execution. While these instructions are compiled in a terse binary format for storage in the EEPROM 6503, the representations of these instructions is shown in a JSON format which is ultimately compiled for storage in the EEPROM 6503. Each instruction has an optional "label" parameter which allows for reference by the Program Control instructions.

HMI interaction: The PRINT instruction is used to display information on the OLED Display 6405. An example of the instruction and its parameters is shown below:

```
PRINT
{
("label": <string: labelString>,)
"action": "Display",
"state": <string: displayText>
}
```

Timers: The TIMER instruction is used to set one of four timers to trigger an event at some time in the future. Event management and program control instructions use these events to manage the test sequence. An example of the instruction and its parameters is shown below:

```
TIMER
{
("label": <string: labelString>,)
"action": "Timer",
"object": <string: "0"|"1"|"2"|"3">
"state": <integer: durationMs>
}
```

Event management: The event management instructions include the WAIT family of instructions. These instructions pause program execution until the proper event conditions are available. These WA and WAT format instructions include:

WALL continues when all of the listed object events occur.

WANY continues when any one of the listed object events occur.

WALLT continues when all of the listed object events occur or the wait duration times out.

WANYT continues when any one of the listed object events occur or the wait duration times out.

An example of the WA** instructions and their parameters is shown below:

```
WALL/WANY {
("label": <string: labelString>,)
"action": "WaitFor",
"object": <string:
"Timer0"|"Timer1"|"Timer2"|"Timer3"|"Pushbutton"|
"Outlet"|"Inlet"|"Heater"|"HeaterFail"|"Used">,
"state": <string: "all"|"any">
}
```

Examples of the WA**T instructions and their parameters is shown below:

```
WALLT    {
("label": <string: labelString>,)
"action": "WaitForAll",
"object": <string: "Timer0"|"Timer1 "|"Timer2"|"Timer3|"Pushbutton"|
"Outlet"|"Inlet"|"Heater"|"HeaterFail"|"Used">, "state": <integer: durationS>
}
WANYT    {
("label": <string: labelString>,)
"action": "WaitForAny",
"object": <string: "Timer0"|"Timer1 "|"Timer2"|"Timer3|"Pushbutton"|
"Outlet"|"Inlet"|"Heater"|"HeaterFail"|"Used">
"state": <integer: durationS>
}
```

Acquisition Engines (heater, potentiostat, fluid sensors, etc.): Several of the functions require continuous operation, and are driven by Acquisition Engines. These ongoing functions control the Heater Drive 6411 power, take readings of the multiplexed sensors using the Potentiostat 6412, or Fluid Presence 6505 sensors that may be in the Test Cartridge 6302. The ACQ instructions control the operation of the Acquisition Engines. An example of the instruction and its parameters is shown below:

```
ACQ {
("label": <string: labelString>,)
"action": "Assert",
"object": <string: "Heater"|"Outlet"|"Inlet"|
sensorNameString"_Start"|sensorNameString"_Acquire">,
"state": <string: "active"|"inactive">
}
```

Program Control: The program control instructions allow conditional and unconditional changing of the execution flow based on events. The conditional instructions check a single or combination of events to determine program flow. The event conditions are outlined below:

ALL—execution branch if all of the object events have occurred.

ANY—execution branch if any one of the object events have occurred.

NONE—execution branch if any one of the object events have not occurred.

NotALL—execution branch if all of the object events have not occurred.

BRA—Unconditional execution branch.

An example of this instruction and its parameters is shown below:

```
BCOND{
("label": <string: labelString>,)
"action": "BranchConditional",
"object": <string: "Timer0"|"Timer1"|"Timer2"|"Timer3"|"Pushbutton"|
"Outlet"|"Inlet"|"Heater"|"HeaterFail"|"Used">,
"state": <string: "all"|"any"|"none"|"notAll">,
"jump": <string: labelString>
}
```

The unconditional instructions modify program flow with no regard to events. Because of the encoding restrictions, there are two unconditional instructions, depending on the distance to the label the instruction requires. BRA is a compact instruction which has a limited range to branch to.

GOTO is an expanded instruction with an unlimited branch range. An example of the BRA instruction and its parameters is shown below:

```
BRA {
("label": <string: labelString>,)
"action": "Branch Conditional",
"object": ,
"state": <string: "all">,
"jump": <string: labelString>
}
```

An example of the GOTO instruction and its parameters is shown below:

```
GOTO{
("label": <string: labelString>,)
"action": "Goto",
"jump": <string: labelString>
}
```

The final instruction terminates execution of the script and signals to the main program running in the MCU 6401 the status of the test. An example of the QUIT instruction and its parameters is shown below:

```
QUIT {
("label": <string: labelString>,)
"action": "End",
"state": <string: "normal"|"failedUnused"|"failedUsed">
}
```

Figure 64:
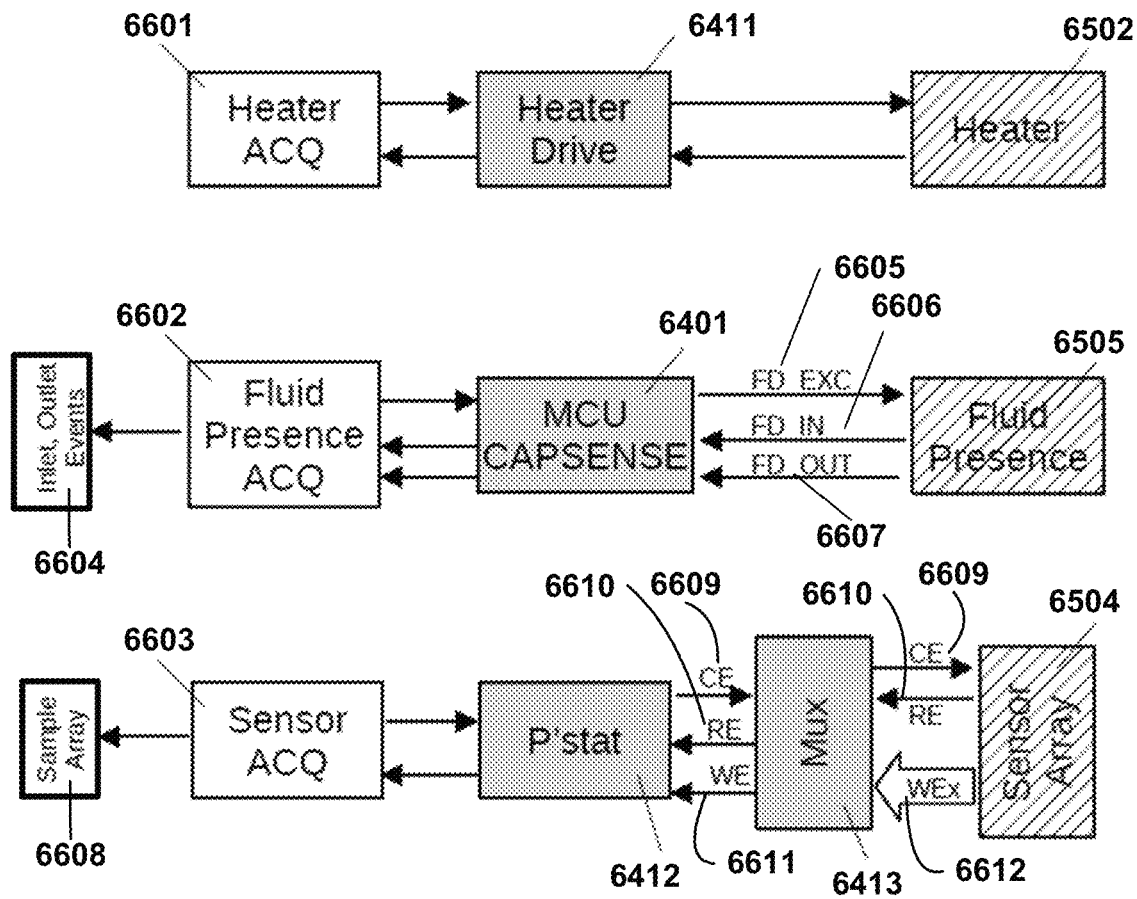
FIG. 64 shows for illustrative purposes only an example of acquisition engines of one embodiment.

Acquisition Engines:

FIG. 64 shows for illustrative purposes only an example of acquisition engines of one embodiment. FIG. 64 shows the use of the Acquisition Engines. An acquisition engine is firmware executed by the MCU 6401 which, when started by the script, performs a time-series operation independent of the script code execution. The different acquisition engines provide different levels of control, events or data, depending on their function.

The Heater ACQ 6601 engine controls the Heater Drive 6411 hardware which continuously controls the temperature of the Heater 6502 at the appropriate temperature. Heater Drive 6411 is controlled by a PWM output of the MCU 6302, and provides resistance measurement to an analog input of the MCU 6302. During an active portion of the PWM cycle, power is applied to the Heater 6502, and the current is measured by a voltage drop across a fixed resistance. The resistance of the Heater 6502 is calculated by multiplying the voltage applied and the current measured.

When the Heater ACQ 6601 engine is started by the following script command:

```
ACQ {
"action": "Assert",
"object": "Heater",
"state": "active"
}
```

The PWM is started, and the resistance of the Heater 6502 is calculated. A firmware control loop executed by the MCU 6302 periodically adjusts the active portion of the PWM cycle to increase the PTC resistance of the Heater 6502 to a fixed ratio above the resistance at ambient temperature. This control loop continues until the Heater ACQ 6601 engine is deactivated:

```
ACQ {
"action": "Assert",
"object": "Heater",
"state": "inactive"
}
```

The Heater ACQ 6601 engine provides no further events or data for script execution. The Fluid Presence ACQ 6602 engine monitors the Fluid Presence 6505 sensors for indication that sample or other fluid has reached certain locations within the Test Cartridge 6302. Specifically, one sensor is located where fluid enters the Sensor Array 6604 (FD_IN), and one sensor is located where the fluid exits the Sensor Array 6604 (FD_OUT). The fluid detection is performed by dedicated CAPSENSE hardware in the MCU 6401. This hardware provides a common exciter output (FD_EXC) to the Fluid Presence 6505 sensors, and evaluates the capacitance change as reported by FD_IN and FD_OUT.

When the Fluid Presence ACQ 6602 engine is started by the following script command:

```
ACQ {
"action": "Assert",
"object": "Outlet","Inlet"
"state": "active"
}
```

An initial capacitance estimate is collected as a reference to account for stray implementation capacitances. Future readings are compared to the reference to determine if the sensor has encountered fluid. If a fluid has been detected, the Fluid Presence ACQ 6602 engine indicates "Outlet" or "Inlet" events to the script interpreter for managing the script execution flow.

The Sensor ACQ 6603 engine controls the acquisition of time-series data from the Sensor Array 304. The Sensor ACQ 6603 engine firmware controls the Multiplexer 6413 to select one of the sensors in the Sensor Array 6603 and controls, and reads from, the Potentiostat (P'stst) 6412.

At the beginning of a test, before fluid has been introduced to the sensor array, the Sensor ACQ 6603 engine is started by the following script command to a sample array 6608:

```
ACQ {
"action": "Assert",
"object": "SENSOR1_Start", SENSOR2_Start, SENSOR3_Start,
SENSOR4_Start,
"state": "active"
}
```

This initializes the Potentiostat (P'stst) 6412 and the Multiplexer 6413 and begins the control process RE6610, WE 6611, WEx6612, but not the actual acquisition of data from the Potentiostat (P'stst) 6412. This is done to charge any excess capacitance in the sensor, and polarize the sensor for future data acquisition.

Typically, when fluid is detected at the inlet of the Sensor Array 6504, acquisition of data is started by the following script command:

```
ACQ {
"action": "Assert",
"object": "SENSOR1_Acquire", SENSOR2_Acquire,
"SENSOR3_Acquire, SENSOR4_Acquire,
"state": "active"
}
```

During acquisition, a time-series of data from the Potentiostat 6412 is collected for each of the noted sensors. When data collection is determined to be finished, acquisition is terminate, and sensor acquisition shut down by the following script commands:

```
ACQ {
"action": "Assert",
"object": "SENSOR1_Acquire", SENSOR2_Acquire,
"SENSOR3_Acquire, SENSOR4_Acquire,
"state": "inactive"
}
ACQ {
"action": "Assert",
"object": "SENSOR1_Start", SENSOR2_Start, SENSOR3_Start,
SENSOR4_Start,
"state": "inactive"
}
```

Note that not all sensors are required to be activated or acquired at the same time, but a combination of sensors may be activated/inactivated or acquired arbitrarily under script control.

Vectorization:

After the time-series acquisition of the readings from the Sensor Array 6504 has been completed, the data needs to be compressed into a vector representation of the data to minimize the amount of data required to be transmitted. The vector representation extracts the important features from the time-series data and transmits the features for further analysis.

Because of manufacturing variations in the construction and sensitization of the individual sensors in the Sensor Array 6504, the first step is to transform the absolute value readings of the time-series in the measurement domain, into a time series of relative data. This is performed by taking the initial value in a measurement window and referencing all subsequent values as a percentage change from the initial value.

Figure 65:
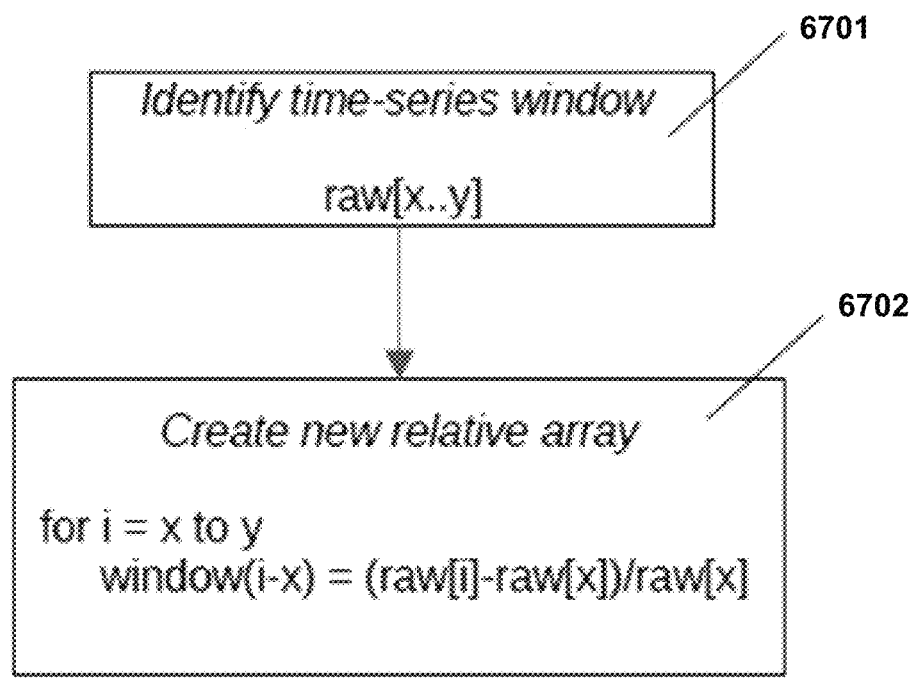
FIG. 65 shows for illustrative purposes only an example of time-series window is identified of one embodiment.

Time-Series Window is Identified:

FIG. 65 shows for illustrative purposes only an example of time-series window is identified of one embodiment. FIG. 65 shows a flowchart of this process where the time-series window is identified 6701 and a baseline relative time-series 6702 is created. The original time series in the measurement domain begins at the time the Sensor ACQ 6603 engine is instructed through the script to begin acquisition. The array of the time series continues until the Sensor ACQ 6603 engine is instructed through the script to complete acquisition. A window of interest is determined on this array, and is typically from the beginning of acquisition through the complete acquisition, ie. the entire array. This is not always the case, and other determinants may be used to identify the window of interest.

After the time-series window is identified 6701, a baseline relative time-series 6702 is created by calculating the deviation from the initial window value in percentage, and shifting it to a 0 based array for uniform handling of one embodiment.

Time Series (Measurement Domain):

FIG. 66 shows for illustrative purposes only an example of time series (measurement domain) of one embodiment. FIG. 66 shows the results of this process, where the window of interest in the Time Series (measurement domain) 6801 is shifted to a 0 based array and transformed into the baseline relative domain 6802 of one embodiment.

Maximum Relative Value:

FIG. 67 shows for illustrative purposes only an example of maximum relative value of one embodiment. FIG. 67 shows in this implementation, there are 5 parameters extracted from the baseline relative domain. A minValWindow 6901 (the minimum relative value reported in the window), maxValWindow 6902 (the maximum relative value reported in the window), areaOverWindow 6903 (the positive area under the baseline relative domain curve), areaUnderWindow 6904 (the negative area under the baseline relative domain curve), and averageOverWindow 6905 (the average value of all values in the baseline relative domain curve). The following table lists the vector parameters and values for the example shown in FIG. 66.

| Vector Parameter | Value |
| --- | --- |
| minValWindow | −10.0% |
| maxValWindow | 10.0% |
| areaOverWindow | 318.2% |
| areaUnderWindow | 318.2% |
| averageOverWindow | 0.0% |

Positive Reading Test:

FIG. 68 shows for illustrative purposes only an example of a positive reading test of one embodiment. FIG. 68 shows an example that demonstrates the transformation from a time-series in the measurement domain of a 901 7001 to the baseline relative domain of a Positive reading test 7002. Below is a list of vector parameters calculated from the baseline relative domain of a Positive reading test 7002.

| Vector Parameter | Value |
| --- | --- |
| minValWindow | −0.6% |
| maxValWindow | 5.8% |
| areaOverWindow | 257.1% |
| areaUnderWindow | −4.2% |
| averageOverWindow | 2.5% |

Negative Reading Test:

FIG. 69 shows for illustrative purposes only an example of a negative reading test of one embodiment. FIG. 69 demonstrates the transformation from a time-series in the measurement domain of a Negative reading test 7101 to the baseline relative domain of a Negative reading test 7102. Below is a list of vector parameters calculated from the baseline relative domain of a Negative reading test 7102.

| Vector Parameter | Value |
| --- | --- |
| minValWindow | −5.9% |
| maxValWindow | 0.0% |
| areaOverWindow | 0.0% |
| areaUnderWindow | −517.3% |
| averageOverWindow | −5.17% |

It should be understood that various other feature extraction algorithms may be used in addition to, or instead of, those shown, depending on the characteristics of the specific electrochemical sensors used. These algorithms could include specific values at specific times, the times of inflection points (derivative of the baseline relative domain=0), linear fit characteristics (slope and intercept) and spline or polynomial fit to encompass the shape of the function without all of the detail.

Interpretation: Interpretation of the test results is preferably done remote to the Reader 6301 to ensure test results get accurately recorded and transmitted to governmental agencies (where required). The feature vector from the test (ie. the collection of extracted data from the time-series data) is calculated and collected by the MCU 6401, formatted and sent to a host computer system via BLE using the BLE Radio 6402 and Antenna 6403. This allows the host computer system to interpret the results of the tests according to the current best approach, rather than an approach which was committed at test manufacture time, and loaded into the EEPROM 6503.

In the remote system, the feature vector from the test is analyzed for integrity by determining the test results of each sensor in the Sensor Array 6504 and comparing the results of all the test results for confirmation of a valid test, and coherent results. The determination of test results for each sensor, and the comparison of results for all sensors can be performed using a rules-based system, or a machine learning system, where the interaction between the sensors is deterministic but not readily quantifiable.

The foregoing has described the principles, embodiments, and modes of operation of the present invention. However, the invention should not be construed as being limited to the particular embodiments discussed. The above-described embodiments should be regarded as illustrative rather than restrictive, and it should be appreciated that variations may be made in those embodiments by workers skilled in the art without departing from the scope of the present invention as defined by the following claims.

What is claimed is:

1. An apparatus, comprising:
 a human pathogen test system configured for performing a test for detecting human patient biologic analytical target pathogens;
 at least one impedimetric detection module coupled to the human pathogen test system configured for detecting multiple types of pathogens using impedimetric detection of human patient biologic analytical target pathogens;
 an electrical field and ionic strength measuring device coupled to the human pathogen test system configured to measure the electrical field and ionic strength of the test sample and control sensing speed performance;
 a reader coupled to the human pathogen test system configured for reading capacitive fluid sensors test data, processing of extracted test data readings, and transmitting test results data to a computer for further evaluation and notification;
 a microcontroller unit coupled to the reader configured for performing main control and processing functions, and orchestrating functionality for the reader;
 a reader log memory device configured for non-volatile storage of operational parameters, intermediate test data, and completed test results;
 an RF link configured for test data communication between the microcontroller unit and an external processing system including transmitting intermediate test data and completed test results to the external processing system;
 a feature vector determined from extracted test data from time-series data is calculated and collected by the microcontroller unit, formatted and sent to a computer system; and
 wherein, the feature vector from the extracted test data is analyzed for integrity by determining test results of each sensor in a sensor array and comparing the results of all sensor array individual sensor test results for confirmation of a valid test, and coherent results.

2. The apparatus of claim 1 further comprising the feature vector determination of extracted test data results is configured for each sensor, and the comparison of results for all sensors to be performed using a rules-based system, wherein interaction between the sensors is deterministic but not readily quantifiable.

3. The apparatus of claim 1, further comprising the feature vector determination of extracted test data results is configured for each sensor, and the comparison of results for all sensors can be performed using a machine learning system, wherein interaction between the sensors is deterministic but not readily quantifiable.

4. The apparatus of claim 1, further comprising a microcontroller unit feature vector calculation is configured for transformation from a time-series in a measurement domain of a negative reading test to a baseline relative domain of a negative reading test.

5. The apparatus of claim 1, further comprising a microcontroller unit feature vector calculation is configured for transformation from a time-series in the measurement domain of a positive reading test to a baseline relative domain of a positive reading test.

6. The apparatus of claim 1, further comprising a microcontroller unit feature vector calculation is configured for a maximum relative value with five parameters including a minimum relative value, maximum relative value, positive area under the baseline relative domain curve, negative area under a baseline relative domain curve, and average value of all values in the baseline relative domain curve.

* * * * *